(12) United States Patent
van Duzer et al.

(10) Patent No.: US 8,394,810 B2
(45) Date of Patent: Mar. 12, 2013

(54) REVERSE AMIDE COMPOUNDS AS PROTEIN DEACETYLASE INHIBITORS AND METHODS OF USE THEREOF

(75) Inventors: John H. van Duzer, Georgetown, MA (US); Ralph Mazitschek, Arlington, MA (US); Walter Ogier, Winchester, MA (US); James E. Bradner, Cambridge, MA (US); Guoxiang Huang, Kernersville, NC (US); Dejian Xie, Shanghai (CN); Nan Yu, Shanghai (CN)

(73) Assignee: Acetylon Pharmaceuticals, Boston, MA (US)

( * ) Notice: Subject to any disclaimer, the term of this patent is extended or adjusted under 35 U.S.C. 154(b) by 29 days.

(21) Appl. No.: 13/010,974

(22) Filed: Jan. 21, 2011

(65) Prior Publication Data

US 2011/0300134 A1 Dec. 8, 2011

Related U.S. Application Data

(60) Provisional application No. 61/336,460, filed on Jan. 22, 2010.

(51) Int. Cl.
*A61K 31/505* (2006.01)

(52) U.S. Cl. ...................................... 514/275

(58) Field of Classification Search .................... 514/275
See application file for complete search history.

(56) References Cited

U.S. PATENT DOCUMENTS

| | | | |
|---|---|---|---|
| 6,777,217 | B1 | 8/2004 | Schreiber et al. |
| 7,244,853 | B2 | 7/2007 | Schreiber et al. |
| 7,250,504 | B2 | 7/2007 | Grozinger et al. |
| 7,994,362 | B2 | 8/2011 | Schreiber et al. |
| 2004/0266769 | A1 | 12/2004 | Bressi |
| 2006/0239909 | A1 | 10/2006 | Anderson |
| 2007/0093413 | A1 | 4/2007 | Schreiber |
| 2007/0149495 | A1 | 6/2007 | Bressi |
| 2009/0023786 | A1 | 1/2009 | Miller |
| 2009/0209590 | A1 | 8/2009 | Mazitschek |
| 2009/0305384 | A1 | 12/2009 | Grozinger |
| 2009/0312363 | A1 | 12/2009 | Bradner |
| 2010/0137196 | A1 | 6/2010 | Schreiber |
| 2011/0218154 | A1 | 9/2011 | Schreiber |

FOREIGN PATENT DOCUMENTS

| | | |
|---|---|---|
| WO | WO 03 037869 | 5/2003 |
| WO | WO 2006 102557 | 9/2006 |
| WO | WO 2007 130429 | 11/2007 |
| WO | WO 2008 091349 | 7/2008 |
| WO | WO 2010 011296 | 1/2010 |
| WO | WO 2011 019393 | 2/2011 |
| WO | WO 2011 084991 | 7/2011 |

OTHER PUBLICATIONS

Butler, et al., "Suberoylanilide Hydroxamic Acid, an Inhibitor of Histone Deacetylase, Suppresses the Growth of Prostate Cancer Cells in Vitro and in Vivo", Cancer Research 60, 5165-5170, Sep. 15, 2000.
Haggarty, et al., "Domain-selective small-molecule inhibitor of histone deacetylase 6 (HDAC6)-mediated tubulin deacetylation", PNAS, vol. 100, No. 8, 4389-4394, 2003.
Co-pending U.S. Appl. No. 13/437,672, filed Apr. 2, 2012.
International Search Report and Written Opinion for PCT/US2011/021982, Mailed Oct. 10, 2011.
File History of U.S. Patent No. 8,148,526, issued Apr. 3, 2012.

*Primary Examiner* — Rebecca Anderson
(74) *Attorney, Agent, or Firm* — Lathrop & Gage LLP; Brian C. Trinque; Giulio A. DeConti

(57) ABSTRACT

The present invention relates to novel "reverse amide" compounds comprising a zinc chelator group, and the use of such compounds in the inhibition of HDAC6 and in the treatment of various diseases, disorders or conditions related to HDAC6.

4 Claims, No Drawings

REVERSE AMIDE COMPOUNDS AS PROTEIN DEACETYLASE INHIBITORS AND METHODS OF USE THEREOF

PRIORITY BENEFIT

This application claims the benefit U.S. Provisional application 61/336,460, filed on Jan. 22, 2010, the contents of which are incorporated herein in its entirety.

BACKGROUND OF THE INVENTION

The identification of small organic molecules that affect specific biological functions is an endeavor that impacts both biology and medicine. Such molecules are useful as therapeutic agents and as probes of biological function. Such small molecules have been useful at elucidating signal transduction pathways by acting as chemical protein knockouts, thereby causing a loss of protein function. (Schreiber et al, J. Am. Chem. Soc, 1990, 112, 5583; Mitchison, Chem. and Biol., 1994, I5 3) Additionally, due to the interaction of these small molecules with particular biological targets and their ability to affect specific biological function (e.g. gene transcription), they may also serve as candidates for the development of new therapeutics.

One biological target of recent interest is histone deacetylase (HDAC) (see, for example, a discussion of the use of inhibitors of histone deacetylases for the treatment of cancer: Marks et al. Nature Reviews Cancer 2001, 7,194; Johnstone et al. Nature Reviews Drug Discovery 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al Curr. Opin. Chem. Biol. 1997, 1, 300-308). HDACs participate in cellular pathways that control cell shape and differentiation, and an HDAC inhibitor has been shown effective in treating an otherwise recalcitrant cancer (Warrell et al J. Natl. Cancer Inst. 1998, 90, 1621-1625). At this time, eleven human HDACs, which use Zn as a cofactor, have been identified (Taunton et al. Science 1996, 272, 408-411; Yang et al. J. Biol. Chem. 1997, 272, 28001-28007. Grozinger et al. Proc. Natl. Acad. Sci. U.S.A. 1999, 96, 4868-4873; Kao et al. Genes Dev. 2000, 14, 55-66. Hu et al J. Biol. Chem. 2000, 275, 15254-15264; Zhou et al. Proc. Natl. Acad. Sci, U.S.A. 2001, 98, 10572-10577; Venter et al. Science 2001, 291, 1304-1351) these members fall into three classes (class I, II, and IV). An additional seven HDACs have been identified which use NAD as a cofactor. To date, no small molecules are known that selectively target any particular class or individual members of this family ((for example ortholog-selective HDAC inhibitors have been reported: (a) Meinke et al. J. Med. Chem. 2000, 14, 4919-4922; (b) Meinke, et al Curr. Med. Chem. 2001, 8, 211-235). There remains a need for preparing structurally diverse HDAC and tubulin deacetylase (TDAC) inhibitors particularly ones that are potent and/or selective inhibitors of particular classes of HDACs or TDACs and individual HDACs and TDACs.

Recently, a cytoplasmic histone deacetylase protein, HDAC6, was identified as necessary for aggresome formation and for survival of cells following ubiquitinated misfolded protein stress. The aggresome is an integral component of survival in cancer cells. The mechanism of HDAC6-mediated aggresome formation is a consequence of the catalytic activity of the carboxy-terminal deacetylase domain, targeting an uncharacterized non-histone target. The present invention also provides small molecule inhibitors of HDAC6. In certain embodiments, these new compounds are potent and selective inhibitors of HDAC6.

The aggresome was first described in 1998, when it was reported that there was an appearance of microtubule-associated perinuclear inclusion bodies in cells over-expressing the pathologic ΔF508 allele of the cystic fibrosis transmembrane conductance receptor (CFTR). Subsequent reports identified a pathologic appearance of the aggresome with over-expressed presenilin-1 (Johnston J A, et al. J Cell Biol. 1998; 143:1883-1898), parkin (Junn E, et al. J Biol Chem. 2002; 277: 47870-47877), peripheral myelin protein PMP22 (Notterpek L, et al. Neurobiol Dis. 1999; 6: 450-460), influenza virus nucleoprotein (Anton L C, et al. J Cell Biol. 1999; 146:113-124), a chimera of GFP and the membrane transport protein pi 15 (Garcia-Mata R, et al. J Cell Biol. 1999; 146: 1239-1254) and notably amyloidogenic light chains (DuI J L, et al. J Cell Biol. 2001; 152:705-716). Model systems have been established to study ubiquitinated (ΔF508 CFTR) (Johnston J A, et al. J Cell Biol. 1998; 143:1883-1898) and non-ubiquitinated (GFP-250) (Garcia-Mata R, et al. J Cell Biol. 1999; 146:1239-1254) protein aggregate transport to the aggresome. Secretory, mutated, and wild-type proteins may assume unstable kinetic intermediates resulting in stable aggregates incapable of degradation through the narrow channel of the 26S proteasome. These complexes undergo active, retrograde transport by dynein to the pericentriolar aggresome, mediated in part by a cytoplasmic histone deacetylase, HDAC6 (Kawaguchi Y, et al. Cell. 2003; 1 15:727-738).

Histone deacetylases are a family of at least 11 zinc-binding hydrolases, which catalyze the deacetylation of lysine residues on histone proteins. HDAC inhibition results in hyperacetylation of chromatin, alterations in transcription, growth arrest, and apoptosis in cancer cell lines. Early phase clinical trials with available nonselective HDAC inhibitors demonstrate responses in hematologic malignancies including multiple myeloma, although with significant toxicity. Of note, in vitro synergy of conventional chemotherapy agents (such as melphalan) with bortezomib has been reported in myeloma cell lines, though dual proteasome-aggresome inhibition was not proposed. Until recently selective HDAC inhibitors have not been realized.

HDAC6 is required for aggresome formation with ubiquitinated protein stress and is essential for cellular viability in this context. HDAC6 is believed to bind ubiquitinated proteins through a zinc finger domain and interacts with the dynein motor complex through another discrete binding motif. HDAC6 possesses two catalytic deacetylase domains. It is not presently known whether the amino-terminal histone deacetylase or the carboxy-terminal tubulin deacetylase (TDAC) domain mediates aggresome formation.

Aberrant protein catabolism is a hallmark of cancer, and is implicated in the stabilization of oncogenic proteins and the degradation of tumor suppressors (Adams J. Nat Rev Cancer. 2004; 4:349-360). Tumor necrosis factor alpha induced activation of nuclear factor kappa B (NFKB) is a relevant example, mediated by NFKB inhibitor beta (IKB) proteolytic degradation in malignant plasma cells. The inhibition of IKB catabolism by proteasome inhibitors explains, in part, the apoptotic growth arrest of treated myeloma cells (Hideshima T, et al. Cancer Res. 2001; 61:3071-3076). Multiple myeloma is an ideal system for studying the mechanisms of protein degradation in cancer. Since William Russell in 1890, cytoplasmic inclusions have been regarded as a defining histological feature of malignant plasma cells. Though the precise composition of Russell bodies is not known, they are regarded as ER-derived vesicles containing aggregates of monotypic immunoglobulins (Kopito R R, Sitia R. EMBO Rep. 2000; 1:225-231) and stain positive for ubiquitin (Manetto V, et al. Am J Pathol. 1989; 134:505-513). Russell bodies have been described with CFTR over-expression in yeast (Sullivan M L, et al. J. Histochem. Cytochem. 2003; 51:545-548), thus raising the suspicion that these structures may be linked to overwhelmed protein catabolism, and potentially the aggresome. The role of the aggresome in cancer remains undefined.

Aberrant histone deacetylase activity has also been linked to various neurological and neurodegenerative disorders, including stroke, Huntington's disease, Amyotrophic Lateral Sclerosis and Alzheimer's disease. HDAC inhibition may induce the expression of anti-mitotic and anti-apoptotic genes, such as p21 and HSP-70, which facilitate survival. HDAC inhibitors can act on other neural cell types in the central nervous system, such as reactive astrocytes and microglia, to reduce inflammation and secondary damage during neuronal injury or disease. HDAC inhibition is a promising therapeutic approach for the treatment of a range of central nervous system disorders (Langley B et al., 2005, Current Drug Targets—CNS & Neurological Disorders, 4: 41-50).

Histone deacetylase is known to play an essential role in the transcriptional machinery for regulating gene expression, induce histone hyperacetylation and to affect the gene expression. Therefore, it is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc. Thus, there remains a need for the development of novel inhibitors of histone deacetylases and tubulin histone deacetylases. In particular, inhibitors that are more potent and/or more specific for their particular target than known HDAC and TDAC inhibitors. HDAC inhibitors specific for a certain class or member of the HDAC family would be particularly useful both in the treatment of proliferative diseases and protein deposition disorders and in the study of HDACs, particularly HDAC6. Inhibitors that are specific for HDAC versus TDAC and vice versa are also useful in treating disease and probing biological pathways. The present invention provides novel compounds, pharmaceutical compositions thereof, and methods of using these compounds to treat disorders related to HDAC6 including cancers, inflammatory, autoimmune, neurological and neurodegenerative disorders.

SUMMARY OF THE INVENTION

In one aspect, the invention provides a compound of formula I:

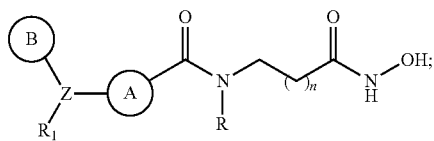

or a pharmaceutically acceptable salt, ester or prodrug thereof,
wherein,
Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;
ring B is an optionally substituted aryl or an optionally substituted heteroaryl;
$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;
or ring B and $R_1$ may together with the atom to which each is attached, form an optionally substituted heterocyclic, or an optionally substituted heteroaryl;
or R* and $R_1$ together with the atom to which each is attached, may form an optionally substituted carbocyclic, optionally substituted heterocyclic, optionally substituted aryl or optionally substituted heteroaryl ring;
R is H or an optionally substituted alkyl; or R and ring A may be joined to form a fused bicyclic ring which may be optionally substituted;
each $R_2$ is independently alkyl, cycloalkyl, heterocycloalkyl, aryl, or heteroaryl, each of which is optionally substituted;
each $R_3$ is independently alkyl, cycloalkyl, heterocycloalkyl, aryl, or heteroaryl, each of which is optionally substituted;
n is 4, 5, 6, 7 or 8; and
p is 0, 1, or 2.

In another aspect, the invention provides a pharmaceutical composition comprising a compound of formula I, or a pharmaceutically acceptable ester, salt, or prodrug thereof, together with a pharmaceutically acceptable carrier.

In one aspect, the invention provides a method of inhibiting a histone deacetylase (HDAC) in a subject, comprising administering a compound of formula I

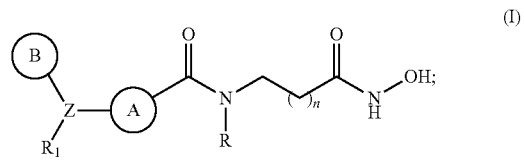

or a pharmaceutically acceptable salt, ester or prodrug thereof,
wherein,
Z is N or CR*, wherein R* is an optionally substituted alkyl, an optionally substituted acyl, an optionally substituted aryl or an optionally substituted heteroaryl;
ring A is an optionally substituted aryl or an optionally substituted heteroaryl;
ring B is an optionally substituted aryl or an optionally substituted heteroaryl;
$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;
or ring B and $R_1$ may together with the atom to which each is attached, form an optionally substituted heterocyclic, or an optionally substituted heteroaryl;
or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In another aspect, the invention provides a method of treating a disease mediated by HDAC-6 in a subject comprising administering to the subject a compound of formula I

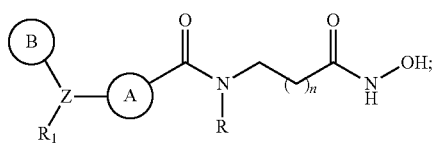

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In other aspects, the invention provides a method of treating a subject suffering from or susceptible to multiple myeloma comprising administering to a subject in need thereof a therapeutically effective amount of a compound of formula I,

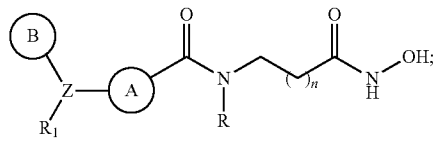

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2;

to thereby treat the subject suffering from or susceptible to multiple myeloma.

In another aspect, the invention provides a kit comprising a compound capable of inhibiting HDAC activity selected from one or more compounds of formula I

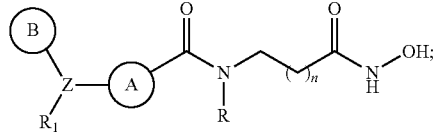

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2;

and instructions for use in treating multiple myeloma.

DETAILED DESCRIPTION OF THE INVENTION

Definitions

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon moieties containing, in certain embodiments, between one and six, or one and eight carbon atoms, respectively. Examples of $C_1$-$C_6$ alkyl moieties include, but are not limited to, methyl, ethyl, propyl, isopropyl, n-butyl, tert-butyl, neopentyl, n-hexyl moieties; and examples of $C_1$-$C_8$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl moiety.

The term "aryl," as used herein, refers to a mono- or polycyclic carbocyclic ring system having one or more aromatic rings, fused or non-fused, including, but not limited to, phenyl, naphthyl, tetrahydronaphthyl, indanyl, idenyl and the like.

The term "aralkyl," or "arylalkyl," as used herein, refers to an alkyl residue attached to an aryl ring. Examples include, but are not limited to, benzyl, phenethyl and the like.

The term "carbocyclic," as used herein, denotes a monovalent group derived from a monocyclic or polycyclic saturated, partially unsaturated, or fully unsaturated carbocyclic ring compound. Examples of carbocyclic groups include groups found in the cycloalkyl definition and aryl definition.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, moieties or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "hal," "halo" and "halogen," as used herein, refer to an atom selected from fluorine, chlorine, bromine and iodine.

The term "oxo" as used herein, refers to an oxygen that is attached to a carbon, preferably by a double bond (e.g., carbonyl).

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl, arylalkyl, heteroarylalkyl, —F, —Cl, —Br, —I, —OH, protected hydroxy, oxygen, oxo,

—NO$_2$, —CN,

—NH$_2$, protected amino, —NH—C$_1$-C$_{12}$-alkyl, —NH-aryl, -dialkylamino, —O—C$_1$-C$_{12}$-alkyl, —O-aryl,

—C(O)—, —C(O)O—, —C(O)NH—, —OC(O)—, —OC(O)O—, —OC(O)NH—, —NHC(O)—, —NHC(O)O—,

—C(O)—C$_1$-C$_{12}$-alkyl, —C(O)—C$_3$-C$_{12}$-cycloalkyl, —C(O)-aryl, —C(O)-heteroaryl, —C(O)—heterocycloalkyl, —C(O)O—C$_1$-C$_{12}$-alkyl, —C(O)O—C$_3$-C$_{12}$-cycloalkyl, —C(O)O-aryl, —C(O)O-heteroaryl, —C(O)O-heterocycloalkyl, —CONH$_2$, —CONH—C$_1$-C$_{12}$-alkyl, —CONH-aryl, —OCO$_2$—C$_1$-C$_{12}$-alkyl, —OCO$_2$-aryl, —OCONH$_2$, —OCONH—C$_1$-C$_{12}$-alkyl, —OCONH-aryl, —NHC(O)—C$_1$-C$_{12}$-alkyl, —NHC(O)-aryl, —NHCO$_2$—C$_1$-C$_{12}$-alkyl, —NHCO$_2$-aryl, —S(O)—C$_1$-C$_{12}$-alkyl, —S(O)-aryl, —SO$_2$NH—C$_1$-C$_{12}$-alkyl, —SO$_2$NH-aryl, —NHSO$_2$—C$_1$-C$_{12}$-alkyl, —NHSO$_2$-aryl, —SH, —S—C$_1$-C$_{12}$-alkyl, or —S-aryl.

In certain embodiments, the optionally substituted groups include the following: cycloalkyl, C$_3$-C$_{12}$-alkyl, C$_2$-C$_{12}$-alkenyl, C$_2$-C$_{12}$-alkynyl, C$_3$-C$_{12}$-aryl, C$_3$-C$_{12}$-heterocycloalkyl, C$_3$-C$_{12}$-heteroaryl, C$_4$-C$_{12}$-arylalkyl, or C$_2$-C$_{12}$-heteroarylalkyl.

It is understood that the aryls, heteroaryls, alkyls, and the like can be further substituted.

As used herein, the term "metal chelator" refers to any molecule or moiety that is capable of forming a complex (i.e., "chelates") with a metal ion. In certain exemplary embodiments, a metal chelator refers to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, Ca$^{2+}$, Fe$^{3+}$, Zn$^{2+}$, Na$^{30}$, etc. In certain embodiments, the metal chelator binds Zn$^{2+}$. In certain embodiments, molecules of moieties that precipitate metal ions are not considered to be metal chelators.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. In certain other preferred embodiments, natural-product-like small molecules are utilized.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

Compounds of the Invention

In one aspect, the invention provides a compound of formula I:

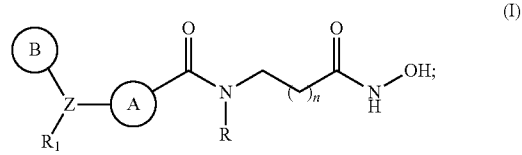

or a pharmaceutically acceptable salt, ester or prodrug thereof,
wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In one embodiment, the ring A is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In another embodiment, the ring B is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In certain embodiments, $R_1$ is H, optionally substituted alkyl, optionally substituted aryl, or optionally substituted heteroaryl, or $R_1$ is OH or alkoxy.

In a further embodiment, $R_1$ is H, methyl, ethyl, propyl, i-propyl, butyl, i-butyl, t-butyl, pentyl, hexyl, phenyl, naphthyl, pyridinyl, OH, $OCH_3$, $OCH_2CH_3$, O—Pr, O-iPr, O-Bu, O-sBu, or O-tBu; each of which may be optionally substituted.

In various embodiments, $R_1$ is OH, alkoxy, $NH_2$, NH(alkyl), N(alkyl)(alkyl), NH-aryl, NH-hetroaryl, N(aryl)(aryl), N(aryl)(heteroaryl), or N(heteroaryl)(heteroaryl).

In other embodiments, the carbonyl and the Z group attached to ring A are disposed para to each other.

In other embodiments, the carbonyl and Z group attached to ring A are disposed meta to each other.

In another embodiment, the carbonyl and the Z group attached to ring A are disposed ortho to each other.

In one embodiment, the invention provides a compound formula II:

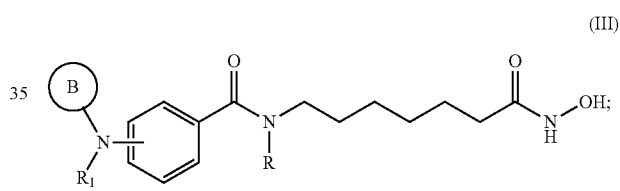

(II)

or a pharmaceutically acceptable salt, ester or prodrug thereof, wherein, each of $X_1$, $X_2$, $X_3$, or $X_4$ is independently N, CR', O, S, NCR', CR'CR', OCR', SCR', or absent, or $X_1$ or $X_4$ may be joined with R to form a bicyclic ring; wherein up to three of $X_1$, $X_2$, $X_3$, or $X_4$ may be N;

ring B is an optionally substituted aryl or an optionally substituted heteroaryl;

$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;

R is H or an optionally substituted alkyl; or R and $X_1$ or $X_4$ may be joined to form a fused bicyclic ring which may be optionally substituted;

each R' is independently H, optionally substituted alkyl, halo, OH, $NH_2$, NHR", haloalkyl, CN, $N_3$, $NO_2$;

R" is H or alkyl; and $R_2$ is alkyl, cycloalkyl, heterocycloalkyl, aryl, or heteroaryl, each of which is optionally substituted.

In certain embodiments, $X_1$, $X_2$, $X_3$, and $X_4$ are all CR'.

In other embodiments, $X_2$ and $X_3$, are N and $X_1$ and $X_4$ are CR'.

In another embodiment, $X_2$ and $X_3$, are CR' and $X_1$ and $X_4$ are N.

In still other embodiments, $X_2$, is N; $X_3$ is S, N or O; $X_1$ is CR' and $X_4$ is absent.

In one embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, hal, OH, $NH_2$, NHR", CN, $N_3$, or $NO_2$.

In certain embodiments, $R_1$ is H, alkyl, aryl, arylalkyl, or heteroaryl, each of which may be optionally substituted.

In another embodiment, the invention provides a compound of formula III:

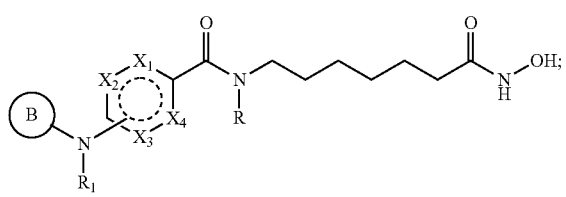

(III)

or a pharmaceutically acceptable salt, ester or prodrug thereof, wherein, ring B is an optionally substituted aryl or an optionally substituted heteroaryl;

$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;

$R_2$ is optionally substituted heteroaryl, and

R is H or an optionally substituted alkyl; or R and the phenyl ring may be joined to form a fused [6,5] bicyclic ring which may be optionally substituted.

In one embodiment, ring B is phenyl, pyridinyl, pyrimidinyl, or pyrazinyl; each of which may be optionally substituted.

In a further embodiment, ring B is substituted by alkyl, aryl, aralkyl, haloalkyl, hal, OH, $NH_2$, CN, or $NO_2$.

In other embodiments, $R_1$ is H, alkyl, aryl, arylalkyl, heteroaryl, C(O)—$R_2$, or C(O)O—$R_2$, each of which may be optionally substituted.

In various embodiments, $R_2$ is optionally substituted pyridinyl.

In another embodiment, the invention provides a compound of formula IV:

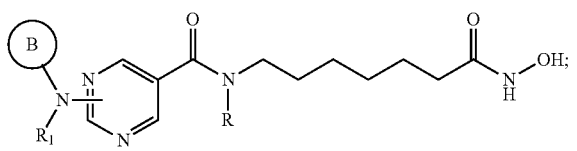

(IV)

or a pharmaceutically acceptable salt, ester or prodrug thereof,
wherein,
ring B is an optionally substituted aryl or an optionally substituted heteroaryl;
$R_1$ is H, alkyl, haloalkyl, alkenyl, aryl, arylalkyl, heteroaryl, heterocyclic, or carbocyclic, each of which may be optionally substituted;
or ring B and $R_1$ may together with the atom to which each is attached, form an optionally substituted heterocyclic, or an optionally substituted heteroaryl, and
R is H or an optionally substituted alkyl; or R and the 1,3-pyrimidinyl ring may be joined to form a fused bicyclic ring which may be optionally substituted.

In certain embodiments, ring B is phenyl, pyridinyl, pyrimidinyl, or pyrazinyl; each of which may be optionally substituted.

In a further embodiment, ring B is substituted by alkyl, aryl, aralkyl, haloalkyl, halo, OH, $NH_2$, CN, or $NO_2$.

In other embodiments, $R_1$ is H, alkyl, aryl, arylalkyl, or heteroaryl, each of which may be optionally substituted.

In another embodiment, $R_1$ is substituted by OH or halo.

In certain embodiments, the ring formed by ring B and $R_1$ is piperidine, pyrrolidine, tetrahydroquinoline, morpholine, piperazine, tetrahydro-triazolo pyrazine, or diazepane, each of which is optionally substituted.

In another embodiment, the invention provides a compound of formula V:

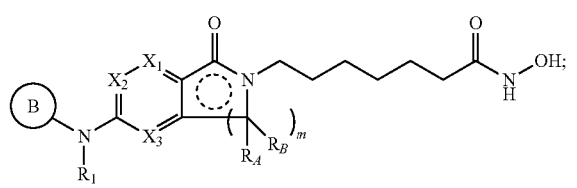

(V)

or a pharmaceutically acceptable salt, ester or prodrug thereof,
wherein,
each of $X_1$, $X_2$, or $X_3$ is independently N or CR';
ring B is an optionally substituted aryl or an optionally substituted heteroaryl;
$R_1$ is H, alkyl, haloalkyl, alkenyl, aryl, arylalkyl, heteroaryl, heterocyclic, or carbocyclic, each of which may be optionally substituted;
each $R_A$ and $R_B$ is independently H, $NH(R_C)$, $N(R_C)(R_C)$, $N(R_C)CO(R_C)$, $CO_2H$, $C(O)R_C$, $C(O)OR_C$, $C(O)NH_2$, $C(O)NH(R_C)$, $C(O)N(R_C)(R_C)$, $SO_2R_C$, $SOR_C$, $SR_C$, alkyl, aryl, arylalkyl, alkoxy, heteroaryl, heterocyclic, and carbocyclic, each of which may be further substituted; or $R_A$ and $R_B$ together with the carbon to which they are attached form a carbonyl;

each $R_C$ is independently H, alkyl, alkenyl, aryl, heteroaryl, cycloalkyl, or heterocyclic, each of which may be further substituted;
R' is H, optionally substituted alkyl, halo, OH, $NH_2$, NHR", haloalkyl, CN, $N_3$, $NO_2$;
R" is H or alkyl; and
m is 1 or 2.

In a related embodiment, the invention provides a compound of formula Va:

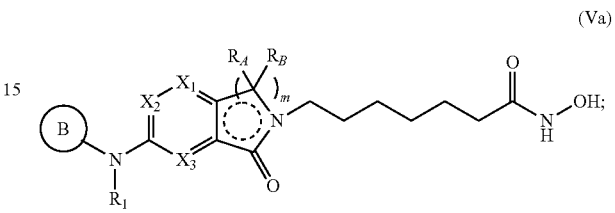

(Va)

or a pharmaceutically acceptable salt, ester or prodrug thereof,
wherein,
each of $X_1$, $X_2$, or $X_3$ is independently N or CR';
ring B is an optionally substituted aryl or an optionally substituted heteroaryl;
$R_1$ is H, alkyl, haloalkyl, alkenyl, aryl, arylalkyl, heteroaryl, heterocyclic, or carbocyclic, each of which may be optionally substituted;
each $R_A$ and $R_B$ is independently H, $NH(R_C)$, $N(R_C)(R_C)$, $N(R_C)CO(R_C)$, $CO_2H$, $C(O)R_C$, $C(O)OR_C$, $C(O)NH_2$, $C(O)NH(R_C)$, $C(O)N(R_C)(R_C)$, $SO_2R_C$, $SOR_C$, $SR_C$, alkyl, aryl, arylalkyl, alkoxy, heteroaryl, heterocyclic, and carbocyclic, each of which may be further substituted; or $R_A$ and $R_B$ together with the carbon to which they are attached form a carbonyl;
each $R_C$ is independently H, alkyl, alkenyl, aryl, heteroaryl, cycloalkyl, or heterocyclic, each of which may be further substituted;
R' is H, optionally substituted alkyl, halo, OH, $NH_2$, NHR", haloalkyl, CN, $N_3$, $NO_2$;
R" is H or alkyl; and
m is 1 or 2.

In one embodiment, $X_1$, $X_2$, and $X_3$, are all independently CR'.

In another embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, halo, OH, $NH_2$, NHR", CN, $N_3$, or $NO_2$.

In certain embodiments, $R_1$ is H, alkyl, aryl, arylalkyl, or heteroaryl, each of which may be optionally substituted.

In another embodiment, the invention provides a compound of formula VI:

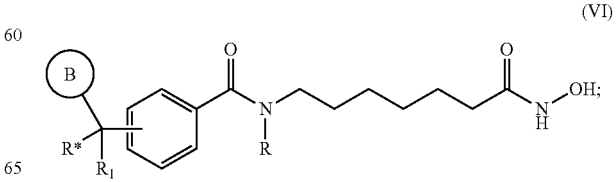

(VI)

or a pharmaceutically acceptable salt, ester or prodrug thereof,
wherein,
ring B is an optionally substituted aryl or an optionally substituted heteroaryl;
R* is an optionally substituted alkyl, an optionally substituted aryl or an optionally substituted heteroaryl;
$R_1$ is H, alkyl, aryl, arylalkyl, heteroaryl, heterocyclic, carbocyclic, OH, alkoxy, $NH_2$, NH(alkyl), or N(alkyl)(alkyl);
or R* and $R_1$ together with the atom to which each is attached, may form an optionally substituted carbocyclic, optionally substituted heterocyclic, optionally substituted aryl or optionally substituted heteroaryl ring; and
R is H or an optionally substituted alkyl.
In one embodiment, ring B is phenyl, pyridinyl, pyrimidinyl, pyrazinyl, or thiazole; each of which may be optionally substituted.

In another embodiment, R* is methyl, trifluoromethyl, phenyl, pyridinyl, pyrimidinyl, pyrazinyl, or thiazole; each of which may be optionally substituted.

In certain embodiments, $R_1$ is OH, methoxy, or ethoxy.

In various embodiments, ring B and R* are each independently substituted with one or more of alkyl, halogen, or $C(O)NR_XR_Y$, wherein $R_X$ is H or alkyl, and $R_Y$ is H or alkyl.

In other embodiments, ring B and R* are each independently substituted with one or more of methyl, F, or $C(O)N(Me)_2$.

In another aspect, the invention provides a pharmaceutical composition comprising a compound of formula I, or a pharmaceutically acceptable ester, salt, or prodrug thereof, together with a pharmaceutically acceptable carrier.

Representative compounds of the invention include, but are not limited to, the following compounds of Table 1 below.

TABLE 1

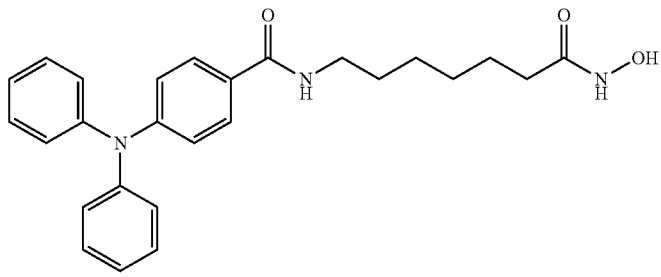 [SMILES: O=C(CCCCCCNC(=O)c1ccc(N(c2ccccc2)c2ccccc2)cc1)NO]

4-(diphenylamino)-N-(7-(hydroxyamino)-7-oxoheptyl)benzamide
$IC_{50}$(nM) HDAC6 = 18 HDAC3 = 316

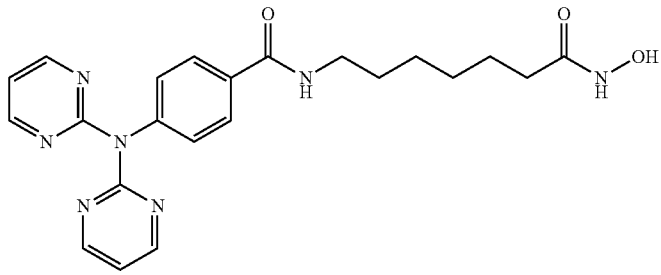 [SMILES: O=C(CCCCCCNC(=O)c1ccc(N(c2ncccn2)c2ncccn2)cc1)NO]

4-(dipyrimidin-2-ylamino)-N-(7-(hydroxyamino)-7-oxoheptyl)benzamide
$IC_{50}$(nM) HDAC6 = 174 HDAC3 = 1089

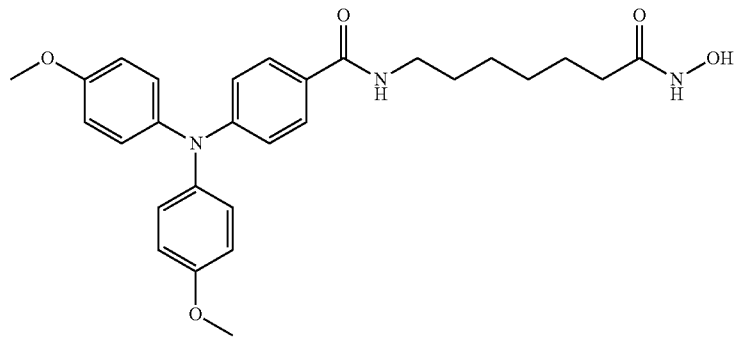 [SMILES: COc1ccc(N(c2ccc(OC)cc2)c2ccc(C(=O)NCCCCCCC(=O)NO)cc2)cc1]

4-(bis(4-methoxyphenyl)amino)-N-(7-(hydroxyamino)-7-oxoheptyl)benzamide
$IC_{50}$(nM) HDAC6 = 200 HDAC3 = 2001

TABLE 1-continued

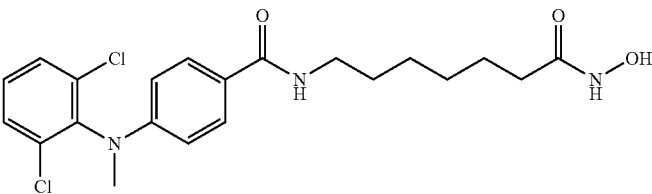 [SMILES: CN(c1ccc(C(=O)NCCCCCCC(=O)NO)cc1)c1c(Cl)cccc1Cl]

4-((2,6-dichlorophenyl)(methyl)amino)-N-(7-
(hydroxyamino)-7-oxoheptyl)benzamide
IC$_{50}$(nM) HDAC6 = 3 HDAC3 = 29

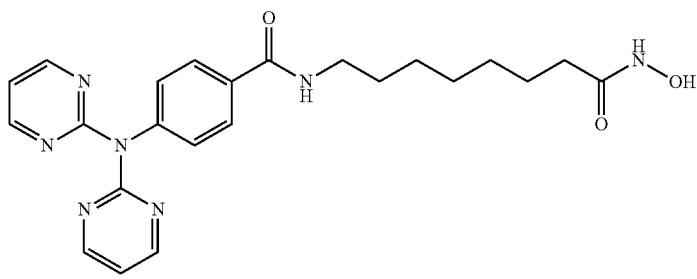 [SMILES: O=C(CCCCCCCNC(=O)c1ccc(N(c2ncccn2)c2ncccn2)cc1)NO]

4-(dipyrimidin-2-ylamino)-N-(8-
(hydroxyamino)-8-oxooctyl)benzamide
IC$_{50}$(nM) HDAC6 = 110 HDAC3 = 208

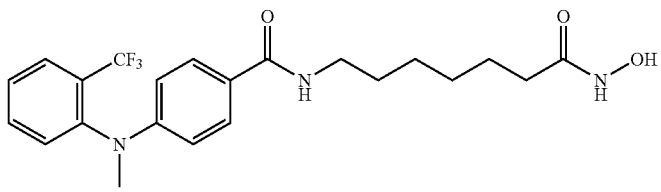 [SMILES: CN(c1ccc(C(=O)NCCCCCCC(=O)NO)cc1)c1ccccc1C(F)(F)F]

N-(7-(hydroxyamino)-7-oxoheptyl)-4-
(methyl(2-(trifluoromethyl)phenyl)
amino)benzamide
IC$_{50}$(nM) HDAC6 = 3 HDAC3 = 36

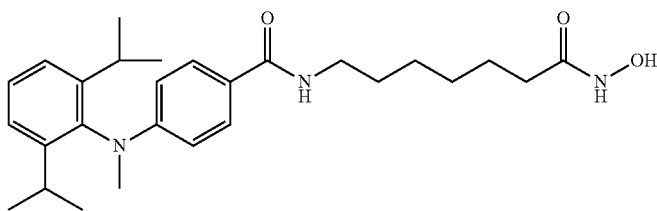 [SMILES: CC(C)c1cccc(C(C)C)c1N(C)c1ccc(C(=O)NCCCCCCC(=O)NO)cc1]

4-((2,6-diisopropylphenyl)(methyl)amino)-N-
(7-(hydroxyamino)-7-oxoheptyl)benzamide
IC$_{50}$(nM) HDAC6 = 45 HDAC3 = 1074

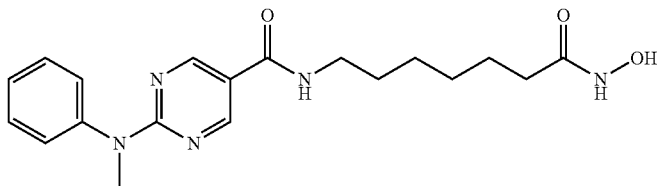 [SMILES: CN(c1ccccc1)c1ncc(C(=O)NCCCCCCC(=O)NO)cn1]

N-(7-(hydroxyamino)-7-oxoheptyl)-2-
(methyl(phenyl)amino)pyrimidine-5-
carboxamide
IC$_{50}$(nM) HDAC6 = 6 HDAC3 = 47

TABLE 1-continued

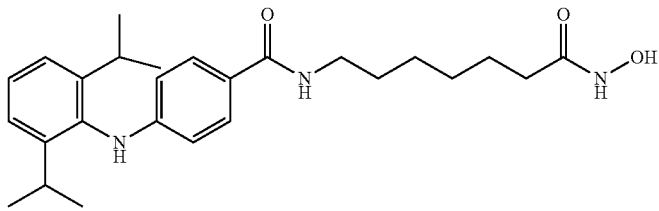 [SMILES: CC(C)c1cccc(C(C)C)c1Nc1ccc(C(=O)NCCCCCCC(=O)NO)cc1]

4-(2,6-diisopropylphenylamino)-N-(7-
(hydroxyamino)-7-oxoheptyl)benzamide
IC$_{50}$(nM) HDAC6 = 20 HDAC3 = 369

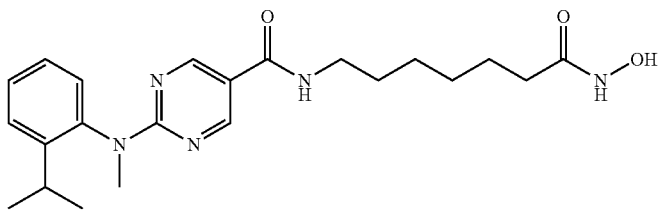 [SMILES: CC(C)c1ccccc1N(C)c1ncc(C(=O)NCCCCCCC(=O)NO)cn1]

N-(7-(hydroxyamino)-7-oxoheptyl)-2-((2-
isopropylphenyl)(methyl)amino)pyrimidine-
5-carboxamide
IC$_{50}$(nM) HDAC6 = 7 HDAC3 = 73

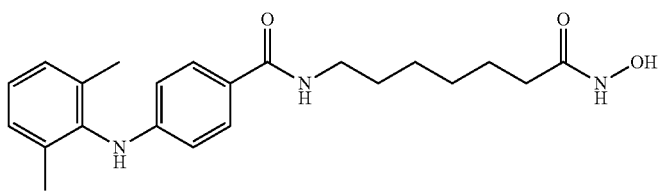 [SMILES: Cc1cccc(C)c1Nc1ccc(C(=O)NCCCCCCC(=O)NO)cc1]

4-(2,6-dimethylphenylamino)-N-(7-
(hydroxyamino)-7-oxoheptyl)benzamide
IC$_{50}$(nM) HDAC6 = 3 HDAC3 = 59

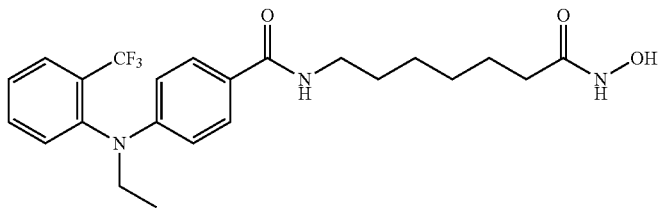 [SMILES: CCN(c1ccc(C(=O)NCCCCCCC(=O)NO)cc1)c1ccccc1C(F)(F)F]

4-(ethyl(2-(trifluoromethyl)phenyl)amino)-N-
(7-(hydroxyamino)-7-oxoheptyl) benzamide
IC$_{50}$(nM) HDAC6 = 5 HDAC3 = 46

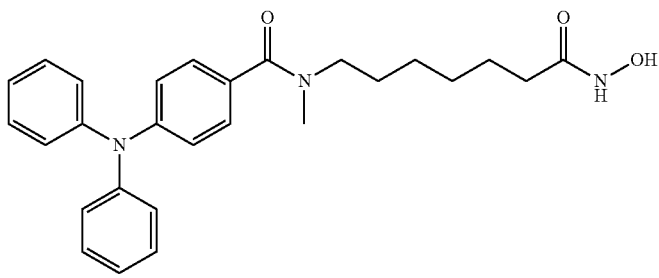 [SMILES: CN(CCCCCCC(=O)NO)C(=O)c1ccc(N(c2ccccc2)c2ccccc2)cc1]

4-(diphenylamino)-N-(7-(hydroxyamino)-7-
oxoheptyl)-N-methylbenzamide
IC$_{50}$(nM) HDAC6 = 82 HDAC3 = 313

TABLE 1-continued

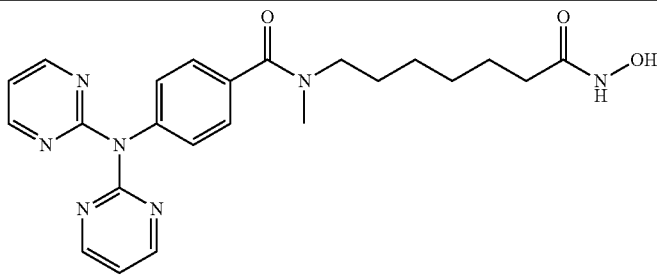

4-(dipyrimidin-2-ylamino)-N-(7-
(hydroxyamino)-7-oxoheptyl)-N-
methylbenzamide
IC$_{50}$(nM) HDAC6 = 198 HDAC3 = 1237

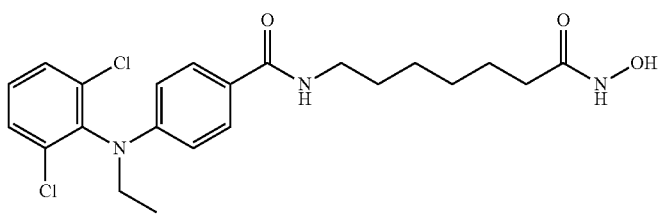 [SMILES: CCN(c1ccc(C(=O)NCCCCCCC(=O)NO)cc1)c1c(Cl)cccc1Cl]

4-((2,6-dichlorophenyl)(ethyl)amino)-N-(7-
(hydroxyamino)-7-oxoheptyl)benzamide
IC$_{50}$(nM) HDAC6 = 8 HDAC3 = 71

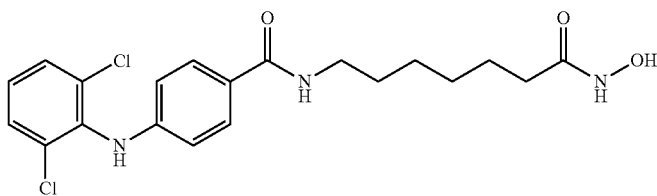 [SMILES: O=C(CCCCCCNC(=O)c1ccc(Nc2c(Cl)cccc2Cl)cc1)NO]

4-(2,6-dichlorophenylamino)-N-(7-
(hydroxyamino)-7-oxoheptyl)benzamide
IC$_{50}$(nM) HDAC6 = 3 HDAC3 = 28

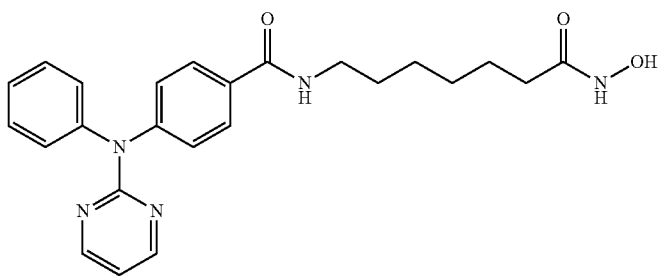

N-(7-(hydroxyamino)-7-oxoheptyl)-4-
(phenyl(pyrimidin-2-yl)amino)benzamide
IC$_{50}$(nM) HDAC6 = 3 HDAC3 = 65

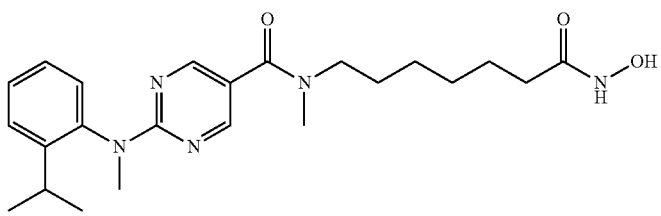 [SMILES: CC(C)c1ccccc1N(C)c1ncc(C(=O)N(C)CCCCCCC(=O)NO)cn1]

N-(7-(hydroxyamino)-7-oxoheptyl)-2-((2-
isopropylphenyl)(methyl)amino)-N-
methylpyrimidine-5-carboxamide
IC$_{50}$(nM) HDAC6 = 50 HDAC3 = 642

TABLE 1-continued

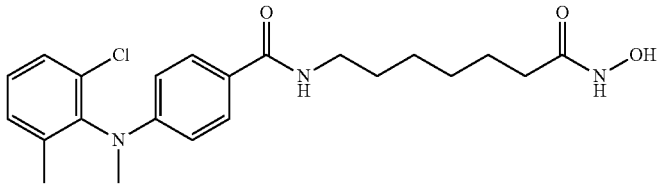 [SMILES: Cc1cccc(Cl)c1N(C)c1ccc(C(=O)NCCCCCCC(=O)NO)cc1]

4-((2-chloro-6-methylphenyl)(methyl) amino)-
N-(7-(hydroxyamino)-7-oxoheptyl) benzamide
IC$_{50}$(nM) HDAC6 = 4 HDAC3 = 58

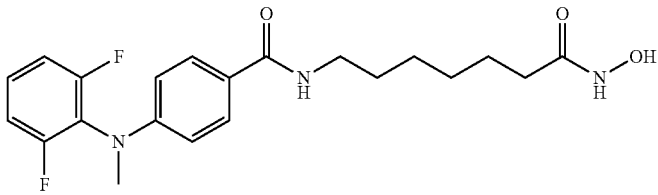 [SMILES: CN(c1ccc(C(=O)NCCCCCCC(=O)NO)cc1)c1c(F)cccc1F]

4-((2,6-difluorophenyl)(methyl)amino)-N-(7-
(hydroxyamino)-7-oxoheptyl) benzamide
IC$_{50}$(nM) HDAC6 = 2 HDAC3 = 17

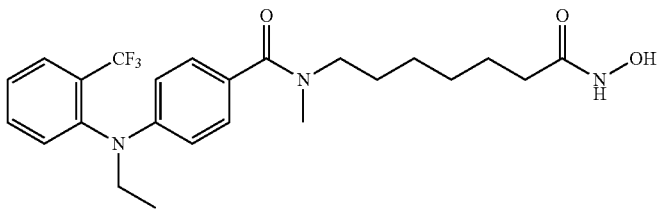 [SMILES: CCN(c1ccc(C(=O)N(C)CCCCCCC(=O)NO)cc1)c1ccccc1C(F)(F)F]

4-(ethyl(2-(trifluoromethyl)phenyl)amino)-N-
(7-(hydroxyamino)-7-oxoheptyl)-N-
methylbenzamide
IC$_{50}$(nM) HDAC6 = 39 HDAC3 = 58

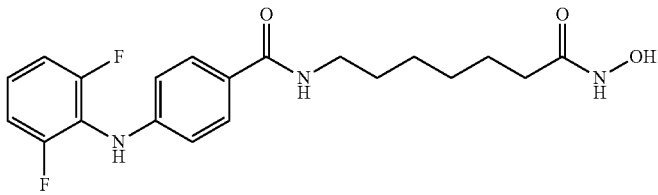 [SMILES: O=C(CCCCCCNC(=O)c1ccc(Nc2c(F)cccc2F)cc1)NO]

4-(2,6-difluorophenylamino)-N-(7-
(hydroxyamino)-7-oxoheptyl)benzamide
IC$_{50}$(nM) HDAC6 = 3 HDAC3 = 25

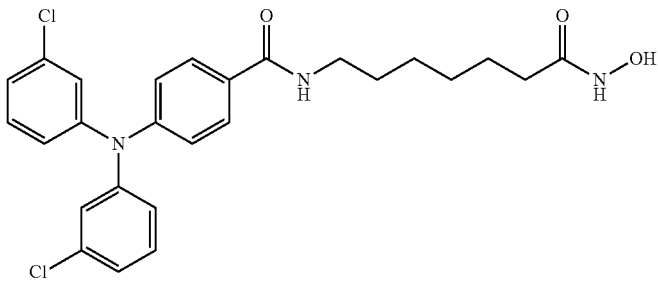 [SMILES: O=C(CCCCCCNC(=O)c1ccc(N(c2cccc(Cl)c2)c2cccc(Cl)c2)cc1)NO]

4-(bis(3-chlorophenyl)amino)-N-(7-
(hydroxyamino)-7-oxoheptyl)benzamide
IC$_{50}$(nM) HDAC6 = 858 HDAC3 = 11813

TABLE 1-continued

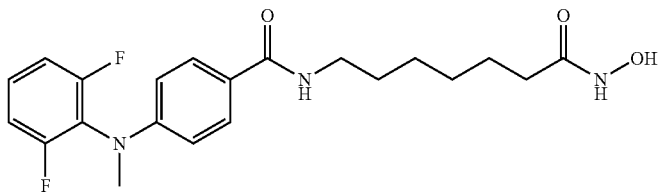 [SMILES: CN(c1ccc(C(=O)NCCCCCCC(=O)NO)cc1)c1c(F)cccc1F]

7-(4-((2,6-difluorophenyl)(methyl)
amino)benzylamino)-N-hydroxy heptanamide
IC$_{50}$(nM) HDAC6 = 121 HDAC3 = 67

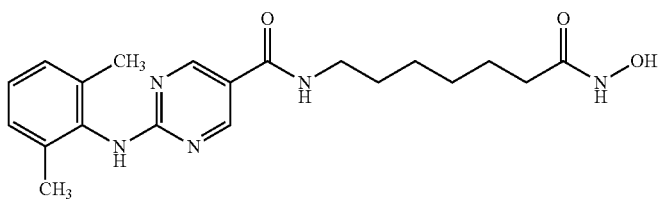 [SMILES: Cc1cccc(C)c1Nc1ncc(C(=O)NCCCCCCC(=O)NO)cn1]

2-(2,6-dimethylphenylamino)-N-(7-
(hydroxyamino)-7-oxoheptyl)pyrimidine-5-
carboxamide
IC$_{50}$(nM) HDAC6 = 33 HDAC3 = 505

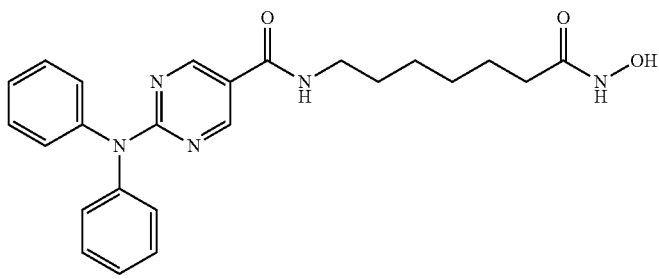 [SMILES: O=C(CCCCCCNC(=O)c1cnc(N(c2ccccc2)c2ccccc2)nc1)NO]

2-(diphenylamino)-N-(7-(hydroxyamino)-7-
oxoheptyl)pyrimidine-5-carboxamide
IC$_{50}$(nM) HDAC6 = 10 HDAC3 = 84

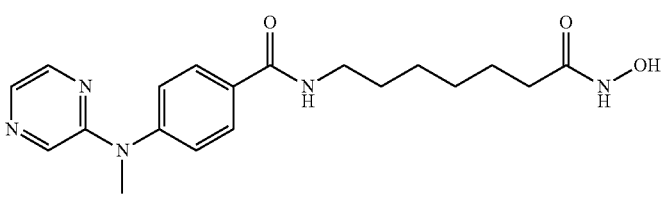 [SMILES: CN(c1ccc(C(=O)NCCCCCCC(=O)NO)cc1)c1cnccn1]

N-(7-(hydroxyamino)-7-oxoheptyl)-4-
(methyl(pyrazin-2-yl)amino)benzamide
IC$_{50}$(nM) HDAC6 = 21 HDAC3 = 93

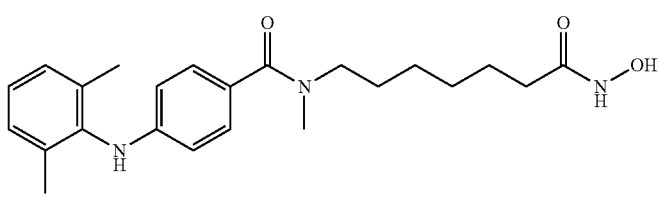 [SMILES: Cc1cccc(C)c1Nc1ccc(C(=O)N(C)CCCCCCC(=O)NO)cc1]

4-(2,6-dimethylphenylamino)-N-(7-
(hydroxyamino)-7-oxoheptyl)-N-
methylbenzamide
IC$_{50}$(nM) HDAC6 = 7 HDAC3 = 304

TABLE 1-continued

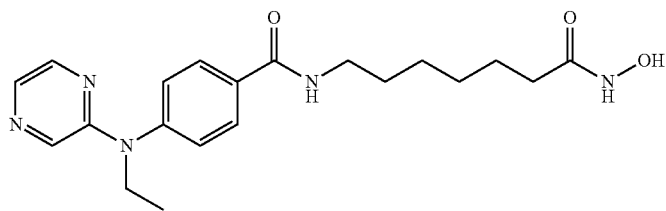 [SMILES: CCN(c1ccc(C(=O)NCCCCCCC(=O)NO)cc1)c1cnccn1]

4-(ethyl(pyrazin-2-yl)amino)-N-(7-
(hydroxyamino)-7-oxoheptyl)benzamide
IC$_{50}$(nM) HDAC6 = 11 HDAC3 = 93

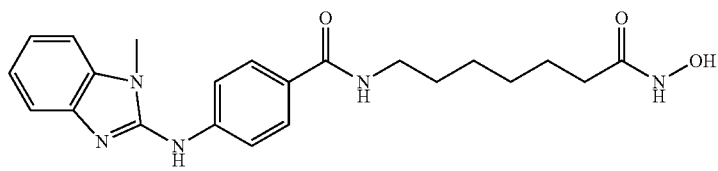 [SMILES: Cn1c(Nc2ccc(C(=O)NCCCCCCC(=O)NO)cc2)nc2ccccc21]

N-(7-(hydroxyamino)-7-oxoheptyl)-4-(1-
methyl-1H-benzo[d]imidazol-2-
ylamino)benzamide
IC$_{50}$(nM) HDAC6 = 9 HDAC3 = 57

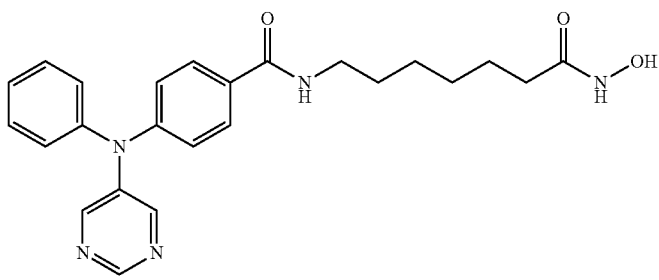

N-(7-(hydroxyamino)-7-oxoheptyl)-4-
(phenyl(pyrimidin-5-yl)amino)benzamide
IC$_{50}$(nM) HDAC6 = 12 HDAC3 = 92

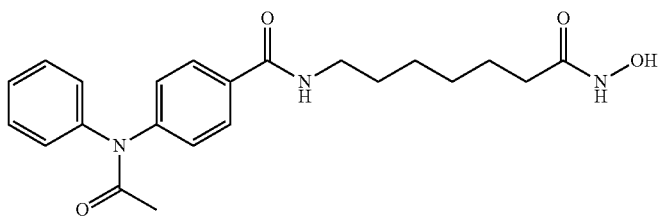 [SMILES: CC(=O)N(c1ccccc1)c1ccc(C(=O)NCCCCCCC(=O)NO)cc1]

N-(7-(hydroxyamino)-7-oxoheptyl)-4-(N-
phenylacetamido)benzamide
IC$_{50}$(nM) HDAC6 = 3 HDAC3 = 67

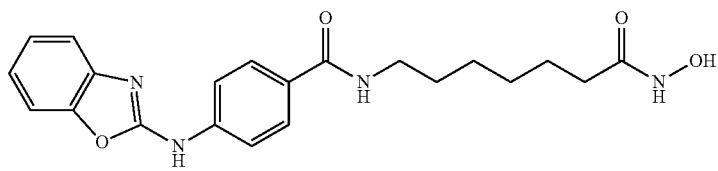 [SMILES: O=C(CCCCCCNC(=O)c1ccc(Nc2nc3ccccc3o2)cc1)NO]

4-(benzo[d]oxazol-2-ylamino)-N-(7-
(hydroxyamino)-7-oxoheptyl)benzamide
IC$_{50}$(nM) HDAC6 = 3 HDAC3 = 22

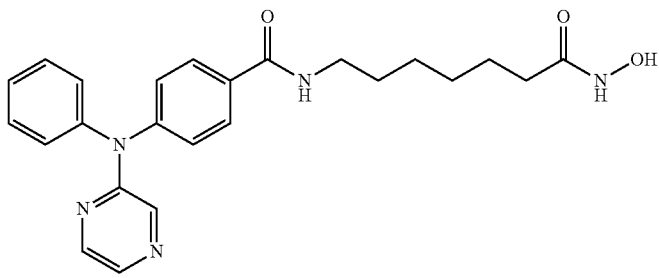 [SMILES: O=C(CCCCCCNC(=O)c1ccc(N(c2ccccc2)c2cnccn2)cc1)NO]
N-(7-(hydroxyamino)-7-oxoheptyl)-4-
(phenyl(pyrazin-2-yl)amino)benzamide
IC$_{50}$(nM) HDAC6 = 14 HDAC3 = 64
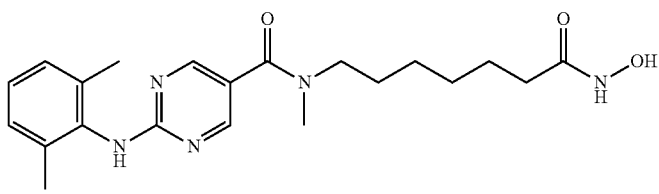 [SMILES: Cc1cccc(C)c1Nc1ncc(C(=O)N(C)CCCCCCC(=O)NO)cn1]
2-(2,6-dimethylphenylamino)-N-(7-
(hydroxyamino)-7-oxoheptyl)-N-
methylpyrimidine-5-carboxamide
IC$_{50}$(nM) HDAC6 = 33 HDAC3 = 387
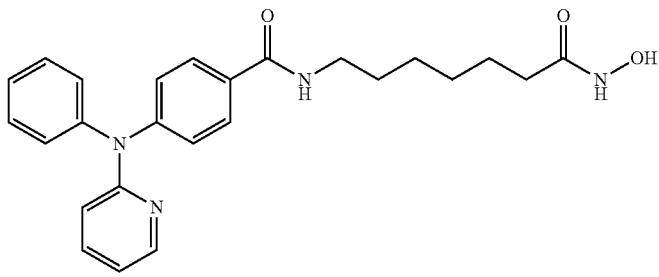 [SMILES: O=C(CCCCCCNC(=O)c1ccc(N(c2ccccc2)c2ccccn2)cc1)NO]
N-(7-(hydroxyamino)-7-oxoheptyl)-4-
(phenyl(pyridin-2-yl)amino)benzamide
IC$_{50}$(nM) HDAC6 = 14 HDAC3 = 61
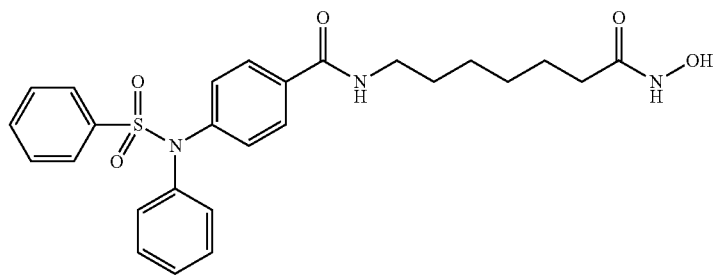 [SMILES: O=C(CCCCCCNC(=O)c1ccc(N(c2ccccc2)S(=O)(=O)c2ccccc2)cc1)NO]
N-(7-(hydroxyamino)-7-oxoheptyl)-4-(N-
phenylphenylsulfonamido)benzamide
IC$_{50}$(nM) HDAC6 = 15 HDAC3 = 84

TABLE 1-continued

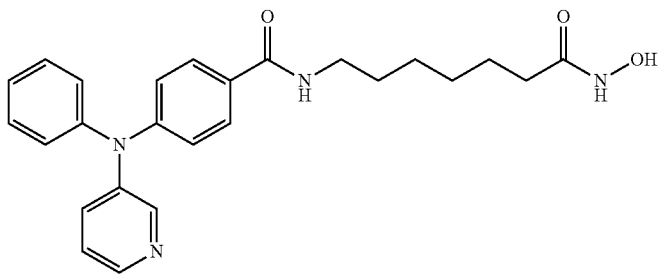 [SMILES: O=C(CCCCCCNC(=O)c1ccc(N(c2ccccc2)c2cccnc2)cc1)NO]

N-(7-(hydroxyamino)-7-oxoheptyl)-4-
(phenyl(pyridin-3-yl)amino)benzamide
IC$_{50}$(nM) HDAC6 = 21 HDAC3 = 66

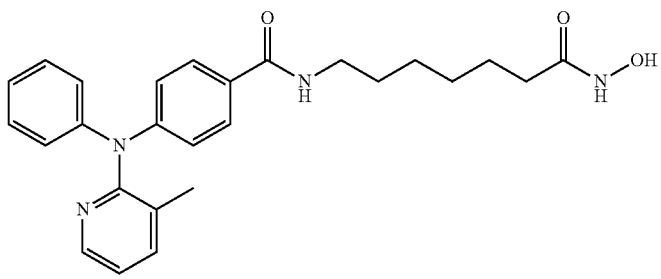 [SMILES: Cc1cccnc1N(c1ccccc1)c1ccc(C(=O)NCCCCCCC(=O)NO)cc1]

N-(7-(hydroxyamino)-7-oxoheptyl)-4-((3-
methylpyridin-2-yl)(phenyl)amino) benzamide
IC$_{50}$(nM) HDAC6 = 20 HDAC3 = 69

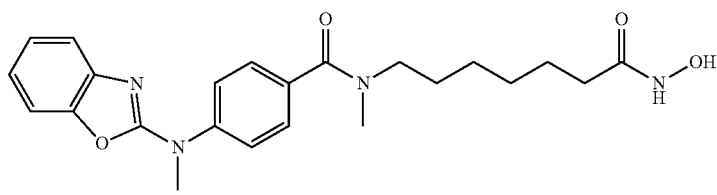

4-(benzo[d]oxazol-2-yl(methyl)amino)-N-(7-
(hydroxyamino)-7-oxoheptyl)-N-
methylbenzamide
IC$_{50}$(nM) HDAC6 = 107 HDAC3 = 294

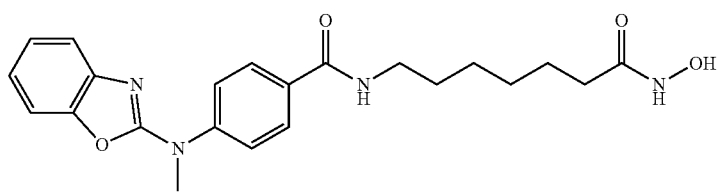 [SMILES: CN(CCCCCCC(=O)NO)C(=O)c1ccc(N(C)c2nc3ccccc3o2)cc1]

4-(benzo[d]oxazol-2-yl(methyl)amino)-N-(7-
(hydroxyamino)-7-oxoheptyl)benzamide
IC$_{50}$(nM) HDAC6 = 11 HDAC3 = 83

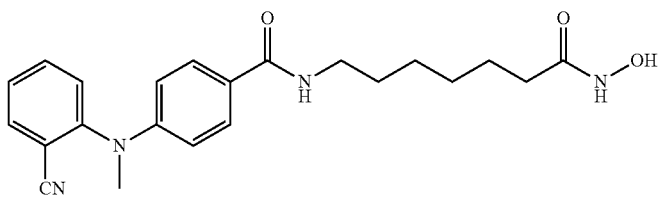 [SMILES: CN(c1ccc(C(=O)NCCCCCCC(=O)NO)cc1)c1ccccc1C#N]

4-((2-cyanophenyl)(methyl)amino)-N-(7-
(hydroxyamino)-7-oxoheptyl)benzamide
IC$_{50}$(nM) HDAC6 = 4 HDAC3 = 23

TABLE 1-continued

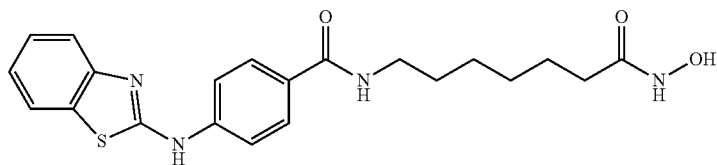

4-(benzo[d]thiazol-2-ylamino)-N-(7-
(hydroxyamino)-7-oxoheptyl)benzamide
IC50(nM) HDAC6 = 12 HDAC3 = 22

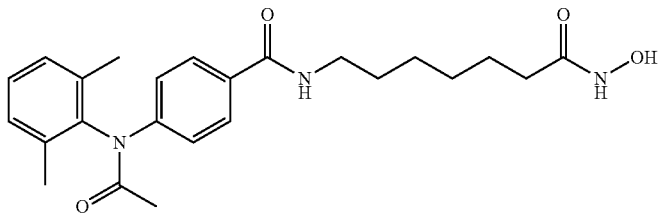 [SMILES: CC(=O)N(c1ccc(C(=O)NCCCCCCC(=O)NO)cc1)c1c(C)cccc1C]

4-(N-(2,6-dimethylphenyl)acetamido)-N-(7-
(hydroxyamino)-7-oxoheptyl) benzamide
IC$_{50}$(nM) HDAC6 = 22 HDAC3 = 198

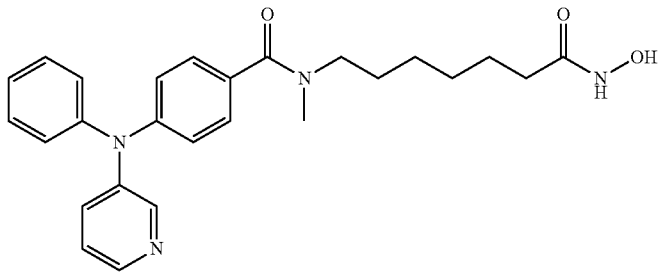 [SMILES: CN(CCCCCCC(=O)NO)C(=O)c1ccc(N(c2ccccc2)c2cccnc2)cc1]

N-(7-(hydroxyamino)-7-oxoheptyl)-N-methyl-
4-(phenyl(pyridin-3-yl)amino) benzamide
IC$_{50}$(nM) HDAC6 = 64 HDAC3 = 85

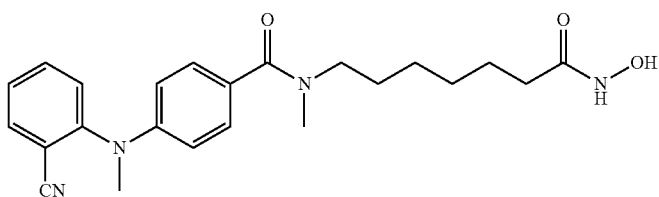 [SMILES: CN(CCCCCCC(=O)NO)C(=O)c1ccc(N(C)c2ccccc2C#N)cc1]

4-((2-cyanophenyl)(methyl)amino)-N-(7-
(hydroxyamino)-7-oxoheptyl)-N-
methylbenzamide
IC$_{50}$(nM) HDAC6 = 35 HDAC3 = 135

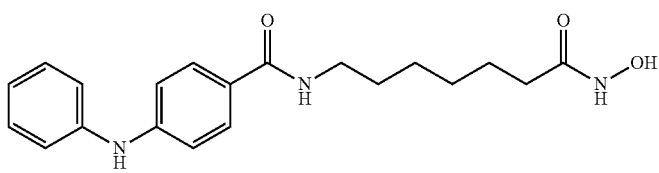 [SMILES: O=C(CCCCCCNC(=O)c1ccc(Nc2ccccc2)cc1)NO]

N-(7-(hydroxyamino)-7-oxoheptyl)-4-
(phenylamino)benzamide
IC$_{50}$(nM) HDAC6 = 7 HDAC3 = 16

TABLE 1-continued

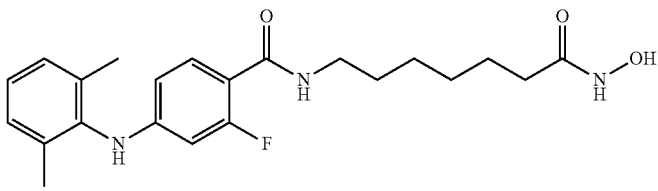 [SMILES: Cc1cccc(C)c1Nc1ccc(C(=O)NCCCCCCC(=O)NO)c(F)c1]

4-(2,6-dimethylphenylamino)-2-fluoro-N-(7-(hydroxyamino)-7-oxoheptyl) benzamide
$IC_{50}$(nM) HDAC6 = 3 HDAC3 = 95

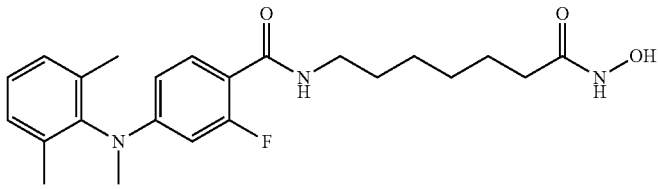 [SMILES: Cc1cccc(C)c1N(C)c1ccc(C(=O)NCCCCCCC(=O)NO)c(F)c1]

4-((2,6-dimethylphenyl)(methyl)amino)-2-fluoro-N-(7-(hydroxyamino)-7-oxoheptyl)benzamide
$IC_{50}$(nM) HDAC6 = 5 HDAC3 = 107

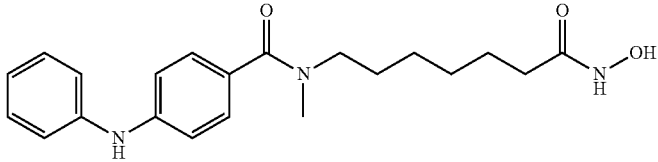 [SMILES: CN(CCCCCCC(=O)NO)C(=O)c1ccc(Nc2ccccc2)cc1]

N-(7-(hydroxyamino)-7-oxoheptyl)-N-methyl-4-(phenylamino)benzamide
$IC_{50}$(nM) HDAC6 = 11 HDAC3 = 50

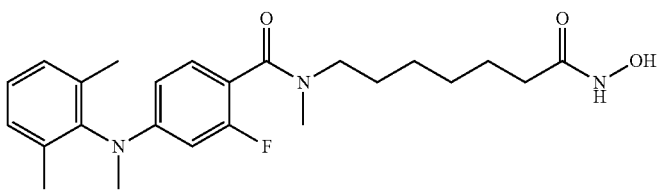 [SMILES: Cc1cccc(C)c1N(C)c1ccc(C(=O)N(C)CCCCCCC(=O)NO)c(F)c1]

4-((2,6-dimethylphenyl)(methyl)amino)-2-fluoro-N-(7-(hydroxyamino)-7-oxoheptyl)-N-methylbenzamide
$IC_{50}$(nM) HDAC6 = 9 HDAC3 = 148

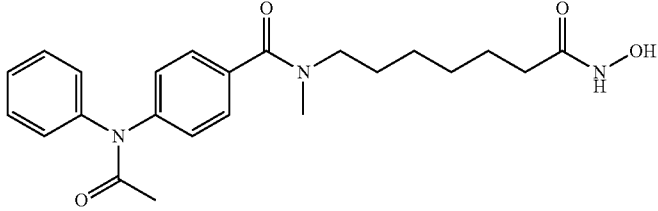 [SMILES: CC(=O)N(c1ccccc1)c1ccc(C(=O)N(C)CCCCCCC(=O)NO)cc1]

N-(7-(hydroxyamino)-7-oxoheptyl)-N-methyl-4-(N-phenylacetamido)benzamide
$IC_{50}$(nM) HDAC6 = 37 HDAC3 = 493

TABLE 1-continued

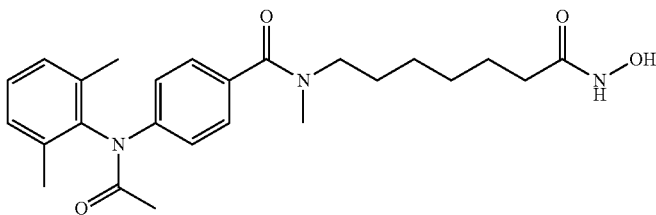 [SMILES: CC(=O)N(c1ccc(C(=O)N(C)CCCCCCC(=O)NO)cc1)c1c(C)cccc1C]

4-(N-(2,6-dimethylphenyl)acetamido)-N-(7-
(hydroxyamino)-7-oxoheptyl)-N-
methylbenzamide
IC$_{50}$(nM) HDAC6 = 25 HDAC3 = 528

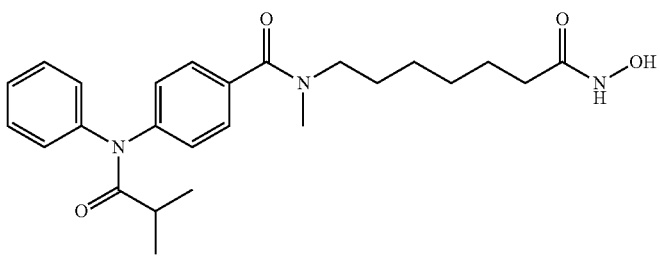 [SMILES: CC(C)C(=O)N(c1ccccc1)c1ccc(C(=O)N(C)CCCCCCC(=O)NO)cc1]

N-(7-(hydroxyamino)-7-oxoheptyl)-N-
methyl-4-(N-phenylisobutyramido)
benzamide
IC50(nM) HDAC6 = 67 HDAC3 = 533

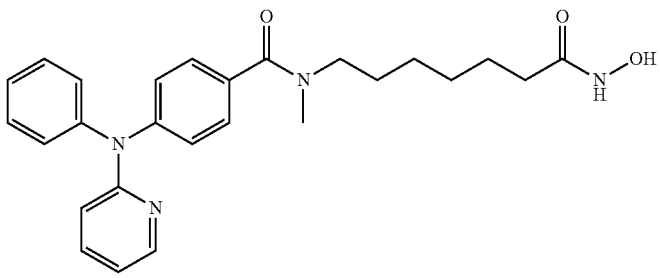 [SMILES: CN(CCCCCCC(=O)NO)C(=O)c1ccc(N(c2ccccc2)c2ccccn2)cc1]

N-(7-(hydroxyamino)-7-oxoheptyl)-N-methyl-
4-(phenyl(pyridin-2-yl)amino) benzamide
IC$_{50}$(nM) HDAC6 = 15 HDAC3 = 100

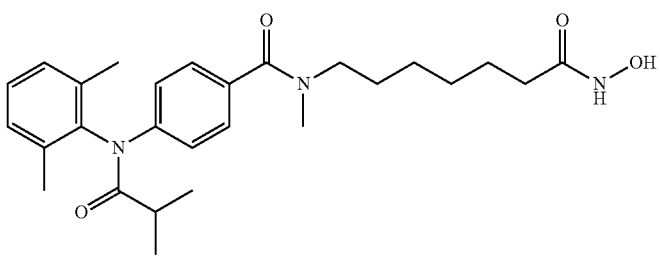 [SMILES: Cc1cccc(C)c1N(C(=O)C(C)C)c1ccc(C(=O)N(C)CCCCCCC(=O)NO)cc1]

4-(N-(2,6-dimethylphenyl)isobutyramido)-N-
(7-(hydroxyamino)-7-oxoheptyl)-N-
methylbenzamide
IC$_{50}$(nM) HDAC6 = 37 HDAC3 = 386

TABLE 1-continued

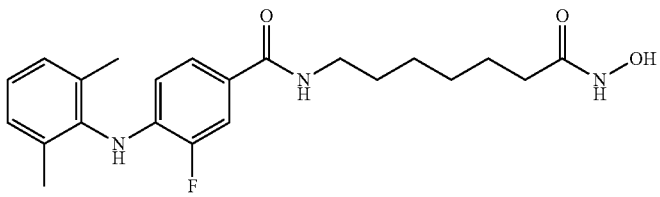 [SMILES: Cc1cccc(C)c1Nc1ccc(C(=O)NCCCCCCC(=O)NO)cc1F]

4-(2,6-dimethylphenylamino)-3-fluoro-N-(7-(hydroxyamino)-7-oxoheptyl)benzamide
IC$_{50}$(nM) HDAC6 = 4 HDAC3 = 80

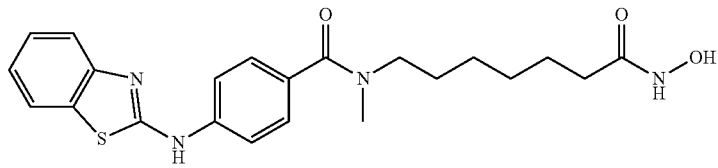 [SMILES: CN(CCCCCCC(=O)NO)C(=O)c1ccc(Nc2nc3ccccc3s2)cc1]

4-(benzo[d]thiazol-2-ylamino)-N-(7-(hydroxyamino)-7-oxoheptyl)-N-methylbenzamide
IC$_{50}$(nM) HDAC6 = 20 HDAC3 = 43

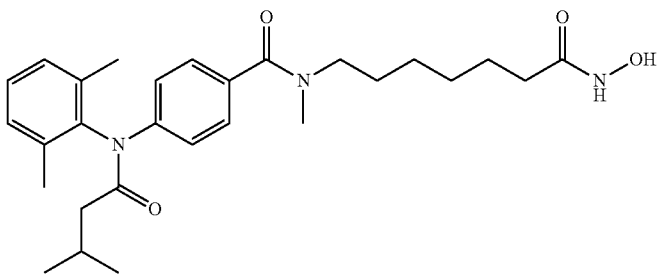 [SMILES: Cc1cccc(C)c1N(C(=O)CC(C)C)c1ccc(C(=O)N(C)CCCCCCC(=O)NO)cc1]

4-(N-(2,6-dimethylphenyl)-3-methylbutanamido)-N-(7-(hydroxyamino)-7-oxoheptyl)-N-methylbenzamide
IC$_{50}$(nM) HDAC6 = 66 HDAC3 = 558

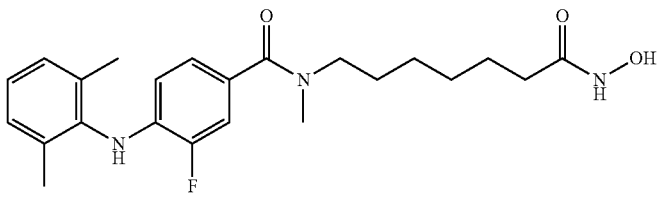 [SMILES: Cc1cccc(C)c1Nc1ccc(C(=O)N(C)CCCCCCC(=O)NO)cc1F]

4-(2,6-dimethylphenylamino)-3-fluoro-N-(7-(hydroxyamino)-7-oxoheptyl)-N-methylbenzamide
IC$_{50}$(nM) HDAC6 = 12 HDAC3 = 204

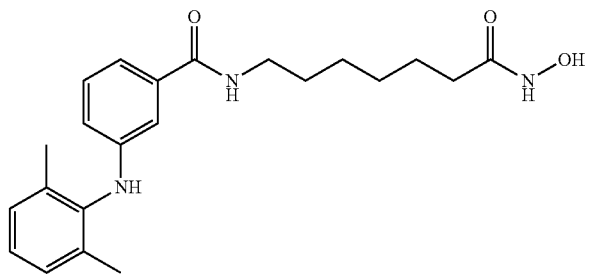 [SMILES: Cc1cccc(C)c1Nc1cccc(C(=O)NCCCCCCC(=O)NO)c1]

3-(2,6-dimethylphenylamino)-N-(7-(hydroxyamino)-7-oxoheptyl)benzamide
IC$_{50}$(nM) HDAC6 = 10 HDAC3 = 54

TABLE 1-continued

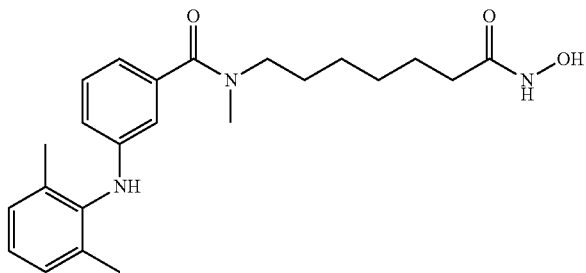 [SMILES: Cc1cccc(C)c1Nc1cccc(C(=O)N(C)CCCCCCC(=O)NO)c1]

3-(2,6-dimethylphenylamino)-N-(7-
(hydroxyamino)-7-oxoheptyl)-N-
methylbenzamide
IC$_{50}$(nM) HDAC6 = 27 HDAC3 = 186

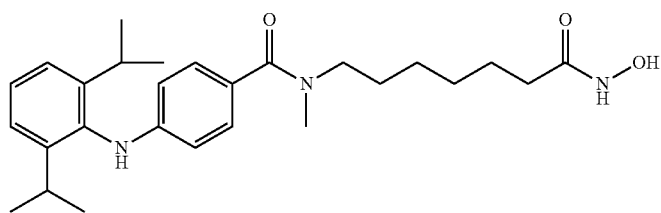 [SMILES: CC(C)c1cccc(C(C)C)c1Nc1ccc(C(=O)N(C)CCCCCCC(=O)NO)cc1]

4-(2,6-diisopropylphenylamino)-N-(7-
(hydroxyamino)-7-oxoheptyl)-N-
methylbenzamide
IC$_{50}$(nM) HDAC6 = 109 HDAC3 = 925

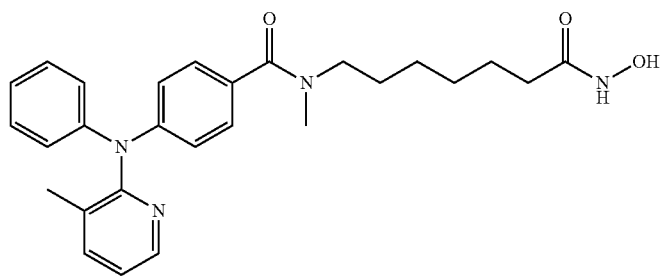 [SMILES: Cc1cccnc1N(c1ccccc1)c1ccc(C(=O)N(C)CCCCCCC(=O)NO)cc1]

N-(7-(hydroxyamino)-7-oxoheptyl)-N-
methyl-4-((3-methylpyridin-2-
yl)(phenyl)amino)benzamide
IC$_{50}$(nM) HDAC6 = 27 HDAC3 = 186

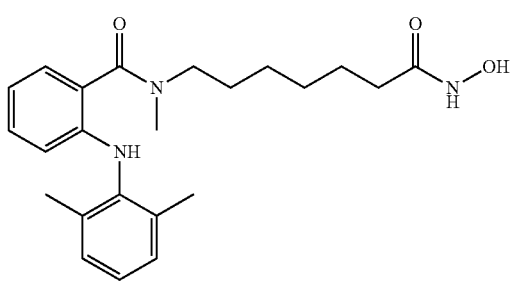 [SMILES: Cc1cccc(C)c1Nc1ccccc1C(=O)N(C)CCCCCCC(=O)NO]

2-(2,6-dimethylphenylamino)-N-(7-
(hydroxyamino)-7-oxoheptyl)-N-
methylbenzamide
IC$_{50}$(nM) HDAC6 = 48 HDAC3 = 242

TABLE 1-continued

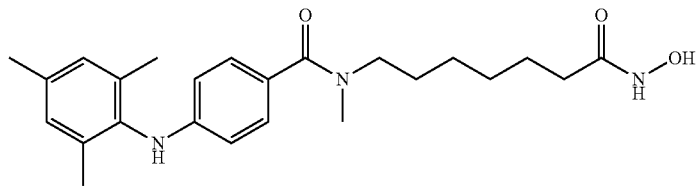 [SMILES: Cc1cc(C)c(Nc2ccc(C(=O)N(C)CCCCCCC(=O)NO)cc2)c(C)c1]

N-(7-(hydroxyamino)-7-oxoheptyl)-4-
(mesitylamino)-N-methylbenzamide
IC$_{50}$(nM) HDAC6 = 35 HDAC3 = 347

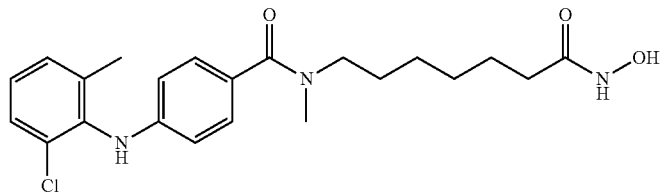 [SMILES: Cc1cccc(Cl)c1Nc1ccc(C(=O)N(C)CCCCCCC(=O)NO)cc1]

4-(2-chloro-6-methylphenylamino)-N-(7-
(hydroxyamino)-7-oxoheptyl)-N-
methylbenzamide
IC$_{50}$(nM) HDAC6 = 11 HDAC3 = 132

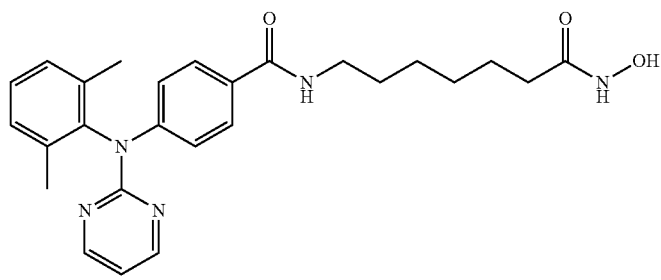 [SMILES: Cc1cccc(C)c1N(c1ccc(C(=O)NCCCCCCC(=O)NO)cc1)c1ncccn1]

4-((2,6-dimethylphenyl)(pyrimidin-2-
yl)amino)-N-(7-(hydroxyamino)-7-
oxoheptyl)benzamide
IC$_{50}$(nM) HDAC6 = 4 HDAC3 = 85

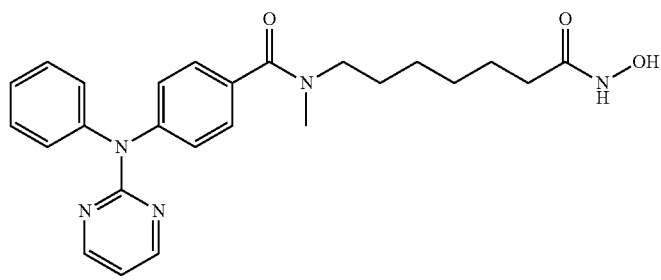 [SMILES: CN(CCCCCCC(=O)NO)C(=O)c1ccc(N(c2ccccc2)c2ncccn2)cc1]

N-(7-(hydroxyamino)-7-oxoheptyl)-N-methyl-
4-(phenyl(pyrimidin-2-yl)amino)benzamide
IC$_{50}$(nM) HDAC6 = 18 HDAC3 = 170

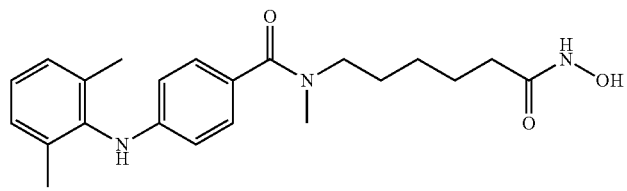 [SMILES: Cc1cccc(C)c1Nc1ccc(C(=O)N(C)CCCCCC(=O)NO)cc1]

4-(2,6-dimethylphenylamino)-N-(6-
(hydroxyamino)-6-oxohexyl)-N-
methylbenzamide
IC$_{50}$(nM) HDAC6 = 46 HDAC3 = 304

TABLE 1-continued

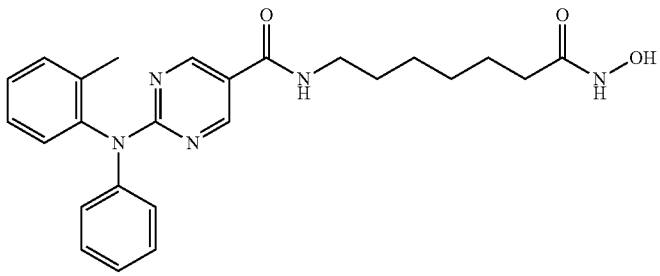 [SMILES: Cc1ccccc1N(c1ccccc1)c1ncc(C(=O)NCCCCCCC(=O)NO)cn1]

N-(7-(hydroxyamino)-7-oxoheptyl)-2-
(phenyl(o-tolyl)amino)pyrimidine-5-
carboxamide
IC$_{50}$(nM) HDAC6 = 9 HDAC3 = 144

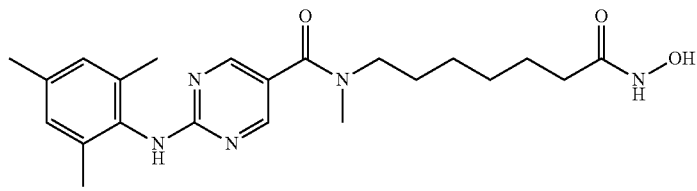 [SMILES: Cc1cc(C)c(Nc2ncc(C(=O)N(C)CCCCCCC(=O)NO)cn2)c(C)c1]

N-(7-(hydroxyamino)-7-oxoheptyl)-2-
(mesitylamino)-N-methylpyrimidine-5-
carboxamide
IC$_{50}$(nM) HDAC6 = 38 HDAC3 = 478

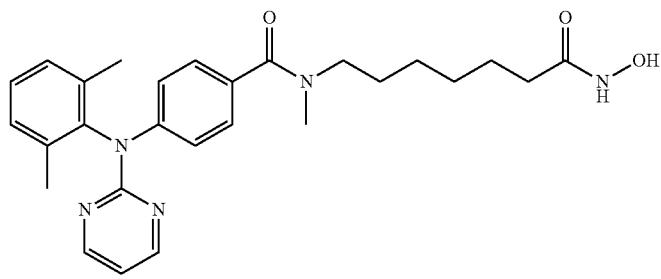 [SMILES: Cc1cccc(C)c1N(c1ccc(C(=O)N(C)CCCCCCC(=O)NO)cc1)c1ncccn1]

4-((2,6-dimethylphenyl)(pyrimidin-2-yl)amino)-
N-(7-(hydroxyamino)-7-oxoheptyl)-N-
methylbenzamide
IC$_{50}$(nM) HDAC6 = 24 HDAC3 = 297

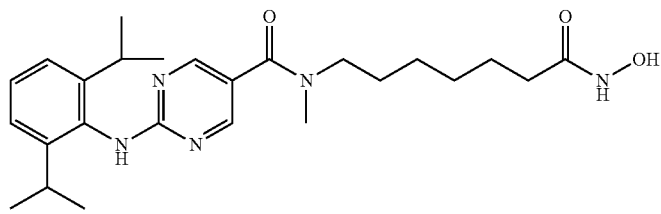 [SMILES: CC(C)c1cccc(C(C)C)c1Nc1ncc(C(=O)N(C)CCCCCCC(=O)NO)cn1]

2-(2,6-diisopropylphenylamino)-N-(7-
(hydroxyamino)-7-oxoheptyl)-N-
methylpyrimidine-5-carboxamide
IC$_{50}$(nM) HDAC6 = 51 HDAC3 = 421

TABLE 1-continued
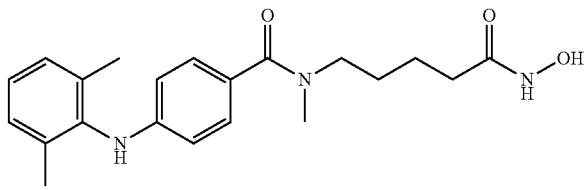 [SMILES: Cc1cccc(C)c1Nc1ccc(C(=O)N(C)CCCCC(=O)NO)cc1]
4-(2,6-dimethylphenylamino)-N-(5-
(hydroxyamino)-5-oxopentyl)-N-
methylbenzamide
IC$_{50}$(nM) HDAC6 = 363 HDAC3 = 2066
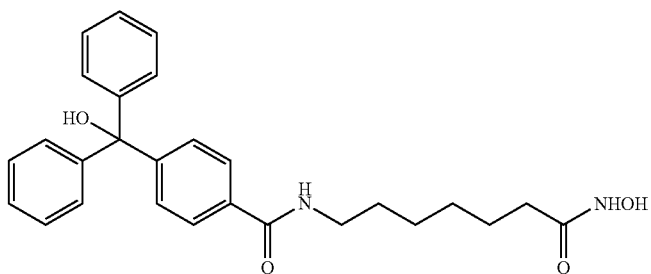
N-(7-(hydroxyamino)-7-oxoheptyl)-4-
(hydroxydiphenylmethyl)benzamide
IC$_{50}$(nM) HDAC6 = 10 HDAC3 = 160
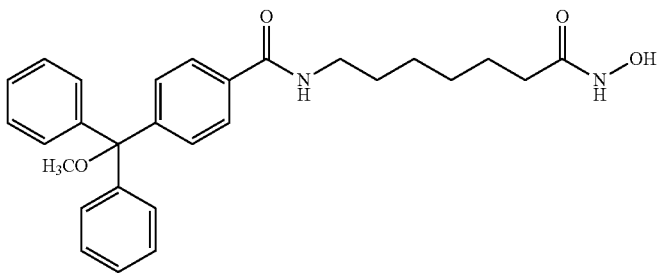 [SMILES: COC(c1ccccc1)(c1ccccc1)c1ccc(C(=O)NCCCCCCC(=O)NO)cc1]
N-(7-(hydroxyamino)-7-oxoheptyl)-4-
(methoxydiphenylmethyl)benzamide
IC$_{50}$(nM) HDAC6 = 7 HDAC3 = 243
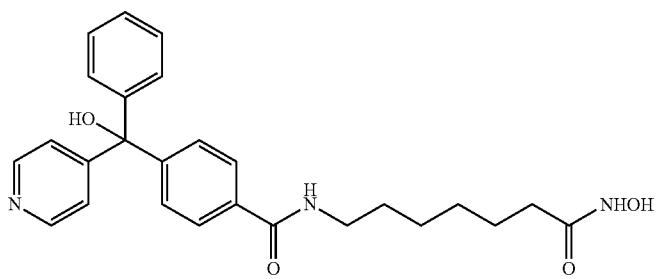
4-(hydroxy(phenyl)(pyridin-4-yl)methyl)-N-
(7-(hydroxyamino)-7-oxoheptyl) benzamide
IC$_{50}$(nM) HDAC6 = 4 HDAC3 = 78

TABLE 1-continued

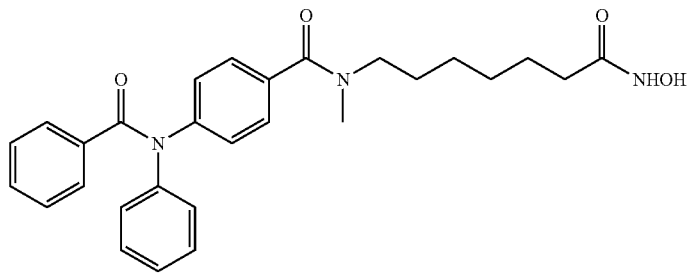

N-(7-(hydroxyamino)-7-oxoheptyl)-N-methyl-
4-(N-phenylbenzamido)benzamide
IC$_{50}$(nM) HDAC6 = 27 HDAC3 = 378

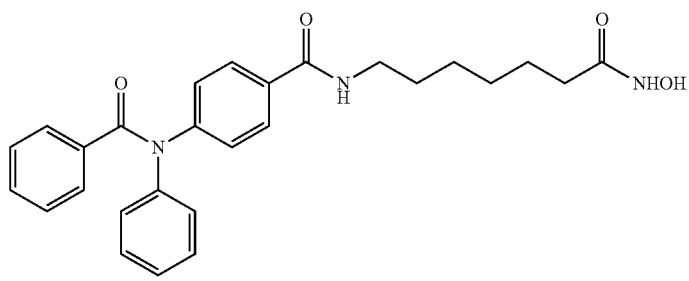

N-(4-(7-(hydroxyamino)-7-
oxoheptylcarbamoyl)phenyl)-N-
phenylbenzamide
IC$_{50}$(nM) HDAC6 = 2 HDAC3 = 67

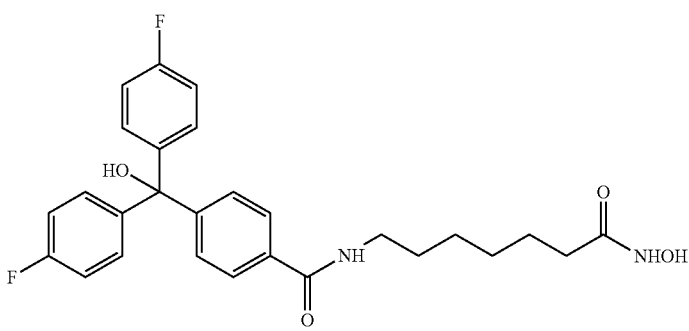

4-(bis(4-fluorophenyl)(hydroxy)methyl)-N-(7-
(hydroxyamino)-7-oxoheptyl)benzamide
IC$_{50}$(nM) HDAC6 = 3 HDAC3 = 121

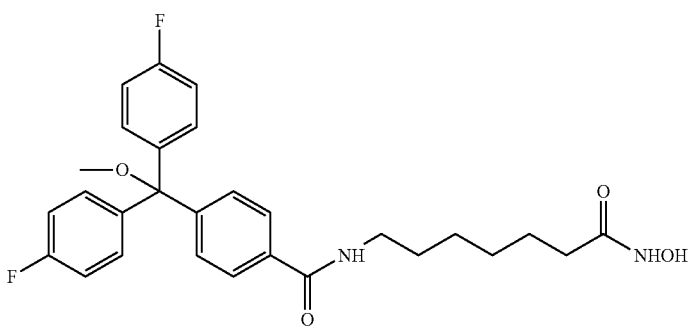

4-(bis(4-fluorophenyl)(methoxy)methyl)-N-
(7-(hydroxyamino)-7-oxoheptyl) benzamide
IC$_{50}$(nM) HDAC6 = 13 HDAC3 = 1225

TABLE 1-continued

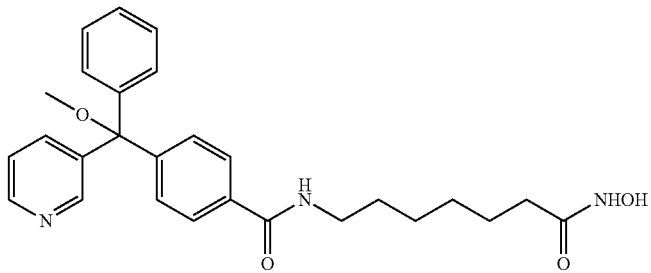

N-(7-(hydroxyamino)-7-oxoheptyl)-4-
(methoxy(phenyl)(pyridin-3-
yl)methyl)benzamide
IC$_{50}$(nM) HDAC6 = 3 HDAC3 = 73

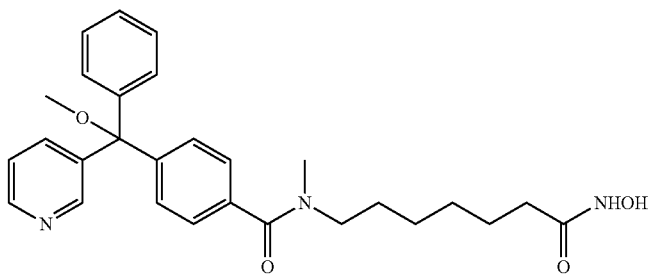

N-(7-(hydroxyamino)-7-oxoheptyl)-4-
(methoxy(phenyl)(pyridin-3-yl)methyl)-N-
methylbenzamide
IC$_{50}$(nM) HDAC6 = 19 HDAC3 = 319

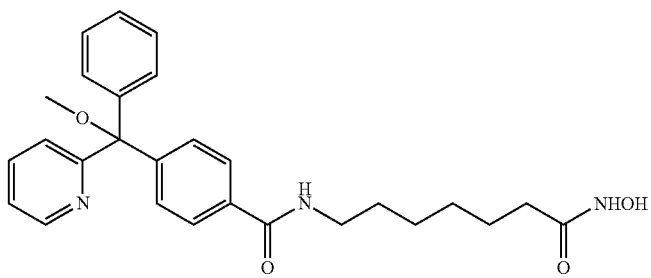

N-(7-(hydroxyamino)-7-oxoheptyl)-4-
(methoxy(phenyl)(pyridin-2-yl)methyl)
benzamide
IC$_{50}$(nM) HDAC6 = 3 HDAC3 = 130

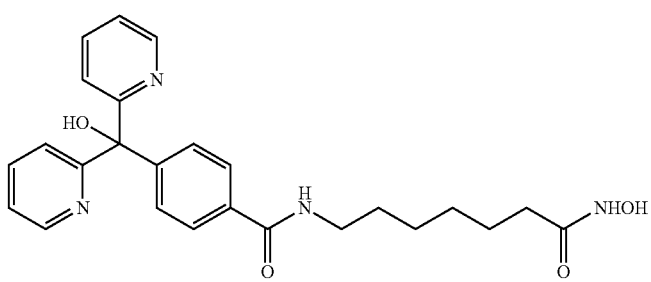

N-(7-(hydroxyamino)-7-oxoheptyl)-4-
(hydroxydipyridin-2-ylmethyl)benzamide
IC$_{50}$(nM) HDAC6 = 4 HDAC3 = 123

TABLE 1-continued

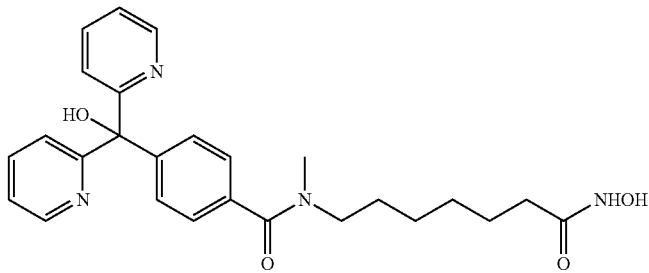

N-(7-(hydroxyamino)-7-oxoheptyl)-4-
(hydroxydipyridin-2-ylmethyl)-N-methyl
benzamide
IC$_{50}$(nM) HDAC6 = 36 HDAC3 = 550

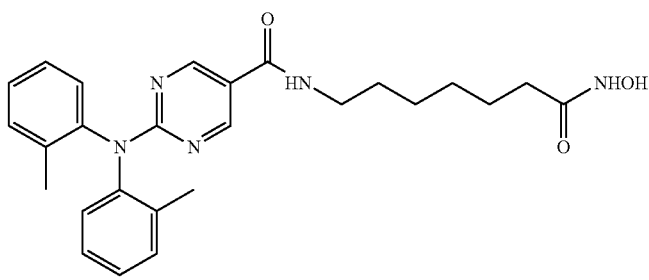

2-(di-o-tolylamino)-N-(7-(hydroxyamino)-7-
oxoheptyl)pyrimidine-5-carboxamide
IC$_{50}$(nM) HDAC6 = 9 HDAC3 = 138

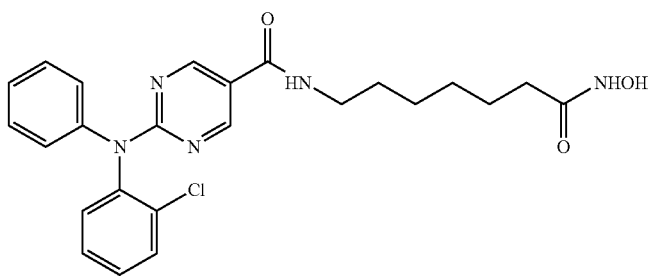

2-((2-chlorophenyl)(phenyl)amino)-N-(7-
(hydroxyamino)-7-oxoheptyl)pyrimidine-5-
carboxamide
IC$_{50}$(nM) HDAC6 = 4 HDAC3 = 76

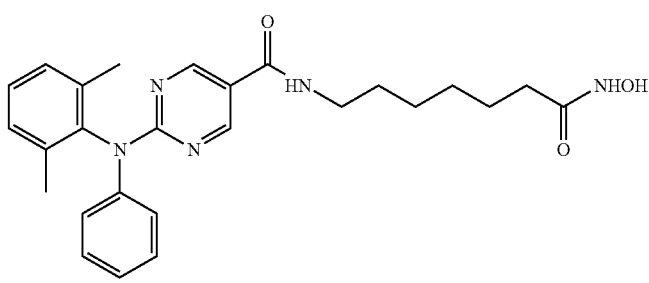

2-((2,6-dimethylphenyl)(phenyl)amino)-N-(7-
(hydroxyamino)-7-oxoheptyl)pyrimidine-5-
carboxamide
IC$_{50}$(nM) HDAC6 = 5 HDAC3 = 137

TABLE 1-continued

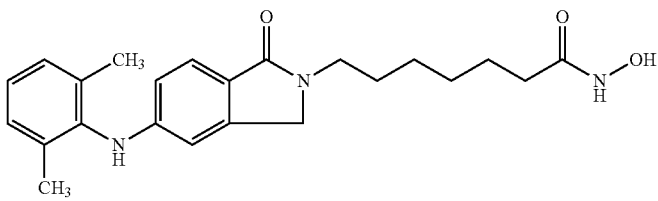 [SMILES: Cc1cccc(C)c1Nc1ccc2c(c1)CN(CCCCCCC(=O)NO)C2=O]

7-(5-(2,6-dimethylphenylamino)-1-
oxoisoindolin-2-yl)-N-hydroxyheptanamide
$IC_{50}$(nM) HDAC6 = 3  HDAC3 = 37

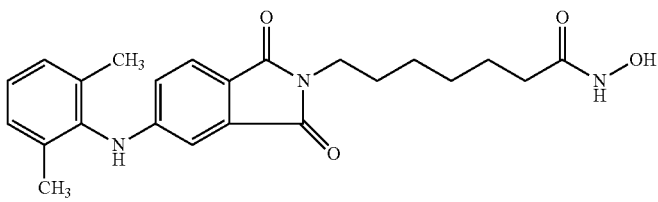 [SMILES: Cc1cccc(C)c1Nc1ccc2c(c1)C(=O)N(CCCCCCC(=O)NO)C2=O]

7-(5-(2,6-dimethylphenylamino)-1,3-
dioxoisoindolin-2-yl)-N-hydroxyheptanamide
$IC_{50}$(nM) HDAC6 = TBD  HDAC3 = TBD

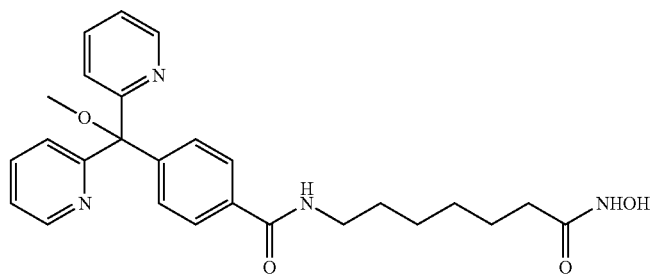

N-(7-(hydroxyamino)-7-oxoheptyl)-4-
(methoxydipyridin-2-ylmethyl)benzamide
$IC_{50}$(nM) HDAC6 = TBD  HDAC3 = TBD

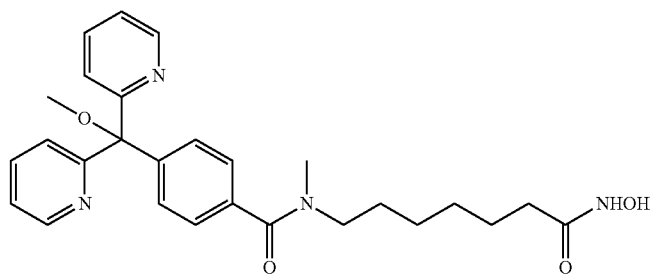

N-(7-(hydroxyamino)-7-oxoheptyl)-4-
(methoxydipyridin-2-ylmethyl)-N-
methylbenzamide
$IC_{50}$(nM) HDAC6 = TBD  HDAC3 = TBD TABLE 1-continued

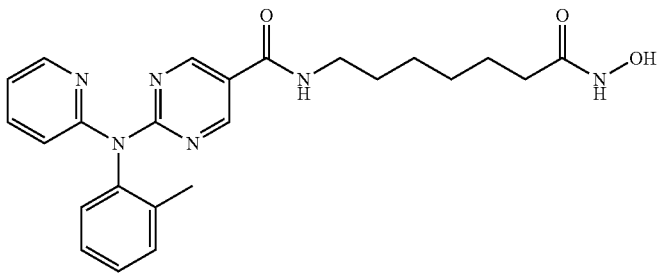 [SMILES: Cc1ccccc1N(c1ccccn1)c1ncc(C(=O)NCCCCCCC(=O)NO)cn1]

N-(7-(hydroxyamino)-7-oxoheptyl)-2-(pyridin-
2-yl(o-tolyl)amino)pyrimidine-5-carboxamide
$IC_{50}$(nM) HDAC6 = TBD HDAC3 = TBD

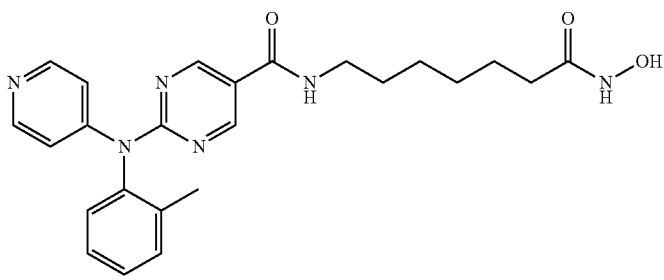 [SMILES: Cc1ccccc1N(c1ccncc1)c1ncc(C(=O)NCCCCCCC(=O)NO)cn1]

N-(7-(hydroxyamino)-7-oxoheptyl)-2-
(pyridin-4-yl(o-tolyl)amino)pyrimidine-5-
carboxamide
$IC_{50}$(nM) HDAC6 = TBD HDAC3 = TBD

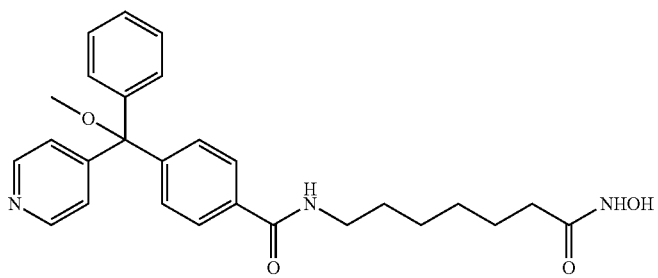

N-(7-(hydroxyamino)-7-oxoheptyl)-4-
(methoxy(phenyl)(pyridin-4-
yl)methyl)benzamide
$IC_{50}$(nM) HDAC6 = 3 HDAC3 = 78

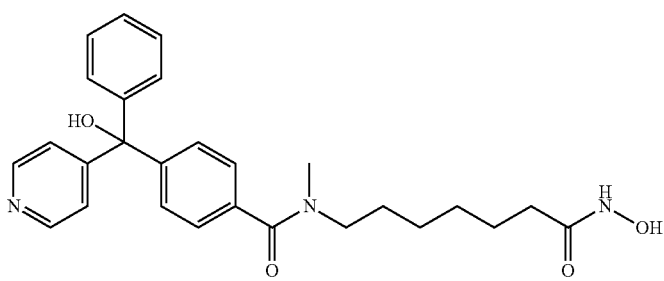 [SMILES: CN(CCCCCCC(=O)NO)C(=O)c1ccc(C(O)(c2ccccc2)c2ccncc2)cc1]

4-(hydroxy(phenyl)(pyridin-4-yl)methyl)-N-
(7-(hydroxyamino)-7-oxoheptyl)-N-
methylbenzamide
$IC_{50}$(nM) HDAC6 = 18 HDAC3 = 221

TABLE 1-continued
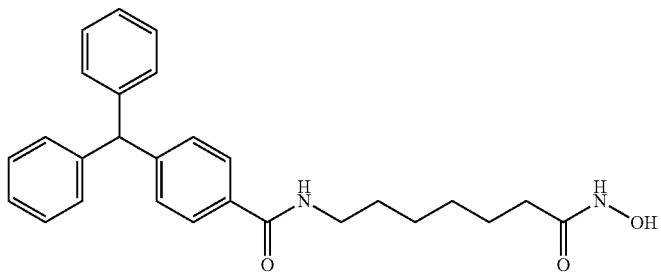 [SMILES: O=C(CCCCCCNC(=O)c1ccc(C(c2ccccc2)c2ccccc2)cc1)NO]
4-benzhydryl-N-(7-(hydroxyamino)-7-
oxoheptyl)-N-methylbenzamide
IC$_{50}$(nM) HDAC6 = 22 HDAC3 = 370
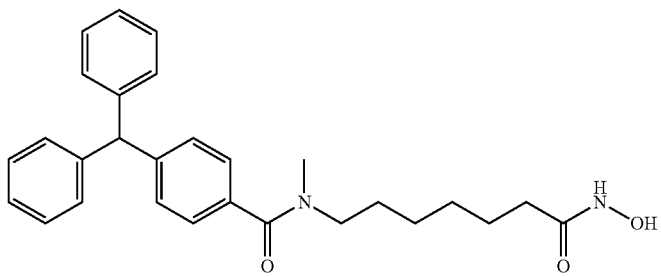
4-benzhydryl-N-(7-(hydroxyamino)-7-
oxoheptyl)benzamide
IC$_{50}$(nM) HDAC6 = 47 HDAC3 = 544
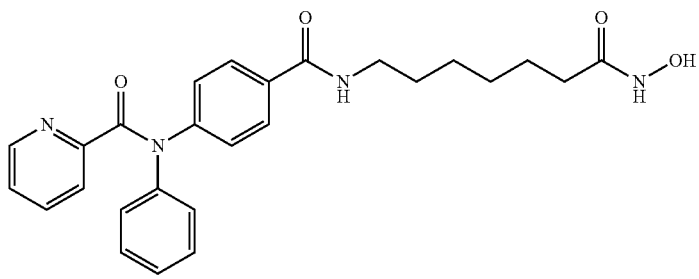 [SMILES: O=C(CCCCCCNC(=O)c1ccc(N(C(=O)c2ccccn2)c2ccccc2)cc1)NO]
N-(4-(7-(hydroxyamino)-7-oxoheptyl
carbamoyl)phenyl)-N-phenylpicolinamide
IC$_{50}$(nM) HDAC6 = 5 HDAC3 = 68
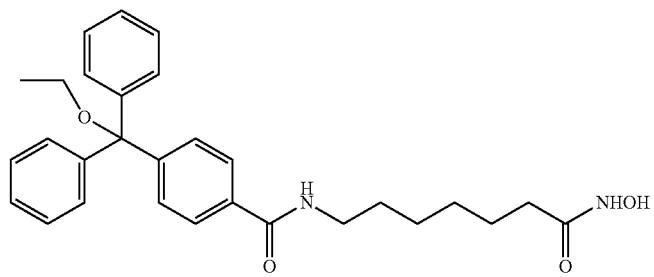
4-(ethoxydiphenylmethyl)-N-(7-
(hydroxyamino)-7-oxoheptyl)benzamide
IC$_{50}$(nM) HDAC6 = 13 HDAC3 = 705

TABLE 1-continued

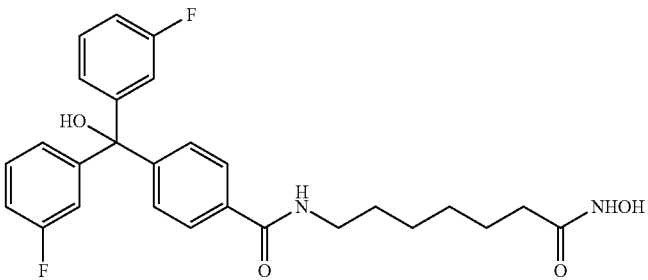

4-(bis(3-fluorophenyl)(hydroxy)methyl)-N-(7-
(hydroxyamino)-7-oxoheptyl)benzamide
IC$_{50}$(nM) HDAC6 = 5 HDAC3 = 186

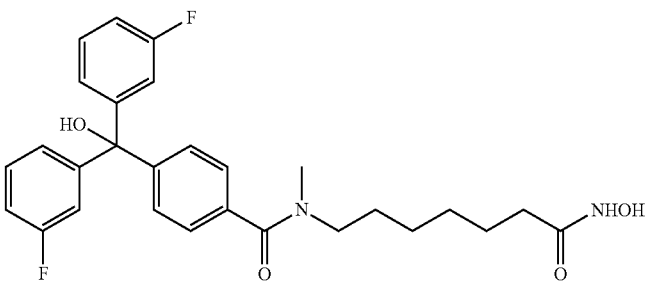

4-(bis(3-fluorophenyl)(hydroxy)methyl)-N-
(7-(hydroxyamino)-7-oxoheptyl)-N-
methylbenzamide
IC$_{50}$(nM) HDAC6 = 10 HDAC3 = 319

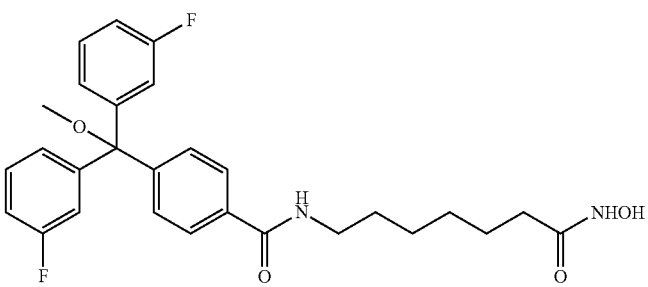

4-(bis(3-fluorophenyl)(methoxy)methyl)-N-(7-
(hydroxyamino)-7-oxoheptyl)benzamide
IC$_{50}$(nM) HDAC6 = 15 HDAC3 = 1261

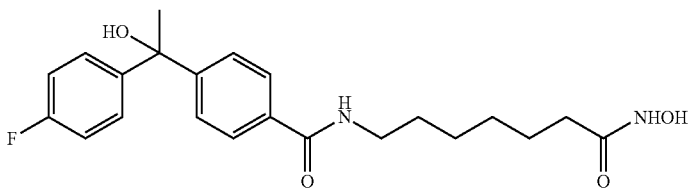

4-(1-(4-fluorophenyl)-1-hydroxyethyl)-N-(7-
(hydroxyamino)-7-oxoheptyl)benzamide
IC$_{50}$(nM) HDAC6 = 3 HDAC3 = 42

TABLE 1-continued
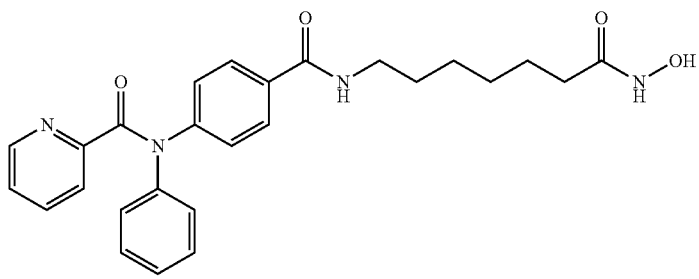 [SMILES: O=C(CCCCCCNC(=O)c1ccc(N(C(=O)c2ccccn2)c2ccccc2)cc1)NO]
N-(4-(7-(hydroxyamino)-7-oxoheptyl
carbamoyl)phenyl)-N-phenylpicolinamide
IC$_{50}$(nM) HDAC6 = 5 HDAC3 = 68
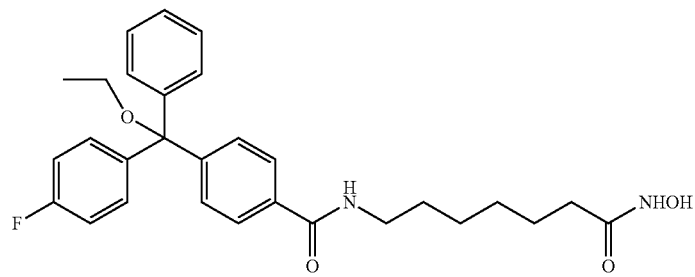
4-(ethoxydiphenylmethyl)-N-(7-
(hydroxyamino)-7-oxoheptyl)benzamide
IC$_{50}$(nM) HDAC6 = 13 HDAC3 = 705
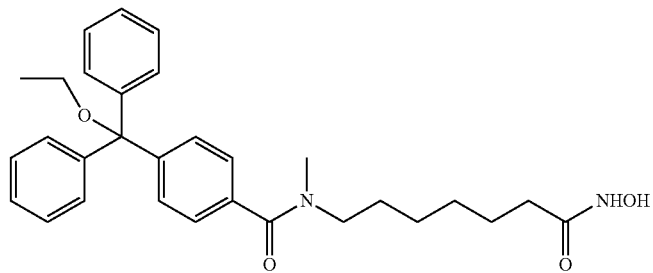
4-(ethoxydiphenylmethyl)-N-(7-(hydroxy
amino)-7-oxoheptyl)-N-methylbenzamide
IC$_{50}$(nM) HDAC6 = 36 HDAC3 = 899
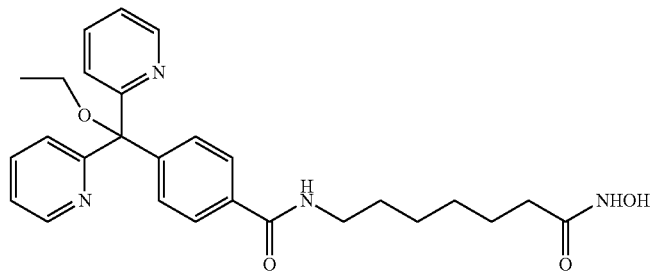
4-(ethoxydipyridin-2-ylmethyl)-N-(7-
(hydroxyamino)-7-oxoheptyl)benzamide
IC$_{50}$(nM) HDAC6 = 6 HDAC3 = 138

TABLE 1-continued

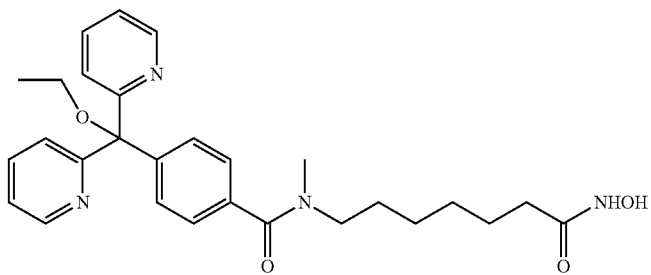

4-(ethoxydipyridin-2-ylmethyl)-N-(7-(hydroxy
amino)-7-oxoheptyl)-N-methylbenzamide
IC$_{50}$(nM) HDAC6 = 45 HDAC3 = 443

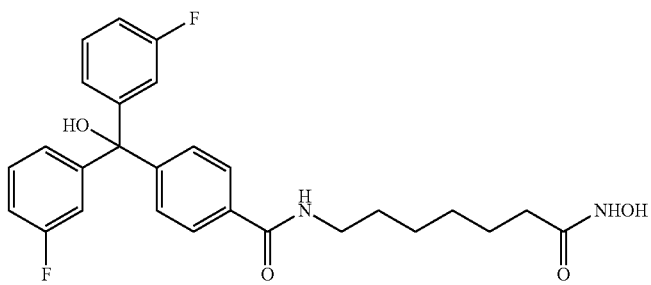

4-(bis(3-fluorophenyl)(hydroxy)methyl)-N-
(7-(hydroxyamino)-7-oxoheptyl)benzamide
IC$_{50}$(nM) HDAC6 = 5 HDAC3 = 186

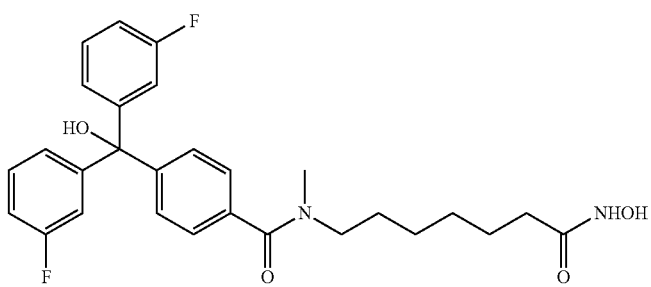

4-(bis(3-fluorophenyl)(hydroxy)methyl)-N-(7-
(hydroxyamino)-7-oxoheptyl)-N-methyl
benzamide
IC$_{50}$(nM) HDAC6 = 10 HDAC3 = 319

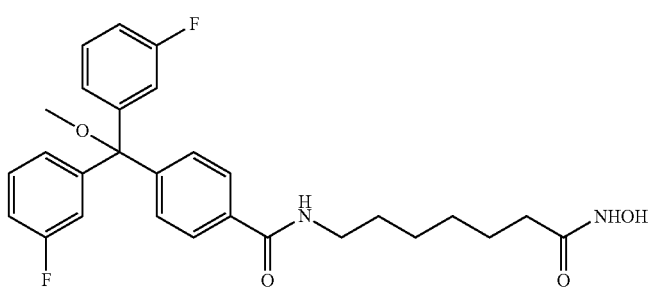

4-(bis(3-fluorophenyl)(methoxy)methyl)-N-
(7-(hydroxyamino)-7-oxoheptyl)benzamide
IC$_{50}$(nM) HDAC6 = 15 HDAC3 = 1281

TABLE 1-continued

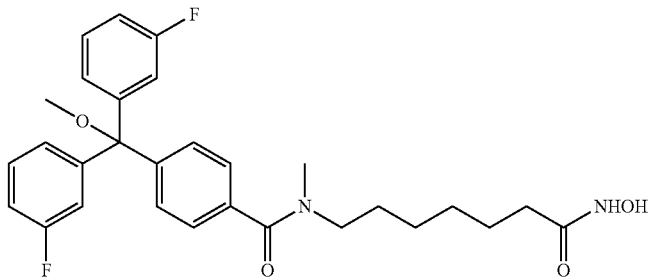

4-(bis(3-fluorophenyl)(methoxy)methyl)-N-(7-
(hydroxyamino)-7-oxoheptyl)-N-methyl
benzamide
IC$_{50}$(nM) HDAC6 = 47  HDAC3 = 805

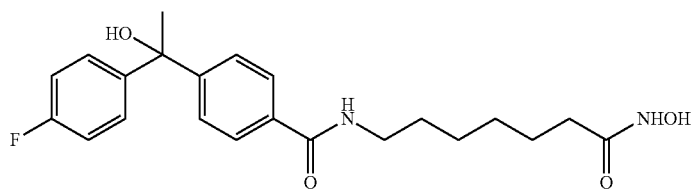

4-(1-(4-fluorophenyl)-1-hydroxyethyl)-N-(7-
(hydroxyamino)-7-oxoheptyl)benzamide
IC$_{50}$(nM) HDAC6 = 3  HDAC3 = 42

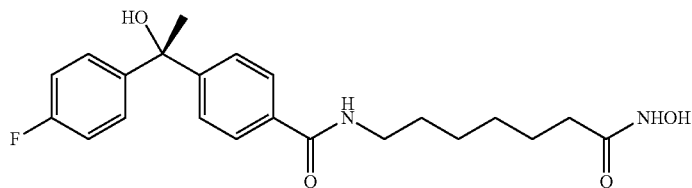

4-(1-(4-fluorophenyl)-1-hydroxyethyl)-N-(7-
(hydroxyamino)-7-oxoheptyl)benzamide
IC$_{50}$(nM) HDAC6 = 3  HDAC3 = 30

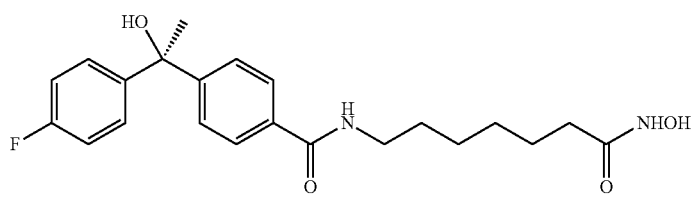

4-(1-(4-fluorophenyl)-1-hydroxyethyl)-N-(7-
(hydroxyamino)-7-oxoheptyl)benzamide
IC$_{50}$(nM) HDAC6 = 3  HDAC3 = 37

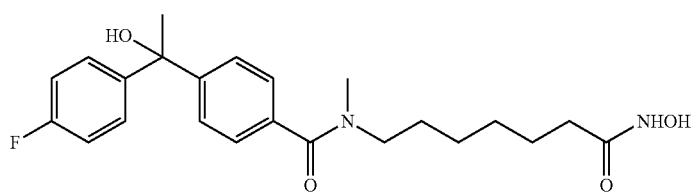

4-(1-(4-fluorophenyl)-1-hydroxyethyl)-N-(7-
(hydroxyamino)-7-oxoheptyl)-N-methyl
benzamide
IC$_{50}$(nM) HDAC6 = 23  HDAC3 = 243

TABLE 1-continued

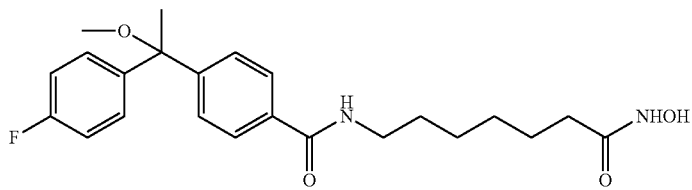

4-(1-(4-fluorophenyl)-1-methoxyethyl)-N-(7-
(hydroxyamino)-7-oxoheptyl)benzamide
IC$_{50}$(nM) HDAC6 = 3 HDAC3 = 28

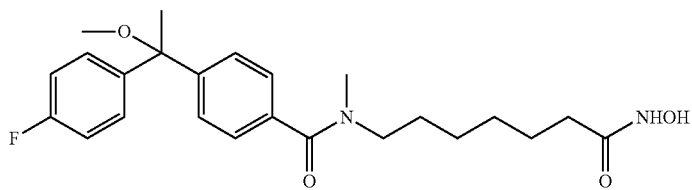

4-(1-(4-fluorophenyl)-1-methoxyethyl)-N-(7-
(hydroxyamino)-7-oxoheptyl)-N-methyl
benzamide
IC$_{50}$(nM) HDAC6 = 17 HDAC3 = 187

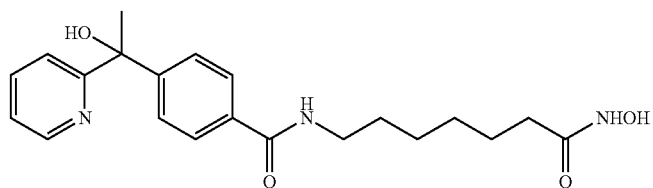

4-(1-hydroxy-1-(pyridin-2-yl)ethyl)-N-(7-
(hydroxyamino)-7-oxoheptyl)benzamide
IC$_{50}$(nM) HDAC6 = 7 HDAC3 = 134

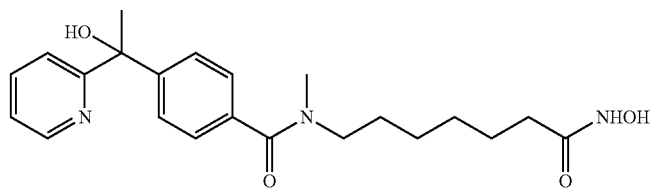

4-(1-hydroxy-1-(pyridin-2-yl)ethyl)-N-(7-
(hydroxyamino)-7-oxoheptyl)-N-methyl
benzamide
IC$_{50}$(nM) HDAC6 = 36 HDAC3 = 501

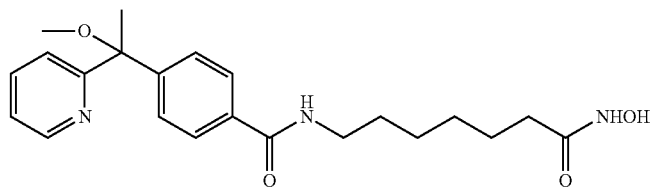

N-(7-(hydroxyamino)-7-oxoheptyl)-4-(1-
methoxy-1-(pyridin-2-yl)ethyl)benzamide
IC$_{50}$(nM) HDAC6 = 4 HDAC3 = 53

TABLE 1-continued

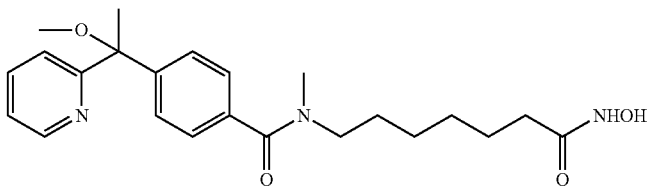

N-(7-(hydroxyamino)-7-oxoheptyl)-4-(1-methoxy-1-(pyridin-2-yl)ethyl)-N-methylbenzamide IC$_{50}$(nM) HDAC6 = 42 HDAC3 = 433

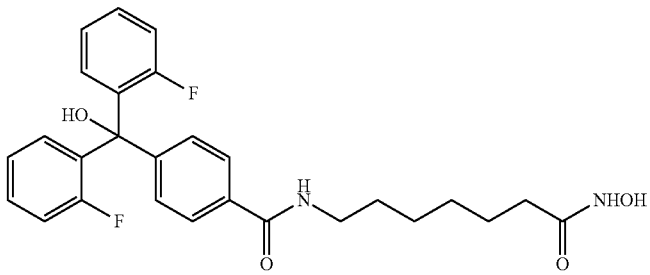

4-(bis(2-fluorophenyl)(hydroxy)methyl)-N-(7-(hydroxyamino)-7-oxoheptyl)benzamide IC$_{50}$(nM) HDAC6 = 3 HDAC3 = 74

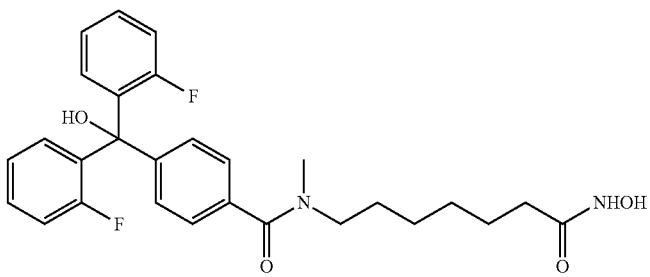

4-(bis(2-fluorophenyl)(hydroxy)methyl)-N-(7-(hydroxyamino)-7-oxoheptyl)-N-methyl benzamide IC$_{50}$(nM) HDAC6 = 9 HDAC3 = 132

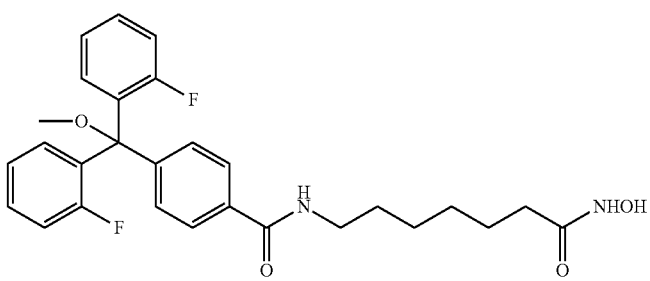

4-(bis(2-fluorophenyl)(methoxy)methyl)-N-(7-(hydroxyamino)-7-oxoheptyl)benzamide IC$_{50}$(nM) HDAC6 = 6 HDAC3 = 184

TABLE 1-continued

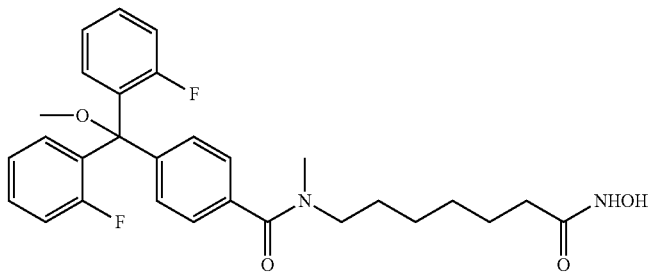

4-(bis(2-fluorophenyl)(methoxy)methyl)-N-(7-(hydroxyamino)-7-oxoheptyl)-N-methyl benzamide
IC$_{50}$(nM) HDAC6 = 17 HDAC3 = 396

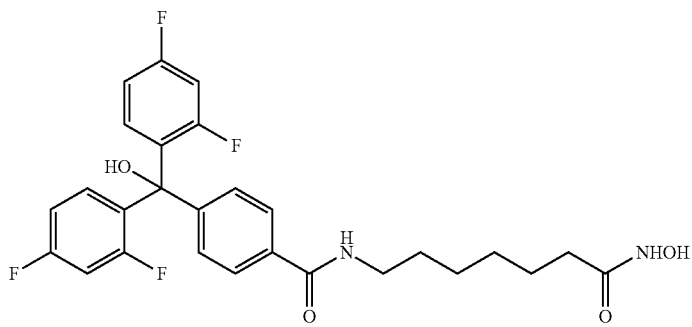

4-(bis(2,4-difluorophenyl)(hydroxy)methyl)-N-(7-(hydroxyamino)-7-oxoheptyl)benzamide
IC$_{50}$(nM) HDAC6 = 5 HDAC3 = 137

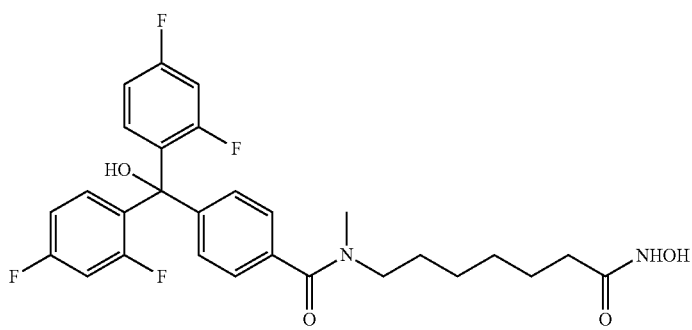

4-(bis(2,4-difluorophenyl)(hydroxy)methyl)-N-(7-(hydroxyamino)-7-oxoheptyl)-N-methylbenzamide
IC$_{50}$(nM) HDAC6 = 13 HDAC3 = 172

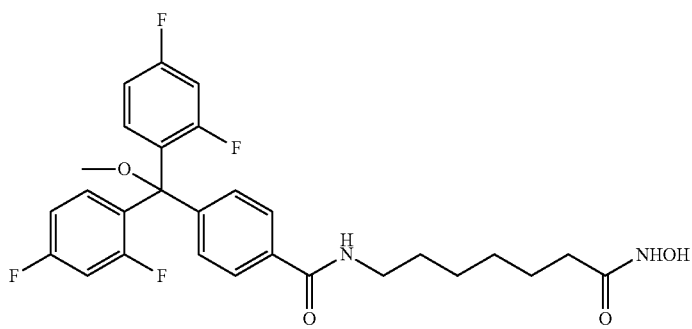

4-(bis(2,4-difluorophenyl)(methoxy)methyl)-N-(7-hydroxyamino)-7-oxoheptyl)benzamide
IC$_{50}$(nM) HDAC6 = 20 HDAC3 = 495

TABLE 1-continued

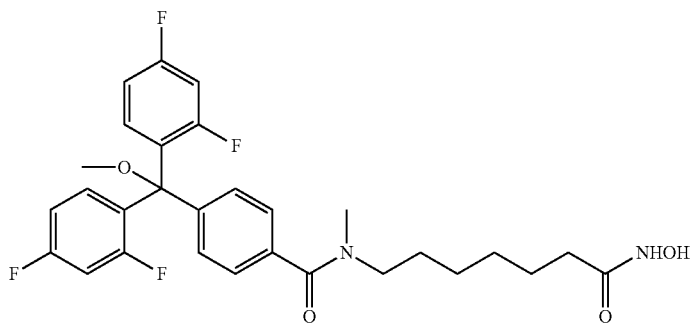

4-(bis(2,4-difluorophenyl)(methoxy)methyl)-N-
(7-(hydroxyamino)-7-oxoheptyl)-N-
methylbenzamide
IC$_{50}$(nM) HDAC6 = 26 HDAC3 = 1335

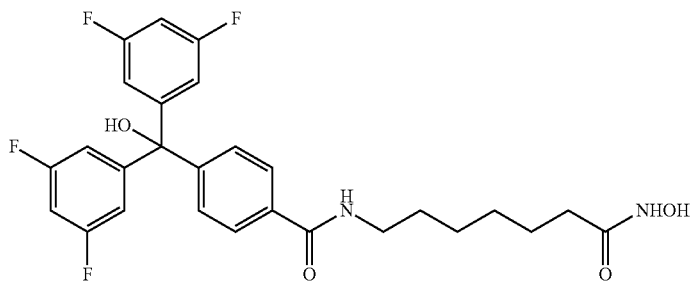

4-(bis(3,5-difluorophenyl)(hydroxy)methyl)-
N-(7-(hydroxyamino)-7-oxoheptyl)benzamide
IC$_{50}$(nM) HDAC6 = 4 HDAC3 = 208

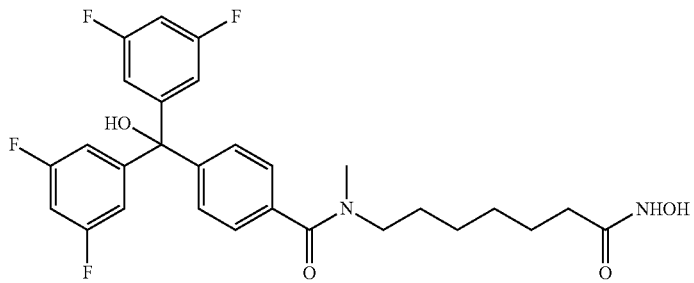

4-(bis(3,5-difluorophenyl)(hydroxy)methyl)-N-
(7-(hydroxyamino)-7-oxoheptyl)-N-
methylbenzamide
IC$_{50}$(nM) HDAC6 = 15 HDAC3 = 186

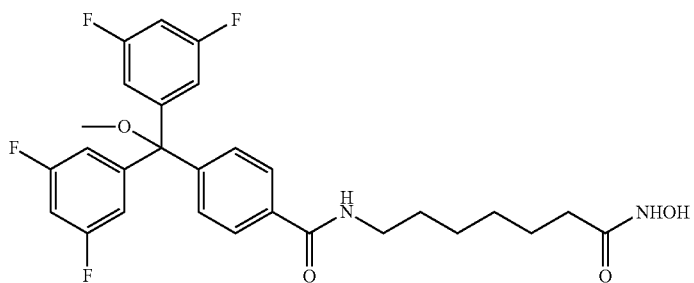

4-(bis(3,5-difluorophenyl)(methoxy)methyl)-
N-(7-(hydroxyamino)-7-oxoheptyl)benzamide
IC$_{50}$(nM) HDAC6 = 20 HDAC3 = 679

TABLE 1-continued

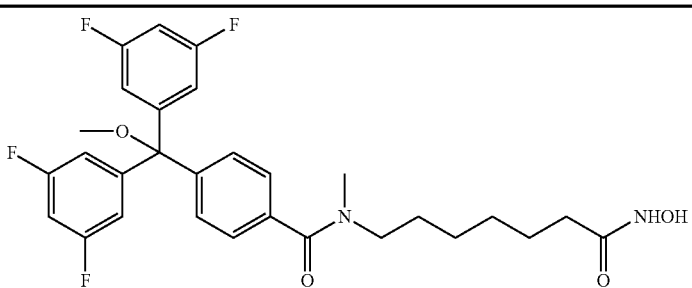

4-(bis(3,5-difluorophenyl)(methoxy)methyl)-N-
(7-(hydroxyamino)-7-oxoheptyl)-N-
methylbenzamide
IC$_{50}$(nM) HDAC6 = 17 HDAC3 = 873

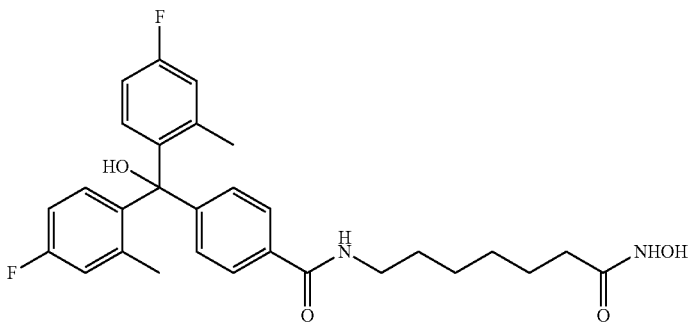

4-(bis(4-fluoro-2-methylphenyl)
(hydroxy)methyl)-N-(7-(hydroxyamino)-7-
oxoheptyl)benzamide
IC$_{50}$(nM) HDAC6 = 59 HDAC3 = 854

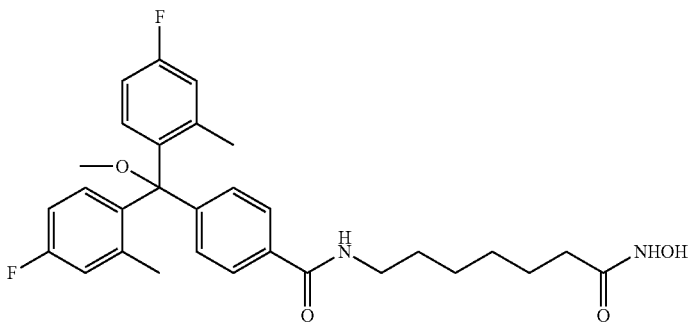

4-(bis(4-fluoro-2-methylphenyl)(methoxy)
methyl)-N-(7-(hydroxyamino)-7-oxoheptyl)
benzamide
IC$_{50}$(nM) HDAC6 = 127 HDAC3 = 2361

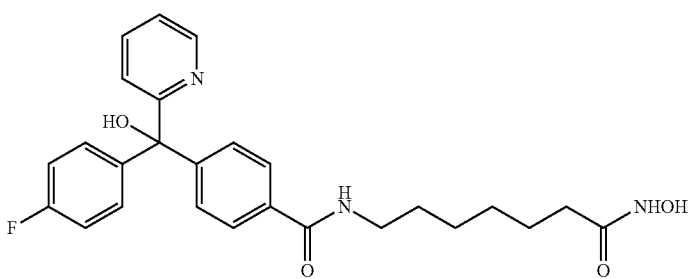

4-((4-fluorophenyl)(hydroxy)(pyridin-2-
yl)methyl)-N-(7-(hydroxyamino)-7-
oxoheptyl)benzamide
IC$_{50}$(nM) HDAC6 = 3 HDAC3 = 80

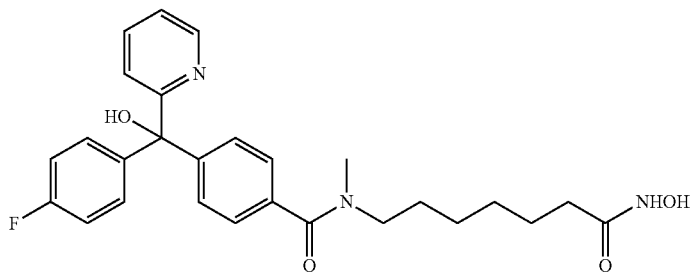

4-((4-fluorophenyl)(hydroxy)(pyridin-2-
yl)methyl)-N-(7-(hydroxyamino)-7-oxoheptyl)-
N-methylbenzamide
IC$_{50}$(nM) HDAC6 = 24 HDAC3 = 284

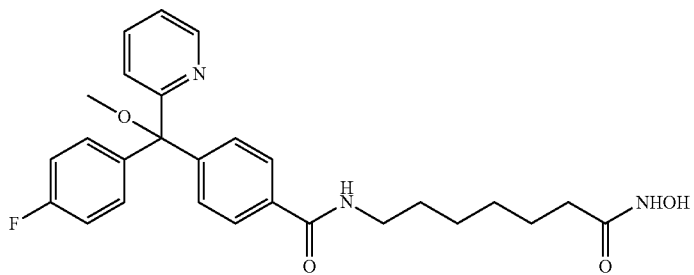

4-((4-fluorophenyl)(methoxy)(pyridin-2-
yl)methyl)-N-(7-(hydroxyamino)-7-
oxoheptyl)benzamide
IC$_{50}$(nM) HDAC6 = 3 HDAC3 = 80

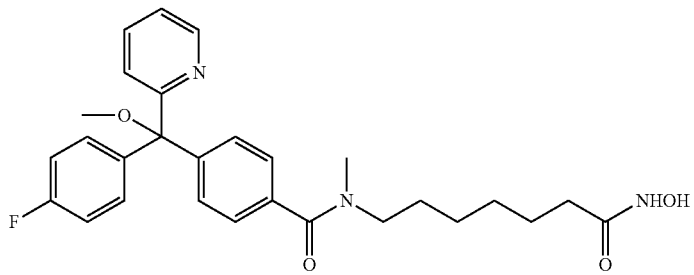

4-((4-fluorophenyl)(methoxy)(pyridin-2-
yl)methyl)-N-(7-(hydroxyamino)-7-oxoheptyl)-
N-methylbenzamide
IC$_{50}$(nM) HDAC6 = 23 HDAC3 = 361

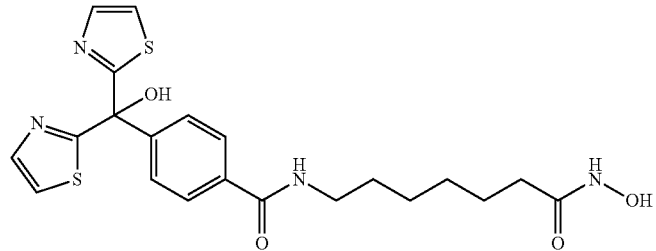 [SMILES: O=C(CCCCCCNC(=O)c1ccc(C(O)(c2nccs2)c2nccs2)cc1)NO]

N-(7-(hydroxyamino)-7-oxoheptyl)-4-
(hydroxydithiazol-2-ylmethyl)benzamide
IC$_{50}$(nM) HDAC6 = 5 HDAC3 = 141

TABLE 1-continued

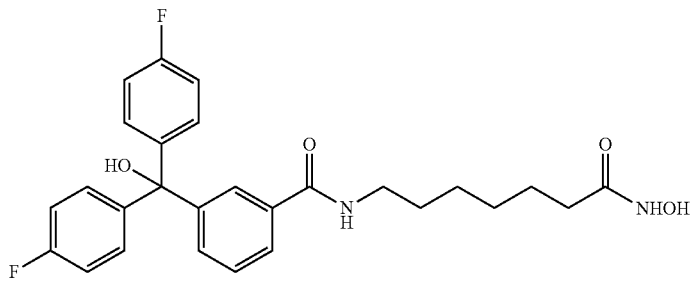

3-(bis(4-fluorophenyl)(hydroxy)methyl)-N-(7-
(hydroxyamino)-7-oxoheptyl)benzamide
IC$_{50}$(nM) HDAC6 = 18 HDAC3 = 63

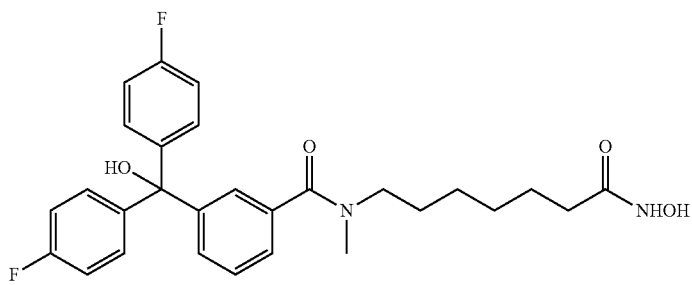

3-(bis(4-fluorophenyl)(hydroxy)methyl)-N-
(7-(hydroxyamino)-7-oxoheptyl)-N-
methylbenzamide
IC$_{50}$(nM) HDAC6 = 72 HDAC3 = 349

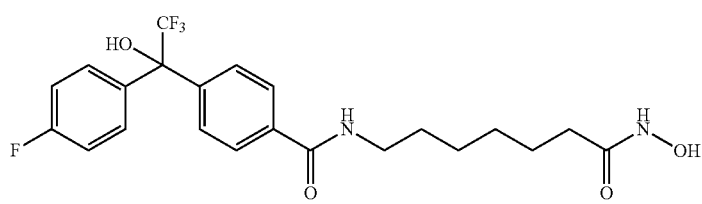 [SMILES: O=C(CCCCCCNC(=O)c1ccc(C(O)(c2ccc(F)cc2)C(F)(F)F)cc1)NO]

N-(7-(hydroxyamino)-7-oxoheptyl)-4-(2,2,2-
trifluoro-1-(4-fluorophenyl)-1-hydroxyethyl)
benzamide
IC$_{50}$(nM) HDAC6 = 5 HDAC3 = 50

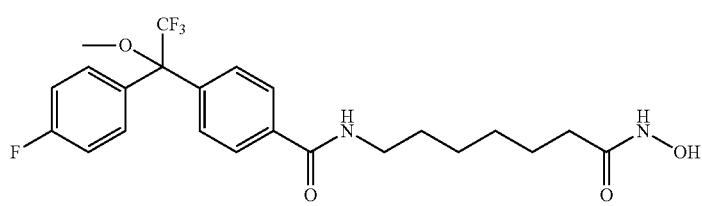 [SMILES: COC(c1ccc(F)cc1)(c1ccc(C(=O)NCCCCCCC(=O)NO)cc1)C(F)(F)F]

N-(7-(hydroxyamino)-7-oxoheptyl)-4-(2,2,2-
trifluoro-1-(4-fluorophenyl)-1-methoxyethyl)
benzamide
IC$_{50}$(nM) HDAC6 = 10 HDAC3 = 174

TABLE 1-continued

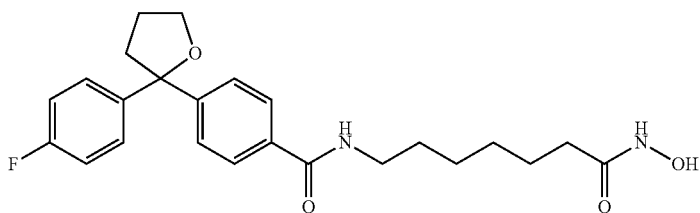 [SMILES: O=C(CCCCCCNC(=O)c1ccc(C2(c3ccc(F)cc3)CCCO2)cc1)NO]

4-(2-(4-fluorophenyl)tetrahydrofuran-2-yl)-N-
(7-(hydroxyamino)-7-oxoheptyl) benzamide
IC$_{50}$(nM) HDAC6 = 3 HDAC3 = 47

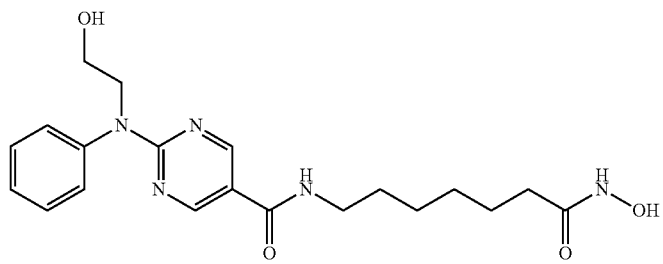 [SMILES: O=C(CCCCCCNC(=O)c1cnc(N(CCO)c2ccccc2)nc1)NO]

N-(7-(hydroxyamino)-7-oxoheptyl)-2-((2-
hydroxyethyl)(phenyl)amino)pyrimidine-5-
carboxamide
IC$_{50}$(nM) HDAC6 = 8 HDAC3 = 75

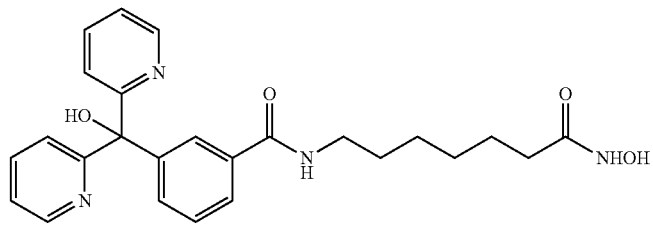

N-(7-(hydroxyamino)-7-oxoheptyl)-3-
(hydroxydipyridin-2-ylmethyl)benzamide
IC$_{50}$(nM) HDAC6 = 41 HDAC3 = 285

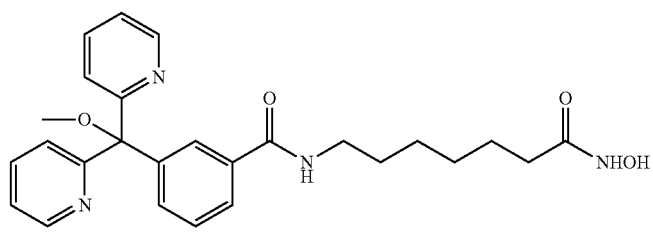

N-(7-(hydroxyamino)-7-oxoheptyl)-3-
(methoxydipyridin-2-ylmethyl)benzamide
IC$_{50}$(nM) HDAC6 = 20 HDAC3 = 217

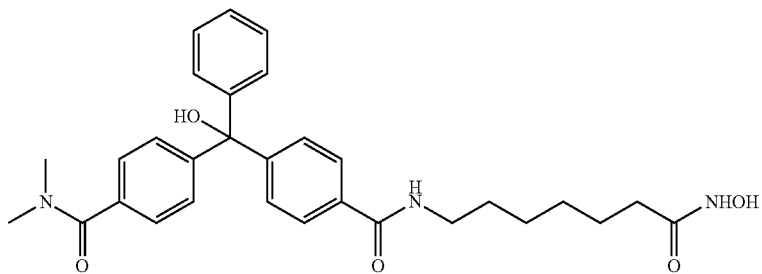

4-(hydroxy(4-(7-(hydroxyamino)-7-
oxoheptylcarbamoyl)phenyl)(phenyl)methyl)-
N,N-dimethylbenzamide
IC$_{50}$(nM) HDAC6 = 4 HDAC3 = 86

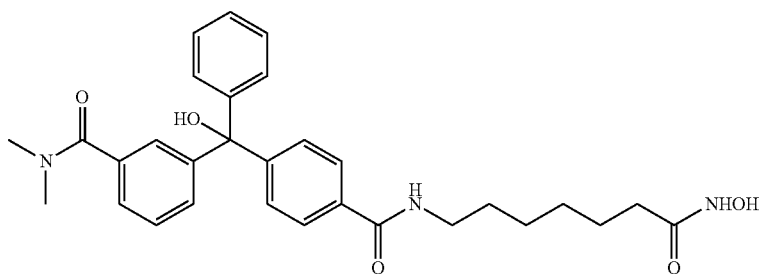

3-(hydroxy(4-(7-(hydroxyamino)-7-
oxoheptylcarbamoyl)phenyl)(phenyl)methyl)-
N,N-dimethylbenzamide
IC$_{50}$(nM) HDAC6 = 3 HDAC3 = 90

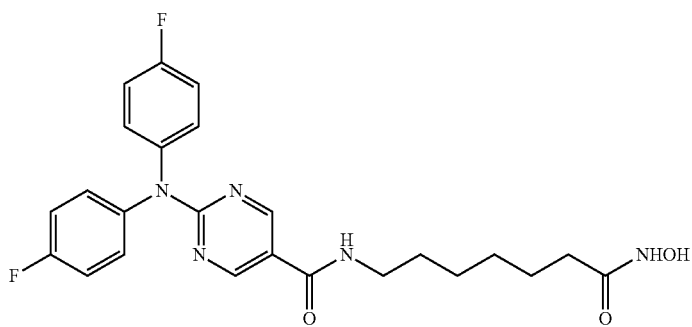

2-(bis(4-fluorophenyl)amino)-N-(7-
(hydroxyamino)-7-oxoheptyl)pyrimidine-5-
carboxamide
IC$_{50}$(nM) HDAC6 = 12 HDAC3 = 124

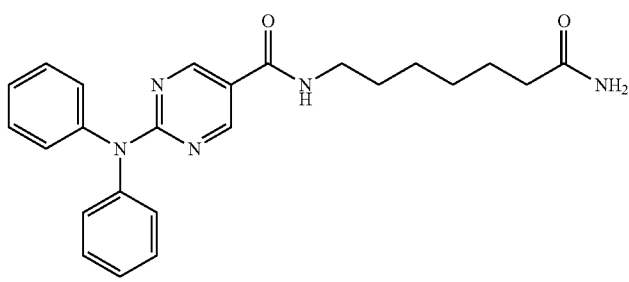 [SMILES: NC(=O)CCCCCCNC(=O)c1cnc(N(c2ccccc2)c2ccccc2)nc1]

N-(7-amino-7-oxoheptyl)-2-
(diphenylamino)pyrimidine-5-carboxamide
IC$_{50}$(nM) HDAC6 = >50 μM HDAC3 = >50 μM TABLE 1-continued

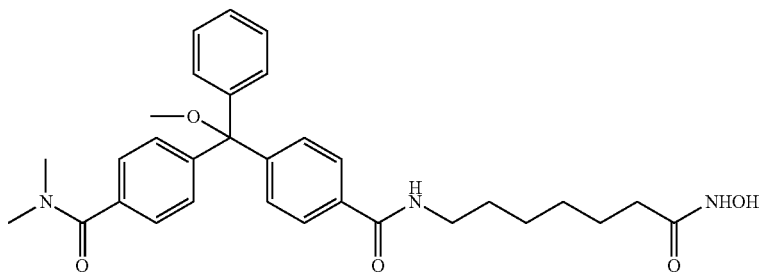

4-((4-(7-(hydroxyamino)-7-
oxoheptylcarbamoyl)phenyl)(methoxy)(phenyl)
methyl)-N,N-dimethylbenzamide
IC$_{50}$(nM) HDAC6 = 4 HDAC3 = 103

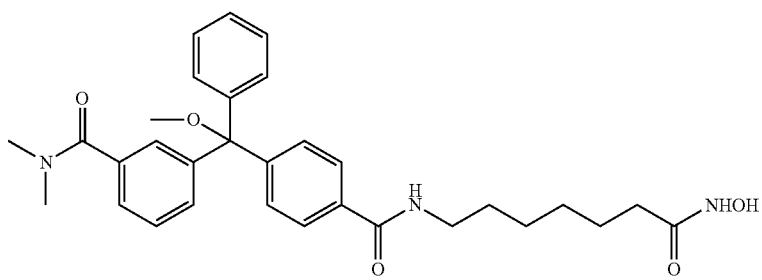

3-((4-(7-(hydroxyamino)-7-
oxoheptylcarbamoyl)phenyl)(methoxy)(phenyl)
methyl)-N,N-dimethylbenzamide
IC$_{50}$(nM) HDAC6 = 3 HDAC3 = 85

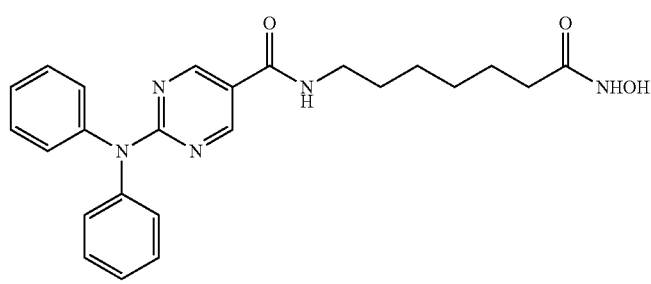

7-(2-(diphenylamino)pyrimidine-5-
carboxamido)heptanoic acid
IC$_{50}$(nM) HDAC6 = 1251 HDAC3 = 19512

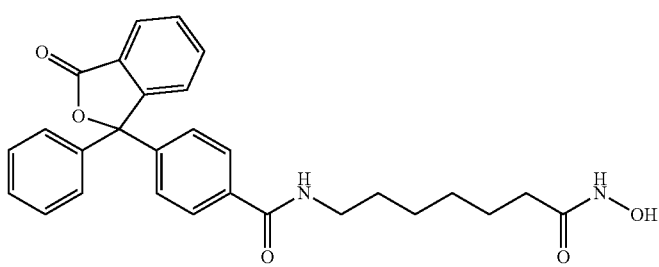 [SMILES: O=C(CCCCCCNC(=O)c1ccc(C2(c3ccccc3)OC(=O)c3ccccc32)cc1)NO]

N-(7-(hydroxyamino)-7-oxoheptyl)-4-(3-
oxo-1-phenyl-1,3-dihydroisobenzofuran-1-
yl)benzamide
IC$_{50}$(nM) HDAC6 = 11 HDAC3 = 153

TABLE 1-continued

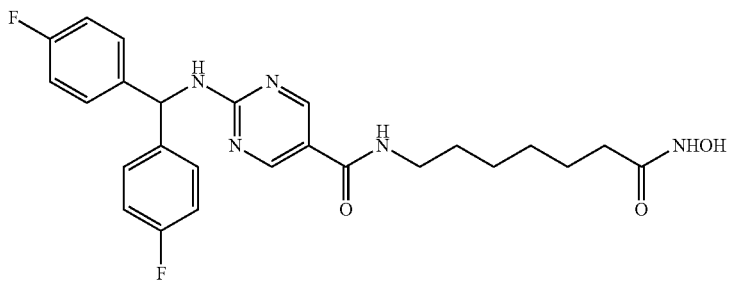

2-(bis(4-fluorophenyl)methylamino)-N-(7-
(hydroxyamino)-7-oxoheptyl)pyrimidine-5-
carboxamide
IC$_{50}$(nM) HDAC6 = 5 HDAC3 = 65

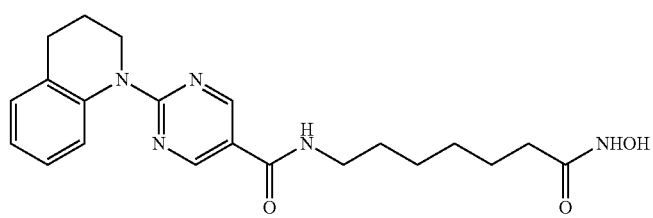

2-(3,4-dihydroquinolin-1(2H)-yl)-N-(7-
(hydroxyamino)-7-oxoheptyl)pyrimidine-5-
carboxamide
IC$_{50}$(nM) HDAC6 = 6 HDAC3 = 50

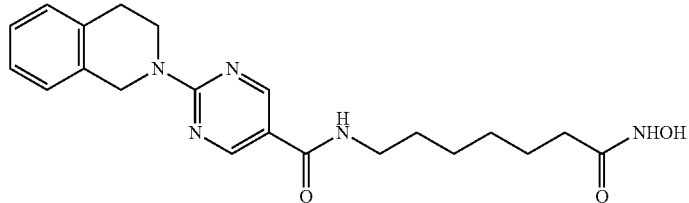

2-(3,4-dihydroisoquinolin-2(1H)-yl)-N-(7-
(hydroxyamino)-7-oxoheptyl)pyrimidine-5-
carboxamide
IC$_{50}$(nM) HDAC6 = 3 HDAC3 = 53

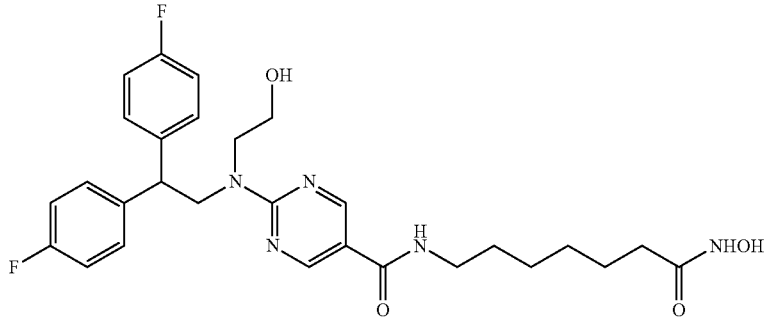

2-((2,2-bis(4-fluorophenyl)ethyl)(2-
hydroxyethyl)amino)-N-(7-(hydroxyamino)-
7-oxoheptyl)pyrimidine-5-carboxamide
IC$_{50}$(nM) HDAC6 = 8 HDAC3 = 64

TABLE 1-continued

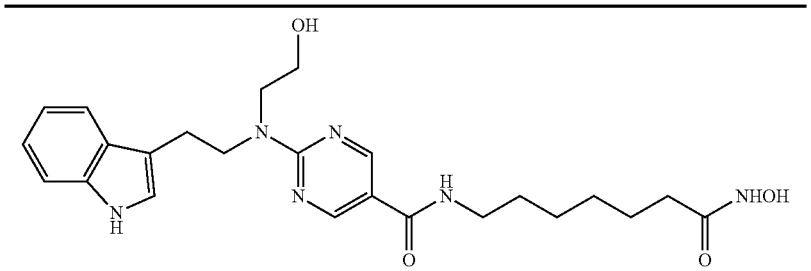

2-((2-(1H-indol-3-yl)ethyl)(2-
hydroxyethyl)amino)-N-(7-(hydroxyamino)-7-
oxoheptyl)pyrimidine-5-carboxamide
IC$_{50}$(nM) HDAC6 = 3 HDAC3 = 35

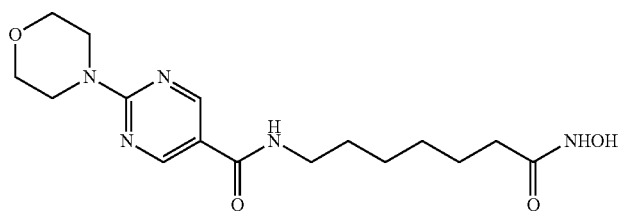

N-(7-(hydroxyamino)-7-oxoheptyl)-2-
morpholinopyrimidine-5-carboxamide
IC$_{50}$(nM) HDAC6 = 8 HDAC3 = 51

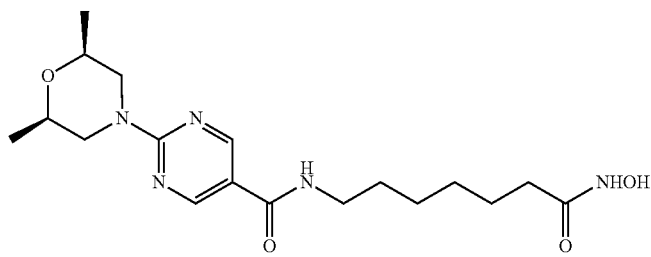

2-((2S,6R)-2,6-dimethylmorpholino)-N-(7-
(hydroxyamino)-7-oxoheptyl)pyrimidine-5-
carboxamide
IC$_{50}$(nM) HDAC6 = 7 HDAC3 = 70

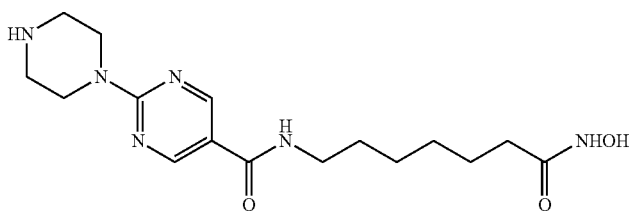

N-(7-(hydroxyamino)-7-oxoheptyl)-2-
(piperazin-1-yl)pyrimidine-5-carboxamide
IC$_{50}$(nM) HDAC6 = 21 HDAC3 = 43

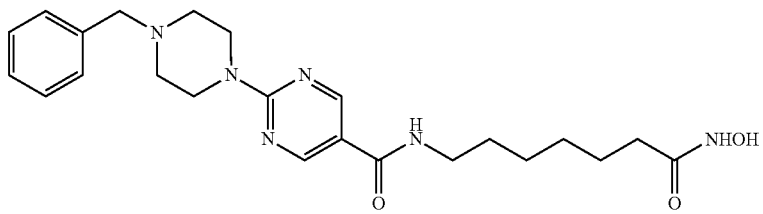

2-(4-benzylpiperazin-1-yl)-N-(7-
(hydroxyamino)-7-oxoheptyl)pyrimidine-5-
carboxamide
IC$_{50}$(nM) HDAC6 = 6 HDAC3 = 100

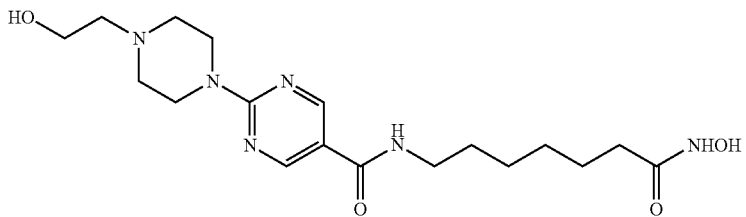

N-(7-(hydroxyamino)-7-oxoheptyl)-2-(4-(2-hydroxyethyl)piperazin-1-yl)pyrimidine-5-carboxamide
$IC_{50}$(nM) HDAC6 = 13 HDAC3 = 58

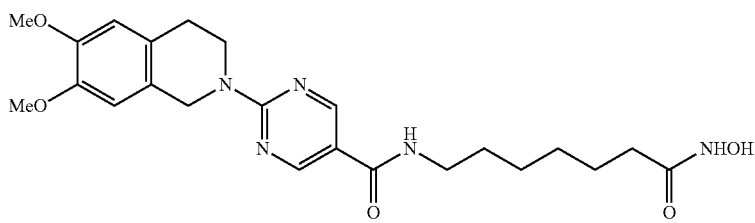

2-(6,7-dimethoxy-3,4-dihydroisoquinolin-2(1H)-yl)-N-(7-(hydroxyamino)-7-oxoheptyl)pyrimidine-5-carboxamide
$IC_{50}$(nM) HDAC6 = 2 HDAC3 = 46

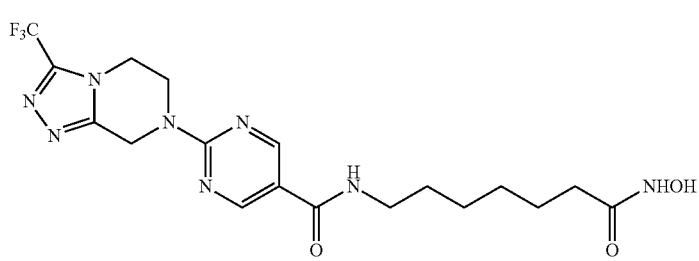

N-(7-(hydroxyamino)-7-oxoheptyl)-2-(3-(trifluoromethyl)-5,6-dihydro-[1,2,4]triazolo[4,3-a]pyrazin-7(8H)-yl)pyrimidine-5-carboxamide
$IC_{50}$(nM) HDAC6 = 14 HDAC3 = 149

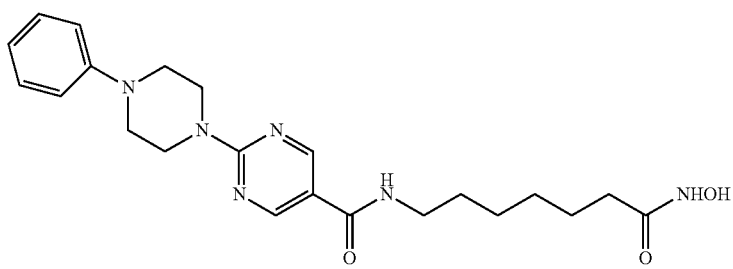

N-(7-(hydroxyamino)-7-oxoheptyl)-2-(4-phenylpiperazin-1-yl)pyrimidine-5-carboxamide
$IC_{50}$(nM) HDAC6 = 4 HDAC3 = 57

TABLE 1-continued

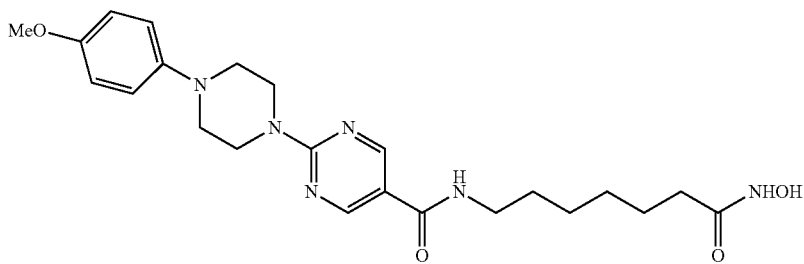

N-(7-(hydroxyamino)-7-oxoheptyl)-2-(4-(4-methoxyphenyl)piperazin-1-yl)pyrimidine-5-carboxamide
IC$_{50}$(nM) HDAC6 = 4 HDAC3 = 58

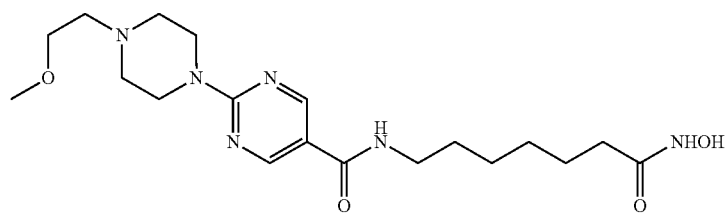

N-(7-(hydroxyamino)-7-oxoheptyl)-2-(4-(2-methoxyethyl)piperazin-1-yl)pyrimidine-5-carboxamide
IC$_{50}$(nM) HDAC6 = 13 HDAC3 = 133

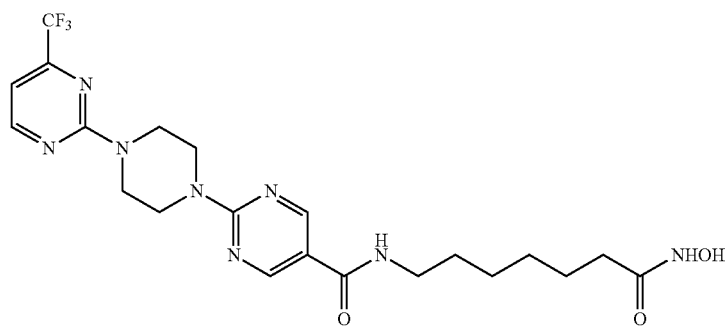

N-(7-(hydroxyamino)-7-oxoheptyl)-2-(4-(4-(trifluoromethyl)pyrimidin-2-yl)piperazin-1-yl)pyrimidine-5-carboxamide
IC$_{50}$(nM) HDAC6 = 7 HDAC3 = 54

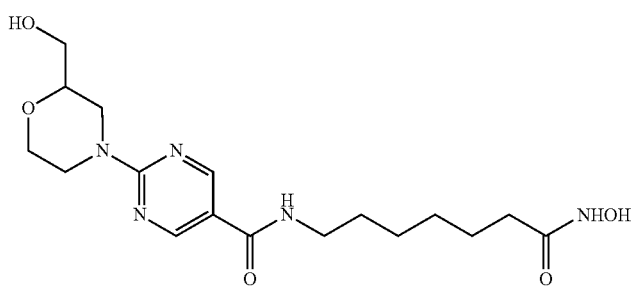

N-(7-(hydroxyamino)-7-oxoheptyl)-2-(2-(hydroxymethyl)morpholino)pyrimidine-5-carboxamide
IC$_{50}$(nM) HDAC6 = 7 HDAC3 = 34

TABLE 1-continued

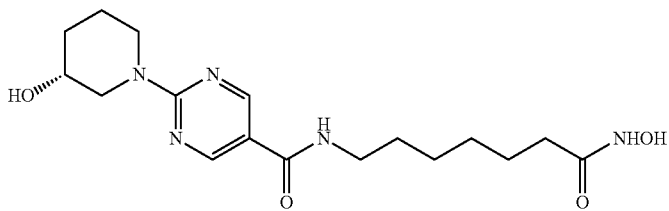

(R)-N-(7-(hydroxyamino)-7-oxoheptyl)-2-(3-
hydroxypiperidin-1-yl)pyrimidine-5-
carboxamide
$IC_{50}$(nM) HDAC6 = 7 HDAC3 = 49

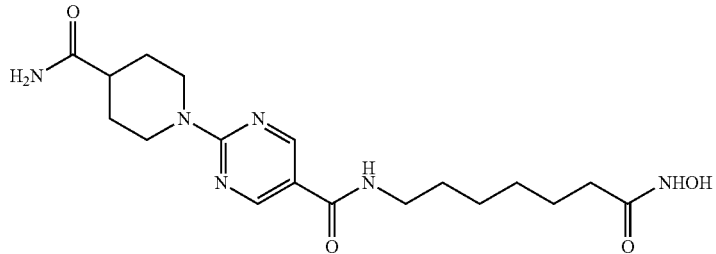

2-(4-carbamoylpiperidin-1-yl)-N-(7-
(hydroxyamino)-7-oxoheptyl)pyrimidine-5-
carboxamide
$IC_{50}$(nM) HDAC6 = 8 HDAC3 = 41

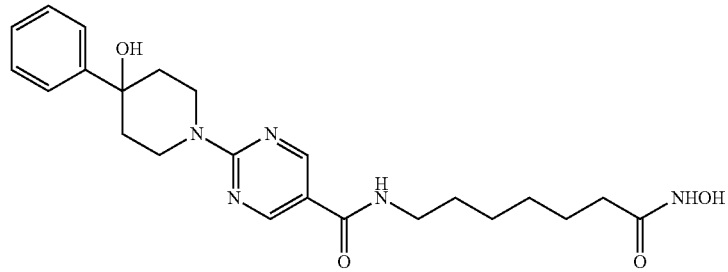

2-(4-hydroxy-4-phenylpiperidin-1-yl)-N-(7-
(hydroxyamino)-7-oxoheptyl)pyrimidine-5-
carboxamide
$IC_{50}$(nM) HDAC6 = 4 HDAC3 = 39

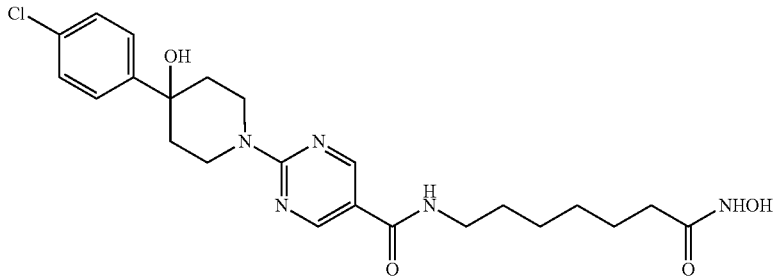

2-(4-(4-chlorophenyl)-4-hydroxypiperidin-1-
yl)-N-(7-(hydroxyamino)-7-
oxoheptyl)pyrimidine-5-carboxamide
$IC_{50}$(nM) HDAC6 = 4 HDAC3 = 53

TABLE 1-continued

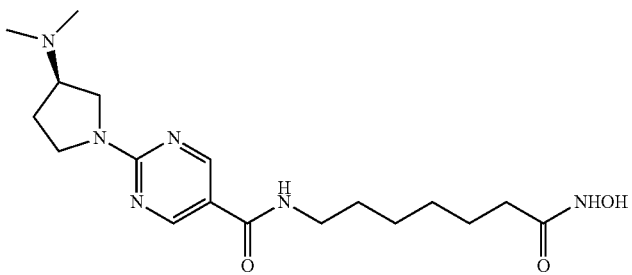

(R)-2-(3-(dimethylamino)pyrrolidin-1-yl)-N-
(7-(hydroxyamino)-7-oxoheptyl)pyrimidine-
5-carboxamide
IC$_{50}$(nM) HDAC6 = 33 HDAC3 = 80

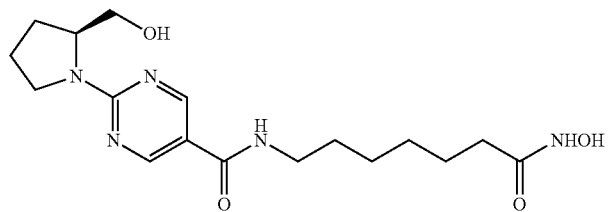

(S)-N-(7-(hydroxyamino)-7-oxoheptyl)-2-(2-
(hydroxymethyl)pyrrolidin-1-yl)pyrimidine-5-
carboxamide
IC$_{50}$(nM) HDAC6 = 7 HDAC3 = 30

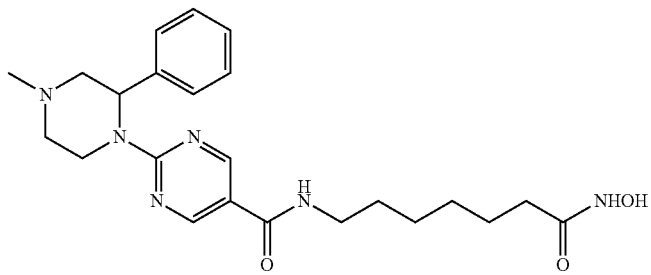

N-(7-(hydroxyamino)-7-oxoheptyl)-2-(4-
methyl-2-phenylpiperazin-1-yl)pyrimidine-5-
carboxamide
IC$_{50}$(nM) HDAC6 = 5 HDAC3 = 51

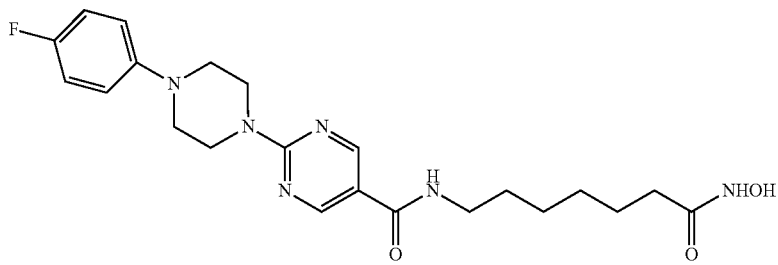

2-(4-(4-fluorophenyl)piperazin-1-yl)-N-(7-
(hydroxyamino)-7-oxoheptyl)pyrimidine-5-
carboxamide
IC$_{50}$(nM) HDAC6 = 5 HDAC3 = 52

TABLE 1-continued

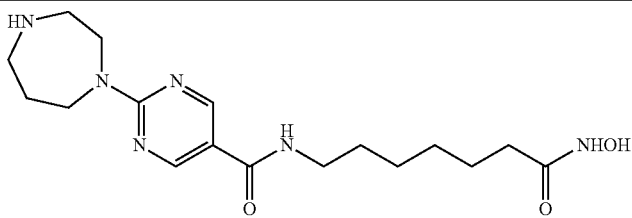

2-(1,4-diazepan-1-yl)-N-(7-(hydroxyamino)-
7-oxoheptyl)pyrimidine-5-carboxamide
IC$_{50}$(nM) HDAC6 = 19 HDAC3 = 34

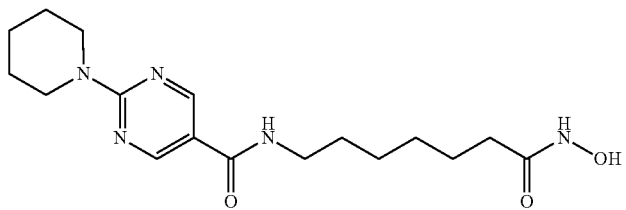 [SMILES: O=C(CCCCCCNC(=O)c1cnc(N2CCCCC2)nc1)NO]

N-(7-(hydroxyamino)-7-oxoheptyl)-2-
(piperidin-1-yl)pyrimidine-5-carboxamide
IC$_{50}$(nM) HDAC6 = 5 HDAC3 = 23

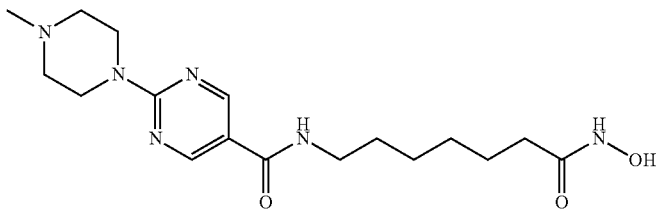 [SMILES: CN1CCN(c2ncc(C(=O)NCCCCCCC(=O)NO)cn2)CC1]

N-(7-(hydroxyamino)-7-oxoheptyl)-2-(4-
methylpiperazin-1-yl)pyrimidine-5-
carboxamide
IC$_{50}$(nM) HDAC6 = 18 HDAC3 = 87

In preferred embodiments, a compound useful in the invention has one or more of the following properties: the compound is capable of inhibiting at least one histone deacetylase; the compound is capable of inhibiting HDAC6; the compound is a selective HDAC6 inhibitor; the compound binds to the poly-ubiquitin binding domain of HDAC6; the compound is capable of inducing apoptosis in cancer cells (especially multiple myeloma cells, non-Hodgkin's lymphoma (NML) cells, breast cancer cells, acute myelogeous leukemia (AML) cells); and/or the compound is capable of inhibiting aggresome formation.

In certain preferred embodiments, a compound of the invention comprises a metal binding moiety, preferably a zinc-binding moiety such as a hydroxamate. As noted above, certain hydroxamates are potent inhibitors of HDAC6 activity; without wishing to be bound by theory, it is believed that the potency of these hydroxamates is due, at least in part, to the ability of the compounds to bind zinc. In preferred embodiments, a compound of the invention includes at least one portion or region which can confer selectivity for a biological target implicated in the aggresome pathway, e.g., a biological target having tubulin deacetylase (TDAC) or HDAC activity, e.g., HDAC6. Thus, in certain preferred embodiments, a compound of the invention includes a zinc-binding moiety spaced from other portions of the molecule which are responsible for binding to the biological target.

The invention also provides for a pharmaceutical composition comprising a compound of formula I, or a pharmaceutically acceptable ester, salt, or prodrug thereof, together with a pharmaceutically acceptable carrier.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

In another aspect, the invention provides a method of method of synthesizing a compound of formula I. The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3$H, $^2$H, $^{14}$C, $^{13}$C, $^{35}$S, $^{32}$P, $^{125}$I, and $^{131}$I) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999, and subsequent editions thereof.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In one aspect, the invention provides a method of selectively inhibiting HDAC6 over other HDACs in a subject, comprising administering a compound of formula I

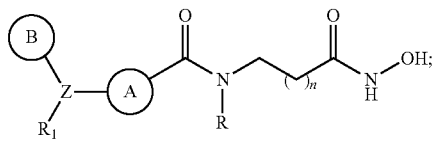

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In one embodiment, the compound of formula I has a selectivity for HDAC6 of 5 to 1000 fold. In certain embodiments, the selectivity for HDAC6 is 10-500 fold.

In another embodiment, the compound of formula I has a selectivity for HDAC6 when tested as described in Example 5 of about 5 to 1000 fold. In certain embodiments, the selectivity for HDAC6 is 10-500 fold.

In another aspect, the invention provides a method of treating a disease mediated by HDAC-6 in a subject comprising administering to the subject a compound of formula I

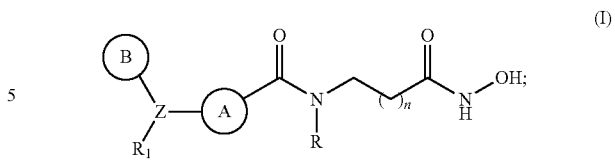

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In one embodiment, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, gliobastoma, hepatocellular carcinoma, papillary renal carcinoma, head and neck squamous cell carcinoma, leukemias, lymphomas, myelomas, and solid tumors.

In a further embodiment, the cancer is multiple myeloma.

In another embodiment, the disease is Wilson's disease, spinocerebellar ataxia, prion disease, Parkinson's disease, Huntington's disease, amytrophic lateral sclerosis, amyloidosis, Alzheimer's disease, Alexander's disease, alcoholic liver disease, cystic fibrosis, Pick's Disease, spinal muscular dystrophy or Lewy body dementia.

In certain embodiments, the disease is rheumatoid arthritis, osteoarthritis; rheumatoid spondylitis; psoriasis; post ischemic perfusion injury; inflammatory bowel disease; chronic inflammatory pulmonary disease, eczema, asthma, psoriasis, ischemia/reperfusion injury, ulcerative colitis, acute respiratory distress syndrome, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis, glomerulonephritis, hemolytic anemia, aplasic anemia, idiopathic thrombocytopenia, neutropenia, ulcerative colitis, Crohn's disease, host versus graft disease, allograft rejection, chronic thyroiditis, Graves' disease, schleroderma, diabetes, active hepatitis, primary binary cirrhosis, myasthenia gravis, multiple sclerosis (MS), systemic lupus erythematosus, atopic dermatitis, contact dermatitis, skin sunburns, chronic renal insufficiency, Stevens-Johnson syndrome, idiopathic sprue, sarcoidosis, Guillain-Barre syndrome, uveitis, conjunctivitis, keratoconjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, or chronic inflammatory pulmonary disease.

In other aspects, the invention provides a method of treating a subject suffering from or susceptible to multiple myeloma comprising administering to a subject in need thereof a therapeutically effective amount of a compound of formula I,

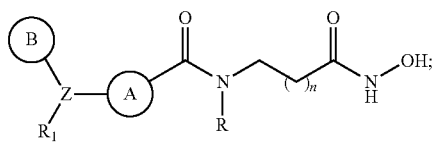

(I)

or a pharmaceutically acceptable salt, ester or prodrug thereof,
wherein,
Z is N or CR*, wherein R* is an optionally substituted alkyl, an optionally substituted acyl, an optionally substituted aryl or an optionally substituted heteroaryl;
ring A is an optionally substituted aryl or an optionally substituted heteroaryl;
ring B is an optionally substituted aryl or an optionally substituted heteroaryl;
$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;
or ring B and $R_1$ may together with the atom to which each is attached, form an optionally substituted heterocyclic, or an optionally substituted heteroaryl;
or R* and $R_1$ together with the atom to which each is attached, may form an optionally substituted carbocyclic, optionally substituted heterocyclic, optionally substituted aryl or optionally substituted heteroaryl ring;
R is H or an optionally substituted alkyl; or R and ring A may be joined to form a fused bicyclic ring which may be optionally substituted;
each $R_2$ is independently alkyl, cycloalkyl, heterocloalkyl, aryl, or heteroaryl, each of which is optionally substituted;
each $R_3$ is independently alkyl, cycloalkyl, heterocloalkyl, aryl, or heteroaryl, each of which is optionally substituted;
n is 4, 5, 6, 7 or 8; and
p is 0, 1, or 2;
to thereby treat the subject suffering from or susceptible to multiple myeloma.

In various embodiments, the invention provides a method further comprising co-administering one or more of a chemotherapeutic agent, radiation agent, hormonal agent, biological agent or an anti-inflammatory agent to the subject.

In a further embodiment, the chemotherapeutic agent is tamoxifen, trastuzamab, raloxifene, doxorubicin, fluorouracil/5-fu, pamidronate disodium, anastrozole, exemestane, cyclophosphamide, epirubicin, letrozole, toremifene, fulvestrant, fluoxymester-one, trastuzumab, methotrexate, megastrol acetate, docetaxel, paclitaxel, testolactone, aziridine, vinblastine, capecitabine, goselerin acetate, zoledronic acid, taxol, vinblastine, or vincristine.

In another embodiment, the invention provides a method wherein the subject is a human.

In another aspect, the invention provides a kit comprising a compound capable of inhibiting HDAC activity selected from one or more compounds of formula I

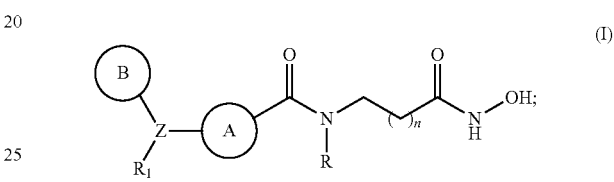

(I)

or a pharmaceutically acceptable salt, ester or prodrug thereof,
wherein,
Z is N or CR*, wherein R* is an optionally substituted alkyl, an optionally substituted acyl, an optionally substituted aryl or an optionally substituted heteroaryl;
ring A is an optionally substituted aryl or an optionally substituted heteroaryl;
ring B is an optionally substituted aryl or an optionally substituted heteroaryl;
$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;
or ring B and $R_1$ may together with the atom to which each is attached, form an optionally substituted heterocyclic, or an optionally substituted heteroaryl;
or R* and $R_1$ together with the atom to which each is attached, may form an optionally substituted carbocyclic, optionally substituted heterocyclic, optionally substituted aryl or optionally substituted heteroaryl ring;
R is H or an optionally substituted alkyl; or R and ring A may be joined to form a fused bicyclic ring which may be optionally substituted;
each $R_2$ is independently alkyl, cycloalkyl, heterocloalkyl, aryl, or heteroaryl, each of which is optionally substituted;
each $R_3$ is independently alkyl, cycloalkyl, heterocloalkyl, aryl, or heteroaryl, each of which is optionally substituted;
n is 4, 5, 6, 7 or 8; and
p is 0, 1, or 2;
and instructions for use in treating multiple myeloma.

As discussed above, the present invention provides compounds useful for the treatment of various diseases. In certain embodiments, the compounds of the present invention are useful as inhibitors of histone or tubulin deacetylases and thus are useful as anti-cancer agents, and thus may be useful in the treatment of cancer, by effecting tumor cell death or inhibiting the growth of tumor cells. In certain exemplary embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the compounds are useful in the treatment of multiple myeloma.

The compounds of the invention are especially effective to treat or prevent inflammatory, immune and autoimmune diseases including, but not limited to, arthritic conditions, such as, rheumatoid arthritis, osteoarthritis; rheumatoid spondylitis; psoriasis; post ischemic perfusion injury; inflammatory bowel disease; chronic inflammatory pulmonary disease, eczema, asthma, psoriasis, ischemia/reperfusion injury, ulcerative colitis, acute respiratory distress syndrome, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis, glomerulonephritis (with or without nephrotic syndrome), autoimmune hematologic disorders (e.g. hemolytic anemia, aplasic anemia, idiopathic thrombocytopenia and neutropenia), autoimmune gastritis and autoimmune inflammatory bowel diseases (e.g. ulcerative colitis and Crohn's disease), host versus graft disease, allograft rejection, chronic thyroiditis, Graves' disease, scleroderma, diabetes (type I and type II), active hepatitis (acute and chronic), primary binary cirrhosis, myasthenia gravis, multiple sclerosis (MS), systemic lupus erythematosus, atopic dermatitis, contact dermatitis, skin sunburns, chronic renal insufficiency, Stevens-Johnson syndrome, idiopathic sprue, sarcoidosis, Guillain-Barre syndrome, uveitis, conjunctivitis, keratoconjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive diseases of the airways.

Additionally, the inventive compounds may also be useful in the treatment of protozoal infections. The inventive compounds are also useful in the treatment of diseases associated with aberrant protein catabolism, for example, protein degradation disorders, disorders associated with misfolded proteins, and protein deposition disorders. In certain embodiments, the compound are useful in the treatment of the protein deposition disorders, Wilson's disease, spinocerebellar ataxia, prion disease, Parkinson's disease, Huntington's disease, amyotrophic lateral sclerosis, spinal muscular atrophy, spinal and bulbar muscular atrophy, amyloidosis, Alzheimer's disease, Alexander's deases, alcoholic liver disease, cystic fibrosis, Pick's disease, and Lewy body dementia. In certain exemplary embodiments, the compounds of the invention are useful for disorders associated with histone deacetylation activity. In certain exemplary embodiments, the compounds of the invention are useful for disorders associated with tubulin deacetylation activity.

Neurodegenerative diseases that can be treated or prevented include Alzheimer's disease, Parkinson's disease, cerebral ischaemia, traumatic neurodegenerative disease, Huntingtons's disease or chorea, senile dementia, memory disorder, vascular dementia, lesions associated with cerebral ischemia (stroke) and with cranial and medullary trauma, among others.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

As discussed above, the compounds of the invention are selective inhibitors of HDAC6 and, as such, are useful in the treatment of disorders modulated by histone deacetylases. As discussed above, the compounds of the invention are selective inhibitors of tubulin deacetylases and, as such, are useful in the treatment of disorders modulated by tubulin deacetylases. For example, compounds of the invention may be useful in the treatment of cancer (e.g., breast cancer, prostate cancer, multiple myeloma, leukemia, lymphoma, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia (e.g., CML, AML, CLL, ALL), lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors.

Multiple myeloma (MM) is a plasma cell malignancy which remains incurable despite conventional treatment (Gregory, et al. (1992) J Clin Oncol 10, 334-342) as well as high dose therapy and stem cell transplantation (Attal, M., et al. (2003) N Engl J Med 349, 2495-2502). Novel agents have recently been developed which target not only MM cells, but also the bone marrow (BM) microenvironment, and can overcome conventional drug resistance (Hideshima, T. & Anderson, K. C. (2002) Nat Rev Cancer 2, 927-937). For example, the proteasome inhibitor bortezomib (formally PS-341) induces significant anti-tumor activity in human MM cell lines and freshly isolated patient MM cells (Hideshima, T. & Anderson, K. C. (2002) Nat Rev Cancer 2, 927-937; Hideshima, et al. (2001) Cancer Res. 61, 3071-3076; Mitsiades, N., et al. (2002) Proc Natl Acad Sci USA 99, 14374-14379; Hideshima, T., et al. (2002) J Biol Chem 277, 16639-47; Mitsiades, N., et al. (2003) Blood 101, 2377-80; Chauhan, D., et al (2003) Cancer Res 63, 6174-6177; Hideshima, T., et al. (2003) Blood 101, 1530-1534; Hideshima, T., et al. (2003) Oncogene 22, 8386-8393; Hideshima, T., et al. (2004) Oncogene 23, 8766-8776) associated with c-Jun NH2-terminal kinase (JNK) (also known as stress-activated protein kinase) and caspase activation, followed by apoptosis (Hideshima, T., et al. (2001) Cancer Res. 61, 3071-3076; Mitsiades, N., et al. (2002) Proc Natl Acad Sci USA 99, 14374-14379; Hideshima, T., et al. (2003) Blood 101, 1530-1534). Bortezomib also inhibits adherence of MM cells to bone marrow stromal cells (BMSCs) by downregulating adhesion molecules (ICAM-I and VCAM-I) (Hideshima, T., et al. (2001) Oncogene 20, 4519-4527); as well as induces cleavage of DNA-protein kinase catalytic subunit and ataxia telangiectasia mutated, suggesting that bortezomib also inhibits DNA repair. Neither IL-6 nor adherence of MM cells to BMSCs protects against bortezomib-induced apoptosis. Without wishing to be bound by any scientific theory, bortezomib enhances sensitivity and can overcome resistance in MM cells to conventional chemotherapeutic agents, especially to DNA damaging agents (Mitsiades, N., et al. (2003) Blood 101, 2377-80). In support of this, a phase II trial of bortezomib treatment of 202 patients with refractory relapsed MM demonstrated 35% responses, including 10% complete and near complete responses (Richardson, P. G., et al. (2003) N Engl J Med 348, 2609-2617); however, 65% of patients did not respond. Heat-shock protein (hsp)-27 mediates bortezomib-resistance; conversely, inhibiting hsp-27 expression using hsp-27 antisense, p38 mitogen-activated protein kinase (MAPK) siRNA, or p38 MAPK inhibitor to downregulate hsp-27 can restore MM cell susceptibility to bortezomib (Chauhan, D., et a. (2003) Cancer Res 63, 6174-6177; Hideshima, T., et al. (2004) Oncogene 23, 8766-8776).

In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. Accordingly, without wishing to be bound to any particular theory, the inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099,562; 5,886,026; and 5,304,121; each of which is incorporated herein by reference. The coatings are typically biocompatible polymeric materials such as a hydrogel polymer, polymethyldisiloxane. polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiments, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and a carrier suitable for coating said implantable device. In still another aspect, the present invention includes an implantable device coated with a composition comprising a compound of the present invention as described generally above, and a carrier suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal-esophageal, tracheal/bronchial, urethral and/or vascular obstruction.

In certain embodiments, the invention provides a method of treatment of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising a compound of formula I, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other anti-proliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved chemotherapeutic agent, or it may be any one of a number of agents undergoing approval in the Food and Drug Administration that ultimately obtain approval for the treatment of protozoal infections and/or any disorder associated with cellular hyperproliferation. In certain other embodiments, the additional therapeutic agent is an anticancer agent, as discussed in more detail herein. In certain other embodiments, the compositions of the invention are useful for the treatment of protozoal infections. In the treatment of cancer or protein degradation disorders, the inventive compound may be combined with a proteasome inhibitor (e.g., bortezomib, R1 15777 FTI, MG132, NPI-0052, etc.). In the treatment of cancer or protein degradation disorders, the inventive compound may be combined with protein degradation inhibitor (e.g. another inventive compound, a tubacin-like compound, bortezomib, R1 15777 FTI, MG132, NPI-0052, SAHA, $^{166}$Ho-DOTMP, arsenic trioxide, 17-AAG, MG 132, etc.).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

The present invention encompasses pharmaceutically acceptable topical formulations of inventive compounds. The term "pharmaceutically acceptable topical formulation," as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et ah, Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, IU. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidine.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include, but not limited to, surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, antibodies, aptamers, siRNAs, oligonucletoides, enzyme, ion channel and receptor inhibitors or activators to name a-few), hyperthermia and cryotherapy, agents to attenuate any adverse effects (e.g., antiemetics), and other approved chemotherapeutic drugs, including, but not limited to, alkylating drugs (e.g., mechlorethamine, chlorambucil, Cyclophosphamide, Melphalan, Ifosfamide), antimetabolites (e.g., Methotrexate), purine antagonists and pyrimidine antagonists (e.g., 6-Mercaptopurine, 5-Fluorouracil, Cytarabile, Gemcitabine), spindle poisons (e.g., Vinblastine, Vincristine, Vinorelbine, Paclitaxel), podophyllotoxins (e.g., Etoposide, Irinotecan, Topotecan), antibiotics (Doxorubicin, Bleomycin, Mitomycin), nitrosoureas (e.g., Carmustine, Lomustine), inorganic ions (e.g., Cisplatin, Carboplatin), enzymes (e.g., Asparaginase), and hormones (e.g., Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/dmglistframe).

In certain embodiments, the pharmaceutical compositions of the present invention further comprise one or more additional therapeutically active ingredients (e.g., chemotherapeutic and/or palliative). For purposes of the invention, the term "palliative" refers to treatment that is focused on the relief of symptoms of a disease and/or side effects of a therapeutic regimen, but is not curative. For example, palliative treatment encompasses painkillers, antinausea medications, anti-pyretics, and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

The present compounds and compositions can be administered together with hormonal and steroidal anti-inflammatory agents, such as but not limited to, estradiol, conjugated estrogens (e.g., PREMARIN, PREMPRO, AND PREMPHASE), 17 beta estradiol, calcitonin-salmon, levothyroxine, dexamethasone, medroxyprogesterone, prednisone, cortisone, flunisolide, and hydrocortisone; non-steroidal anti-inflammatory agents, such as but not limited to, tramadol, fentanyl, metamizole, ketoprofen, naproxen, nabumetone, ketoralac, trometamine, loxoprofen, ibuprofen, aspirin, and acetaminophen; anti-TNF-α antibodies, such as infliximab (REMICADE™) and etanercept (ENBREL™).

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration to a subject suffering from or susceptible to a disease or disorder.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the invention and a co-agent, are both administered to a patient simultaneously in the form of a single entity or dosage. The term "non-fixed combination" means that the active ingredients, e.g., a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of variables in the structures in schemes herein are commensurate with those of corresponding positions in the formulae delineated herein.

Example 1

Synthesis of 2-(diphenylamino)-N-(7-(hydroxyamino)-7-oxoheptyl)pyrimidine-5-carboxamide

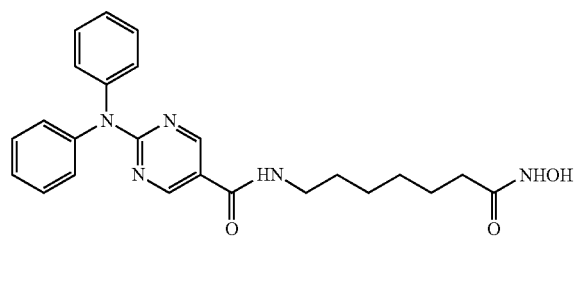

Reaction Scheme

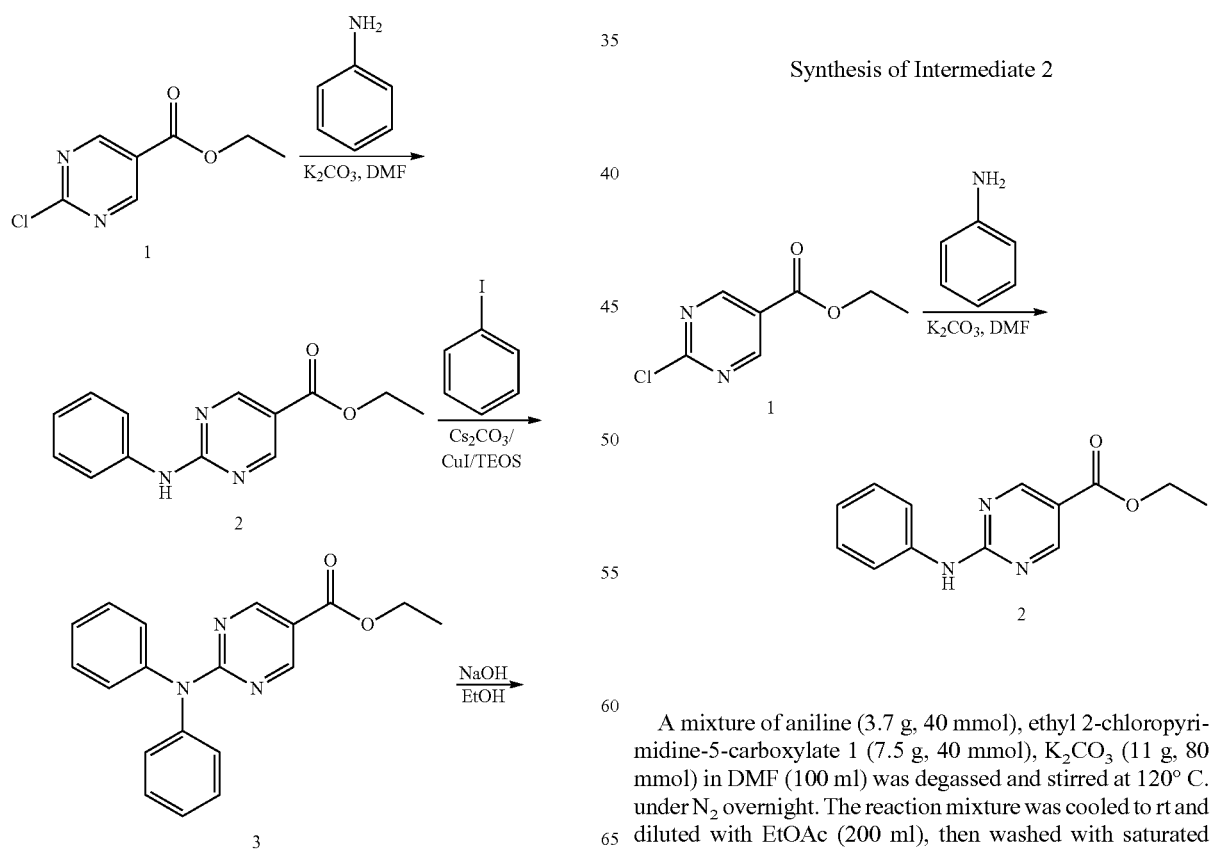

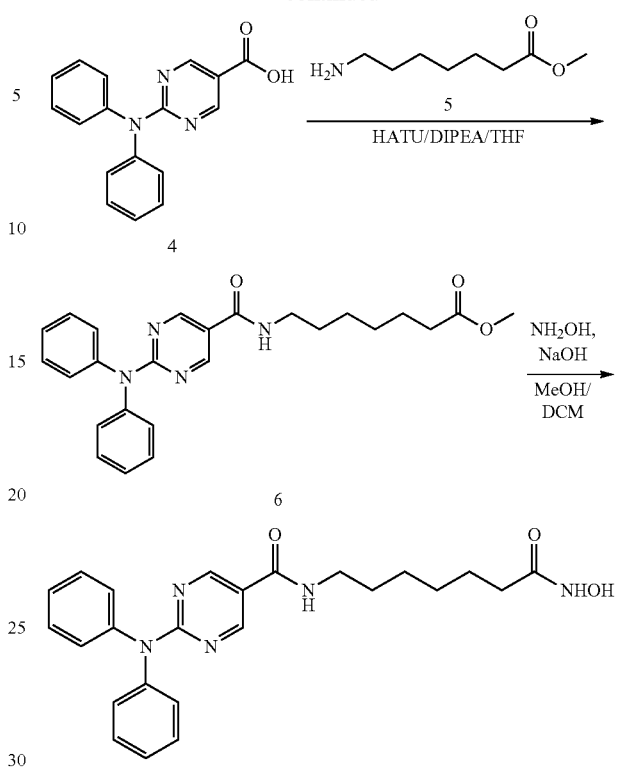

Synthesis of Intermediate 2

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

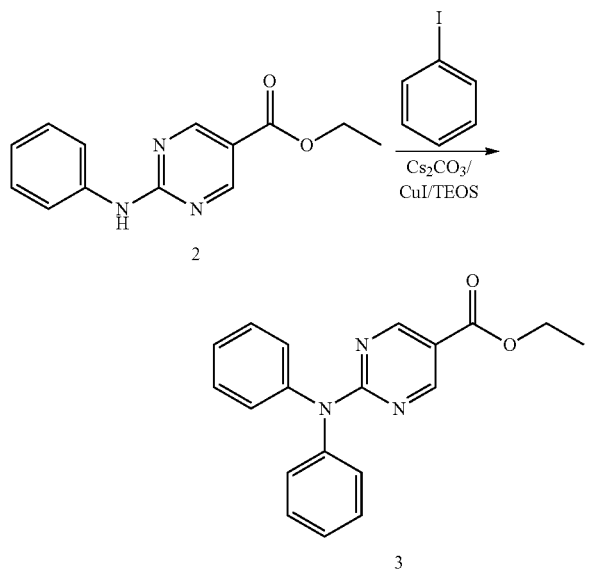

A mixture of the compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 h. After cooling to rt, the residue was diluted with EtOAc (200 ml) and 95% EtOH (200 ml), $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at rt for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

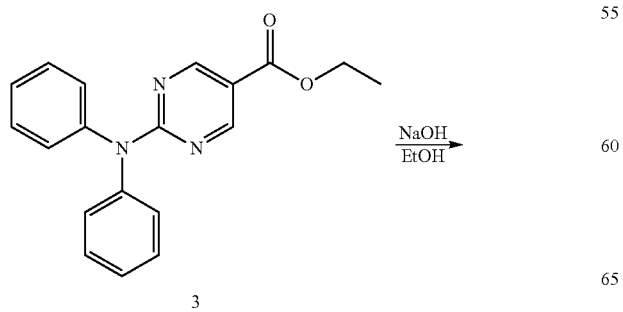

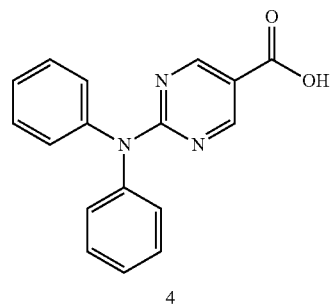

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

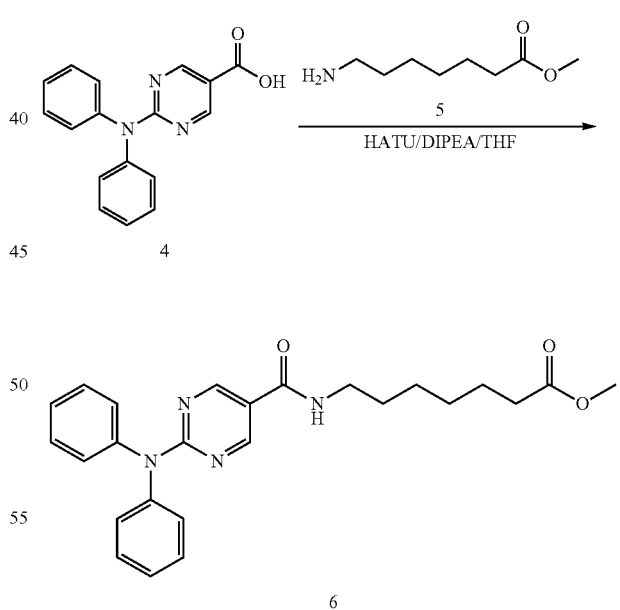

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at rt overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide

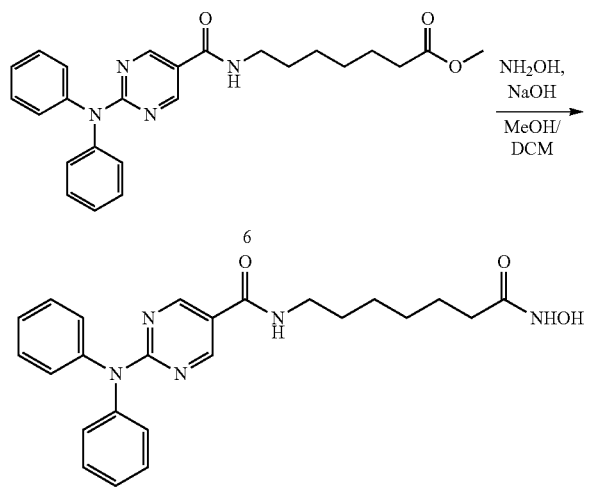

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at rt for 20 min. After removal of the solvent, the mixture was neutralized with 1M HCl to give a white precipitate. The crude product was filtered and purified by pre-HPLC to give a white solid (950 mg, 48%).

Example 2

Synthesis of 4-(2,6-dimethylphenylamino)-N-(7-(hydroxyamino)-7-oxoheptyl)-N-methylbenzamide

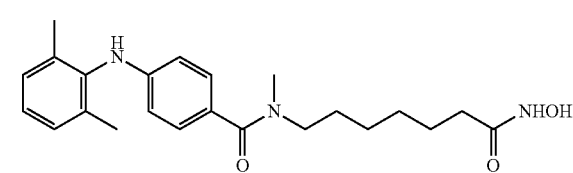

Reaction scheme:

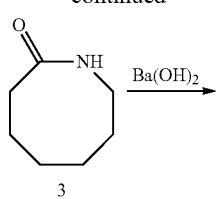

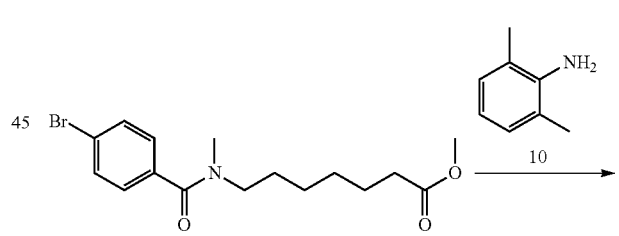

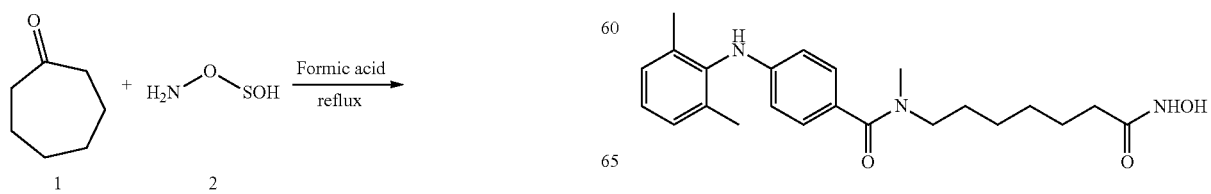

Synthesis of Intermediate 3

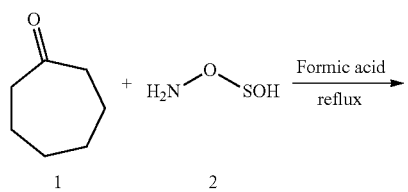

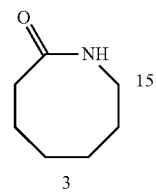

A 100-mL, three-necked flask was equipped with a magnetic stiffing bar, a ressure-equalizing dropping funnel, and a reflux condenser connected to a nitrogen flow line. The system was dried with a heat gun while it was flushed with dry nitrogen. The reaction vessel was then cooled in a water bath while a light positive pressure of nitrogen was maintained. The flask was charged with hydroxylamine-O-sulfonic acid 2 (8.48 g, 0.075 mol) and 95-97% formic acid (45 ml). A solution of cycloheptanone (5.61 g, 0.05 mol) (Note 3) in 15 ml of 95-97% formic acid was added with stirring over a 3-min period. After addition was complete, the reaction mixture was heated under reflux for 5 hr and then cooled to room temperature. The reaction mixture was quenched with 75 ml of ice-water. The aqueous solution was slowly neutralized to pH 7 with 6 N sodium hydroxide and extracted with three 100-ml portions of chloroform. The combined organic layers were dried with anhydrous magnesium sulfate. After removal of the solvent on a rotary evaporator, the product hexahydroazocinone was purified by distillation to give 3 (4.6 g 72%), 133-135° C./4 mmHg.

Synthesis of Intermediate 4

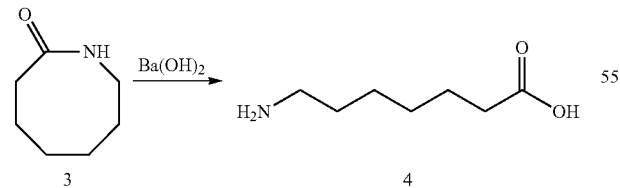

3 (5.6 g, 44.1 mmol) was combined with barium hydroxide (3.8 g, 26.95 mmol) and water (55 ml). The suspension was heated to 110° C. for 6 hours then cooled over an ice bath. Gaseous carbon dioxide was bubbled through the solution for 20 minutes. The suspension was filtered through a celite pad and the filtrate was concentrated to dryness. The residue was triturated with acetonitrile, collected, rinsed with ether and dried in vacuo to yield 4 as a white solid (6.0 g, 93%).

Synthesis of Intermediate 5

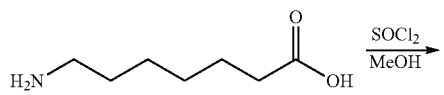

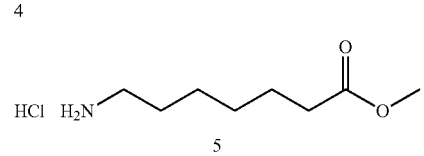

Thionyl chloride (1.81 ml, 24.8 mmol) was added dropwise with stirring to a cold suspension of 4 (1.8 g., 12.4 mmol) in methanol (30 ml.) at a rate so as to maintain the reaction temperature between −5° C. and −10° C. After addition of all the thionyl chloride, the mixture was allowed to warm to room temperature and was left to stir overnight. The mixture was then concentrated in vacuo to give a white solid which was triturated in ether (twice) to yield 2.38 g of 7-aminoheptanoic acid, methyl ester, hydrochloride (1:1) 5 as a white solid (4.8 g, 100%).

Synthesis of Intermediate 6

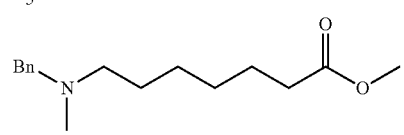

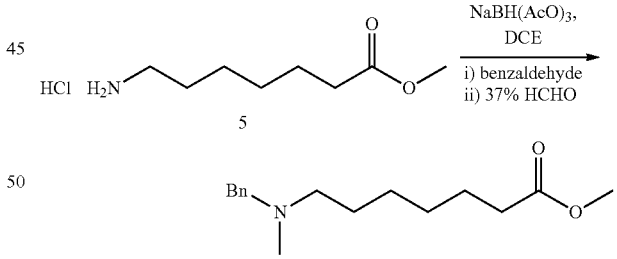

To a stirred mixture of 5 (1.67 g, 8.54 mmol), NaBH(AcO)₃ (10.8 g, 51.2 mmol) in 1,2 dichloroethane (50 ml) was added benzaldehyde (1.00 g, 9.40 mmol) at ambient temperature. The resulting solution was stirred at ambient temperature for 4 hr. 37% HCHO (513 mg, 17.0 mmol) was added dropwise within 1 minute. The resulting solution was stirred at ambient temperature overnight. The solution was filtered through celite pad, and the solid cake was washed with DCM (100 ml). The combined organic layers were evaporated to dryness, and the residue was purified by silica gel column chromatography (EtOAc) to afford 6 (1.41 g, 62.8%) as colorless oil.

Synthesis of Intermediate 7

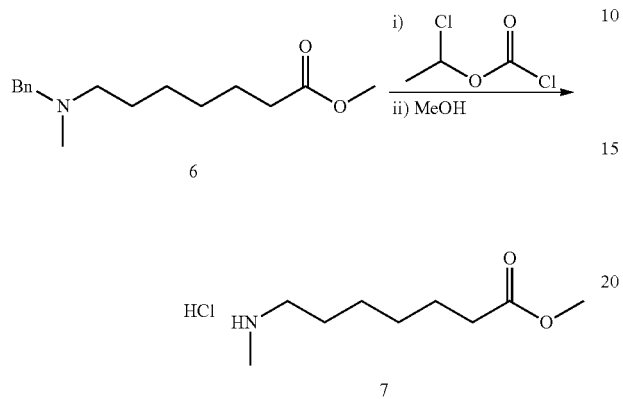

To a stirred solution of 6 (1.50 g, 5.69 mmol) in 1,2-dichloroethane (20 ml) was added 1-chloroethyl carbonochloridate (1.0 g, 6.8 mmol) dropwise at 0° C. within 2 minutes. The resulting solution was stirred at reflux for 10 hr. The solution was evaporated in vacuo, and to the residue was added MeOH (20 ml). The resulting mixture was stirred at reflux for 1 hr. The solution was then evaporated to dryness to afford crude 7 (1.3 g) as a solid which was used directly for next reaction without further purification.

Synthesis of Intermediate 9

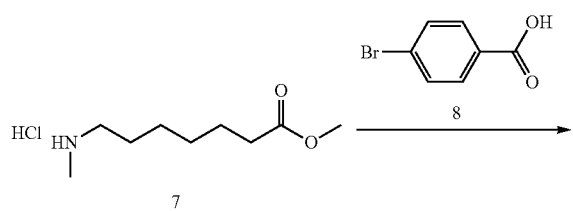

A mixture of acid 8 (2.01 g, 10 mmol), amine 7 (2.52 g, 12 mmol), DIPEA (5.17 g, 40 mmol) and HATU (4.561 g, 12 mmol) in DCM (30 ml) was stirred at rt for 4 hr. After the reaction mixture was evaporated to dryness, the residue was purified by silica gel column chromatography (petroleum ethers/EtOAc=1/1) to afford 9 (2.4 g, 66%) as a white solid.

Synthesis of Intermediate 11

A mixture of amine 10 (0.84 g, 6.94 mmol), bromide 9 (2.06 g, 5.78 mmol), Cs$_2$CO$_3$ (4.52 g, 13.8 mmol), Pd$_2$(dba)$_3$ (64 mg, 0.069 mmol) and Xantphos (81 mg, 0.14 mmol) in toluene (20 ml) was degassed and stirred at 100° C. overnight. The reaction mixture was cooled to rt and filtered through Celite. The filtrate was evaporated to dryness and the residue was purified by silica gel chromatography (petroleum ethers/EtOAc=1/1) to afford 11 (2.21 g, 96%) as pale yellow oil.

Synthesis of 4-(2,6-dimethylphenylamino)-N-(7-(hydroxyamino)-7-oxoheptyl)-N-methylbenzamide

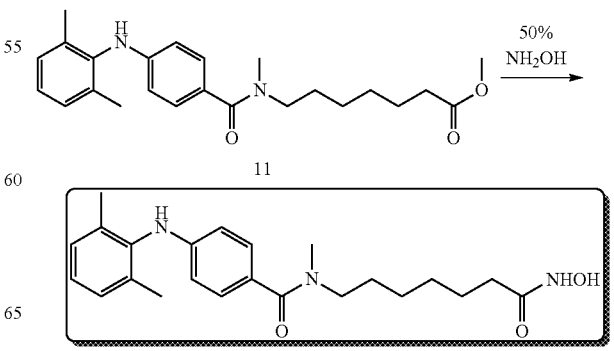

A mixture of the compound 11 (1.58 g, 4.00 mmol), 2N sodium hydroxide (10 ml, 20 mmol) in MeOH (8 ml) and DCM (60 ml) was stirred at 0° C. for 10 min. 50% aq. hydroxylamine (7.93 g, 120 mmol) was cooled to 0° C. and added to the mixture. And the resulting mixture was stirred at 0° C. for about 2 hr. The reaction mixture was neutralized with 2 N HCl to pH 7. After removal of solvent, the residue was extracted with EtOAc (10 ml). The organic layer was washed with water (20 ml), and brine (20 ml), dried over $Na_2SO_4$, evaporated in vacuo to afford ACY-161-89 (1.55 g, 98%) as a white solid.

Example 3

Synthesis of 2-(2,6-dimethylphenylamino)-N-(7-(hydroxyamino)-7-oxoheptyl)-N-methylpyrimidine-5-carboxamide

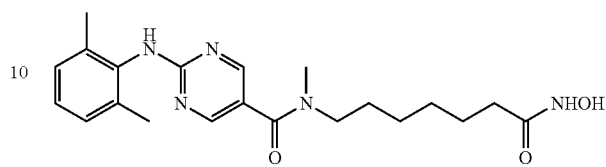

Reaction Scheme

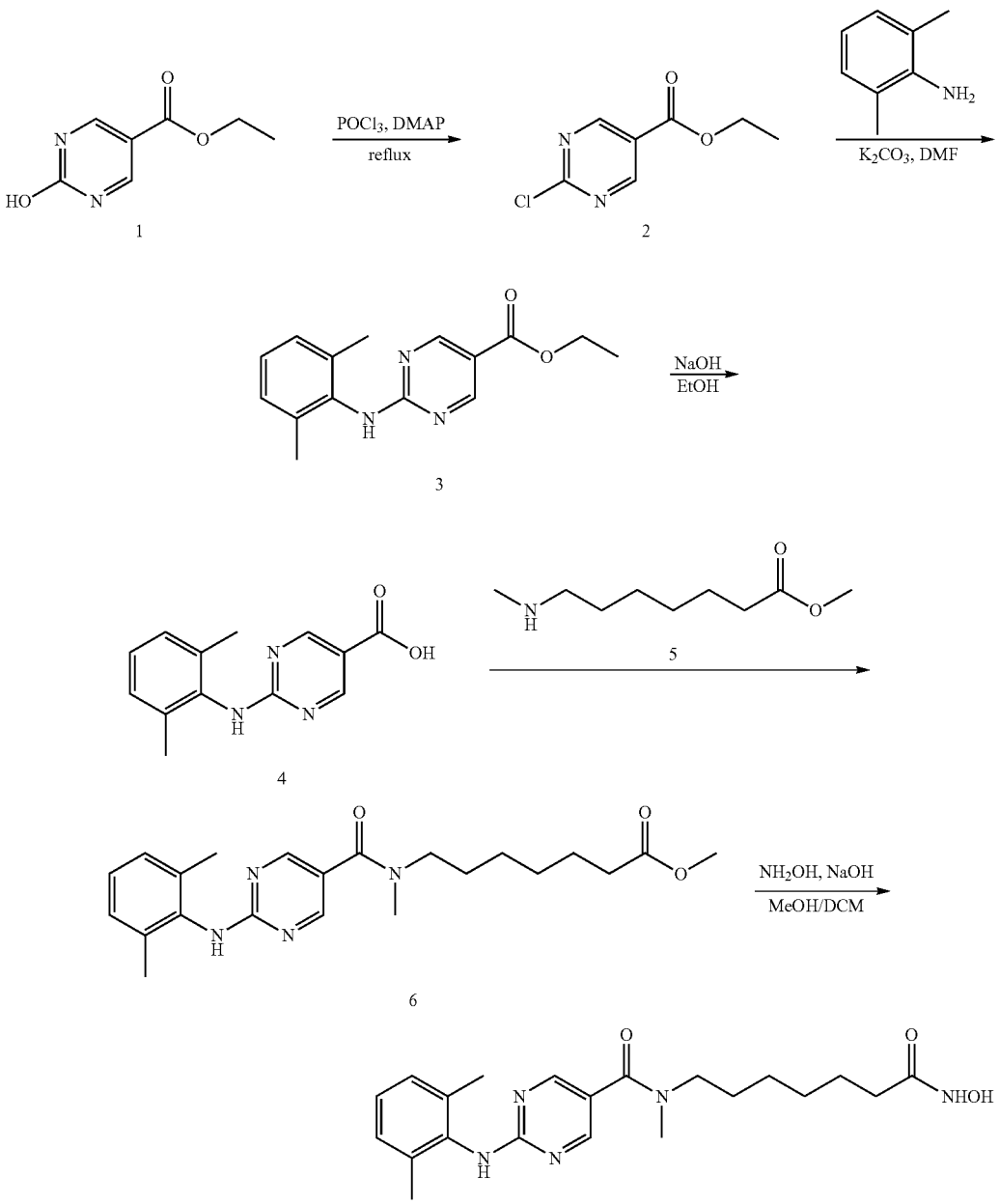

Synthesis of Intermediate 2

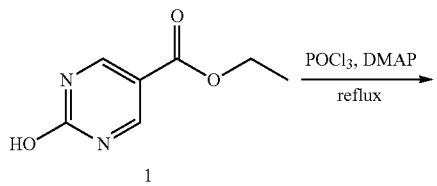

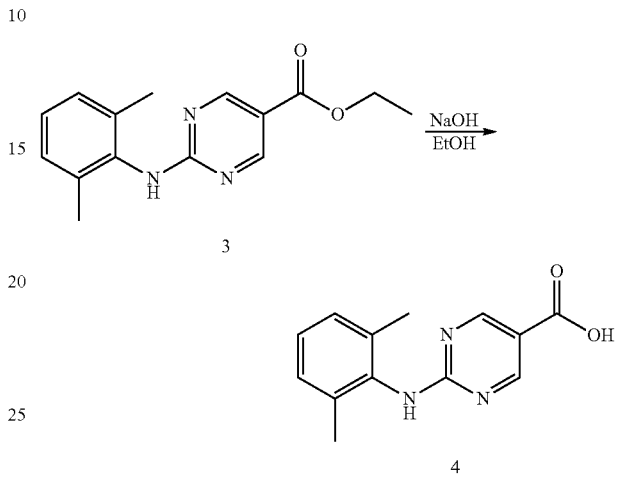

A mixture of the compound 1 (2 g, 12 mmol), DMAP (1.32 g, 11 mmol) and POCl$_3$ (20 mL) was heated at reflux for 1.5 h. After removal of the solvent, EA was added to the residual. The pH of the mixture was adjusted to 7 with aq. NaOH (2M), the organic layer was then separated, washed with brine. After removal of the solvent, the residual was extracted with PE and dried over Na$_2$SO$_4$, evaporation of the solvent gave a light yellow solid (1 g, 45%).

Synthesis of Intermediate 3

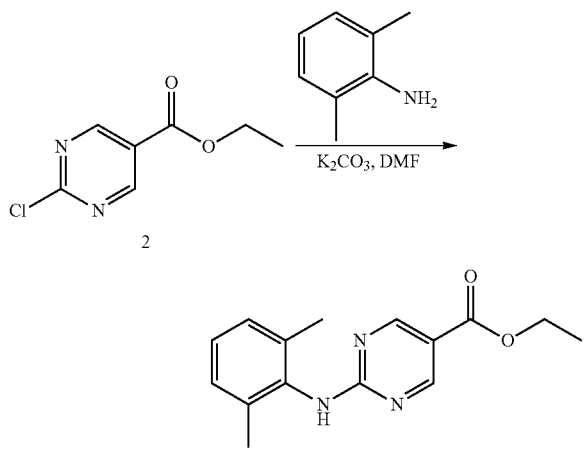

A mixture of aniline (325 mg, 2.68 mmol), compound 2 (500 mg, 2.68 mmol), K$_2$CO$_3$ (370 mg, 2.68 mmol) in DMF (10 mL) was degassed and stirred at 140° C. overnight. The reaction mixture was cooled to rt and filtered. The filtrate washed with water (2×20 mL) and brine (2×20 mL), extracted with EA. The organic layer was dried over Na$_2$SO$_4$, and evaporated to dryness. The residue was purified by silica gel chromatography (PE/EA=5/1) to give the crude product as a brown oil (320 mg, 44%).

Synthesis of Intermediate 4

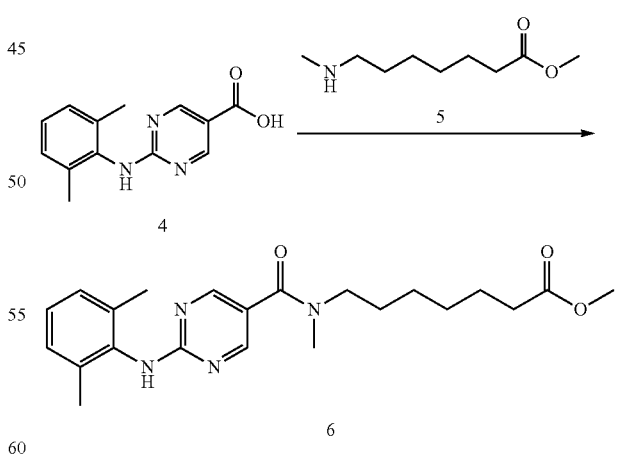

2M NaOH (15 mL) was added to a solution of the compound 3 (320 mg, 1.18 mmol) in EtOH (15 mL). The mixture was stirred at 60° C. for 10 min. The solution was neutralized with 2M HCl and extracted with EA (2×60 mL). The organic layer was washed with water (2×20 mL), brine (2×20 mL), and dried over Na$_2$SO$_4$. Evaporation of the solvent left a white solid (270 mg, 94%).

Synthesis of Intermediate 6

A mixture of compound 4 (270 mg, 1.11 mmol), compound 5 (231 mg, 1.33 mmol), HATU (506 mg, 1.33 mmol), DIPEA (574 mg, 4.44 mmol) in THF (30 mL) was stirred at rt overnight. The reaction mixture was filtered. The filtrate was evaporated to dryness and the residue was purified by pre-TLC (PE/EA=1/2) to give a brown oil (320 mg, 72%).

Synthesis of 2-(2,6-dimethylphenylamino)-N-(7-(hydroxyamino)-7-oxoheptyl)-N-methylpyrimidine-5-carboxamide

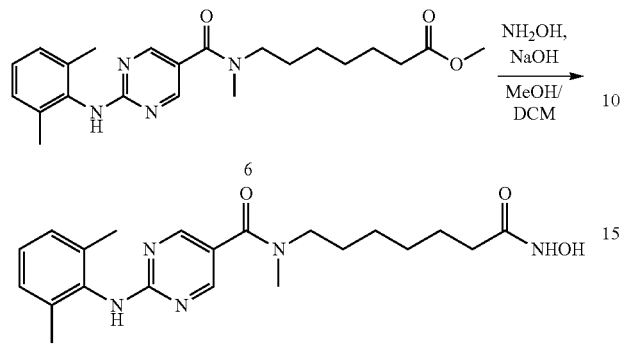

A mixture of the compound 6 (200 mg, 0.50 mmol), NaOH (2M, 2 mL) in MeOH (8 mL) and DCM (4 mL) was stirred at 0° C. for 10 min. Hydroxylamine (0.4 mL) was cooled to 0° C. and added to the mixture. After the resulting mixture was stirred at rt for 20 min, the organic solvent was removed in vacuo. The residue was acidified with 1M HCl to pH 7 and extracted with EA. The organic layer was washed with water (2×20 mL), brine (2×20 mL), and dried over Na$_2$SO$_4$, evaporated to dryness, and the residue was purified by pre-TLC (DCM/MeOH=5/1) to give a brown solid (106 mg, 53%).

Example 4

Synthesis of N-(7-(hydroxyamino)-7-oxoheptyl)-4-(hydroxydiphenylmethyl)benzamide Reaction Scheme

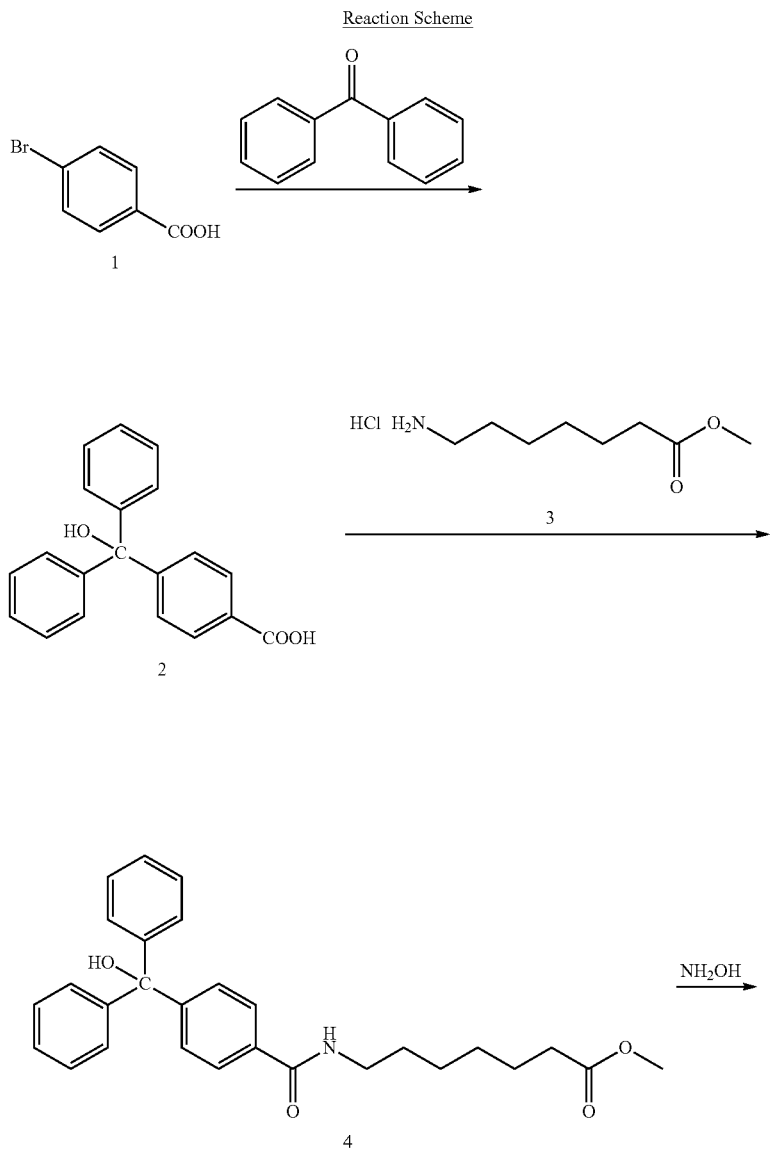

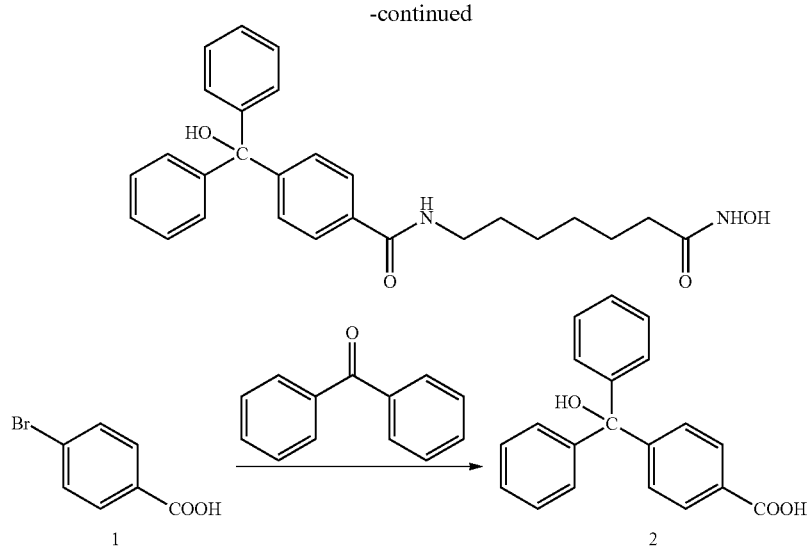

To a solution of 1 (201 mg, 1 mmol) in dry THF (5 ml), n-butyllithium solution (1.6 M in hexane, 1.5 ml) was added dropwise at −65° C. After 5 minutes, a solution of benzophenone (182 mg in 5 ml dry THF) was added over 10 minutes (exothermic). The mixture was stirred for further 30 minutes at −65° C. and overnight at r.t. The reaction mixture was quenched with sat. NH$_4$Cl (10 ml) and concentrated under reduced pressure. The mixture was acidified to pH 4 with 2N HCl, extracted with ethyl acetate (2×10 ml). The organic layer was separated, dried over Na2SO4 and concentrated to dryness. The residue was purified with prep-TLC (DCM/MeOH=10:1) to give compound 2 as a white solid (205 mg, 67%).

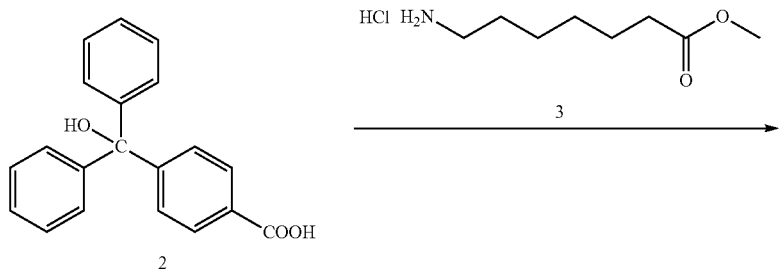

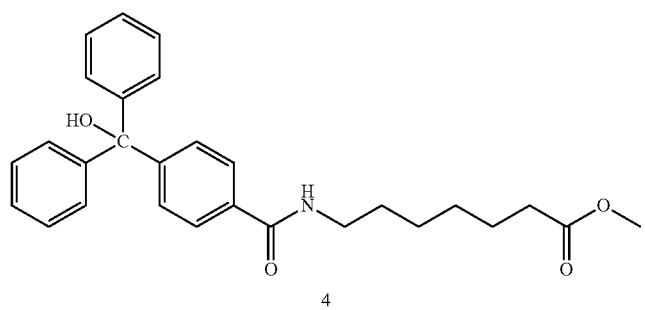

A solution of 2 (150 mg, 0.49 mmol), EDCI (190 mg, 0.98 mmol), HOBt (132 mg, 0.98 mmol) and 3 (190 mg, 0.98 mmol) in THF (10 mL) was stirred at r.t for 2 h. The reaction mixture was concentrated under reduced pressure and the residue was purified by prep-TLC to give compound 4 as an yellow oil (124 mg, 56%).

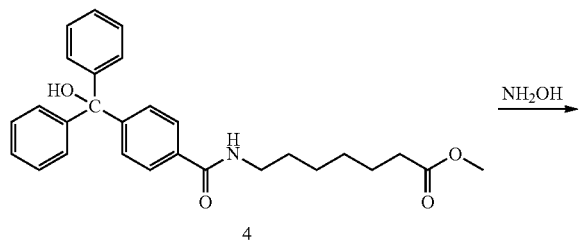

A solution of 4 (124 mg, 0.27 mmol) in MeOH (5 mL) was treated with NaOH (sat. in MeOH, 1.0 ml) and aq. $NH_2OH$ (50 wt %, 0.55 ml) sequentially and was stirred at r.t for 30 min. The reaction mixture was slowly acidified to pH 6-7 with 2N HCl, and extracted with ethyl acetate (2×5 ml). The organic layer was separated, dried over Na2SO4 and concentrated under reduced pressure to afford the titled compound as a yellow solid (111 mg, 90%).

Example 5

HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 μM TCEP) to 6 fold their final concentration. The HDAC enzymes (purchased from BPS Biosciences) were diluted to 1.5 fold their final concentration in assay buffer. The tripeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6). Five μl compounds and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The IC50 was determined using Graph Pad Prism by a four parameter curve fit.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A method of treating multiple myeloma in a subject comprising administering to the subject the compound:

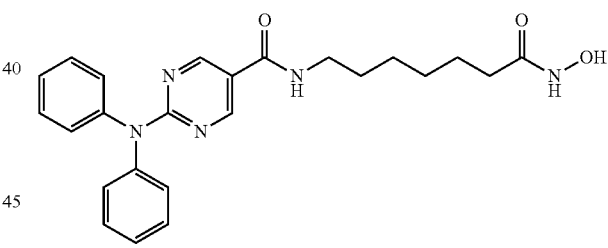

or a pharmaceutically acceptable salt thereof.

2. A method of treating multiple myeloma in a subject comprising administering to the subject the compound:

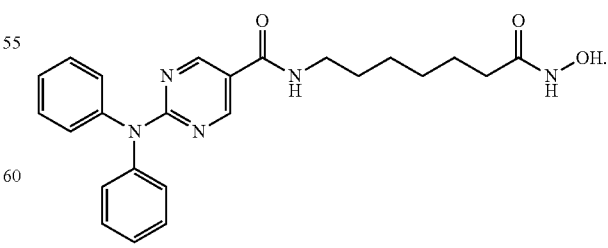

3. A method of treating multiple myeloma in a subject comprising administering to the subject a pharmaceutical composition comprising the compound:

143
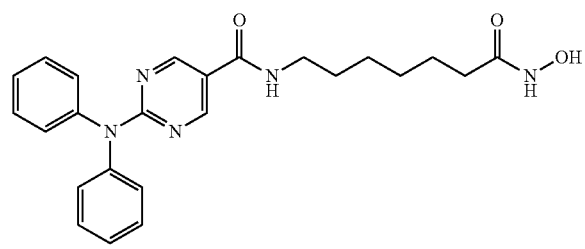 [SMILES: O=C(CCCCCCNC(=O)c1cnc(N(c2ccccc2)c2ccccc2)nc1)NO]
or a pharmaceutically acceptable salt thereof, together with a pharmaceutically acceptable carrier.
4. A method of treating multiple myeloma in a subject comprising administering to the subject a pharmaceutical composition comprising the compound:
144
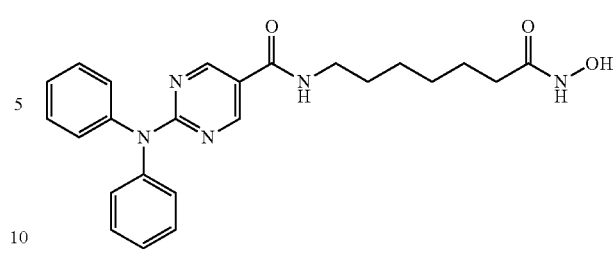
together with a pharmaceutically acceptable carrier.
* * * * *